(12) United States Patent
Matsumoto et al.

(10) Patent No.: US 7,582,651 B2
(45) Date of Patent: Sep. 1, 2009

(54) PYRROLOPYRIDINE DERIVATIVE AND USE THEREOF

(75) Inventors: Takahiro Matsumoto, Hyogo (JP); Osamu Kurasawa, Nishinomiya (JP); Tsuneo Oda, Ibaraki (JP); Hiroshi Nagabukuro, Osaka (JP); Manabu Mochizuki, Suita (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 538 days.

(21) Appl. No.: 10/520,784

(22) PCT Filed: Jul. 10, 2003

(86) PCT No.: PCT/JP03/08791

§ 371 (c)(1),
(2), (4) Date: Jan. 10, 2005

(87) PCT Pub. No.: WO2004/007495

PCT Pub. Date: Jan. 22, 2004

(65) Prior Publication Data

US 2006/0167038 A1 Jul. 27, 2006

(30) Foreign Application Priority Data

Jul. 11, 2002 (JP) ............... 2002-202204

(51) Int. Cl.
*A61K 31/44* (2006.01)
*C07D 513/02* (2006.01)
(52) U.S. Cl. ...................... 514/300; 546/113
(58) Field of Classification Search .............. 546/113; 514/300
See application file for complete search history.

(56) References Cited

U.S. PATENT DOCUMENTS

| | | | |
|---|---|---|---|
| 3,954,757 A * | 5/1976 | Arya et al. | ................ 544/316 |
| 6,673,797 B1 | 1/2004 | Matsuoka et al. | |
| 2004/0067964 A1 | 4/2004 | Matsuoka et al. | |

FOREIGN PATENT DOCUMENTS

| | | |
|---|---|---|
| EP | 0 275 667 A | 7/1988 |
| WO | WO 88/01997 | 3/1988 |
| WO | WO 99/00115 | 1/1999 |
| WO | WO 99/09970 | 3/1999 |
| WO | WO 00/75145 A | 12/2000 |

OTHER PUBLICATIONS

Wolff, Manfred E. "Burger's Medicinal Chemistry, 5ed, Part I", John Wiley & Sons, 1995, pp. 975-977.*
Banker, G.S. et al, "Modern Pharmaceutics, 3ed.", Marcel Dekker, New York, 1996, pp. 451 and 596.*
EP Search Report dated Sep. 1, 2006 issued in EP Application No. 03 74 1328.

* cited by examiner

*Primary Examiner*—Janet L. Andres
*Assistant Examiner*—Raymond Covington
(74) *Attorney, Agent, or Firm*—Sughrue Mion, PLLC

(57) ABSTRACT

A novel pyrrolopyridine derivative which is a compound represented by the formula

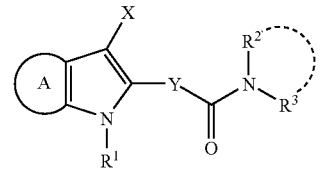

wherein Ring A represents an optionally substituted pyridine ring; X represents an electron-attracting group; Y represents an optionally substituted divalent $C_{1-6}$ chain hydrocarbon group; $R^1$ represents an optionally substituted hydrocarbon group; and $R^2$ and $R^3$ each independently represents hydrogen, an optionally substituted hydrocarbon group or an optionally-substituted heterocyclic group, or $R^2$ and $R^3$ may form an optionally substituted ring in cooperation with the adjacent nitrogen atom, or a salt of the compound. The pyrrolopyridine derivative has vanilloid receptor agonist activity and is useful as medicines such as a preventive/therapeutic agent and analgesic for overactive bladder.

8 Claims, No Drawings

SEQUENCE LISTING

<160> NUMBER OF SEQ ID NOS: 4

<210> SEQ ID NO 1
<211> LENGTH: 36
<212> TYPE: DNA
<213> ORGANISM: Artificial Sequence
<220> FEATURE:
<223> OTHER INFORMATION: primer/probe

<400> SEQUENCE: 1
ggggaattcg ccaccatgga acaacgggct agctta                36

<210> SEQ ID NO 2
<211> LENGTH: 41
<212> TYPE: DNA
<213> ORGANISM: Artificial Sequence
<220> FEATURE:
<223> OTHER INFORMATION: primer/probe

<400> SEQUENCE: 2
ggggcggccg cttatttctc ccctgggacc atggaatcct t          41

<210> SEQ ID NO 3
<211> LENGTH: 41
<212> TYPE: DNA
<213> ORGANISM: Artificial Sequence
<220> FEATURE:
<223> OTHER INFORMATION: primer/probe

<400> SEQUENCE: 3
ggggaattcg ccaccatgaa gaaatggagc agcacagact t          41

<210> SEQ ID NO 4
<211> LENGTH: 41
<212> TYPE: DNA
<213> ORGANISM: Artificial Sequence
<220> FEATURE:
<223> OTHER INFORMATION: primer/probe

<400> SEQUENCE: 4
ggggcggccg ctcacttctc cccggaagcg gcaggactct t          41

PYRROLOPYRIDINE DERIVATIVE AND USE THEREOF

This application is the National Phase filing of International Patent Application No. PCT/JP03/08791, filed Jul. 10, 2003.

TECHNICAL FIELD

The present invention relates to a pyrrolopyridine derivative useful as a medicine, and a production method and use thereof.

BACKGROUND ART

Conventionally, pyrrolopyridine derivatives which are useful as a medicine have been reported (WO99/61436, W088/01997).

W099/61436 discloses that the compound represented by the formula

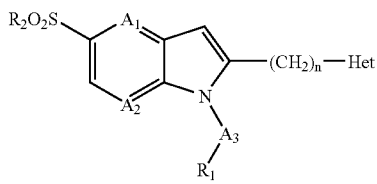

wherein Het represents an optionally substituted heterocyclic group; $A_1$ and $A_2$ each independently represent, —CH= or —N=; $A_3$ represents —CH$_2$—, etc.; $R_1$ represents a 4-fluorophenyl group, etc.; $R_2$ represents a $C_{1-3}$ alkyl group; n represents 0, 1 or 2 provided that when both of $A_1$ and $A_2$ are —CH=, $A_3$ represents —CH$_2$— or —SO$_2$—, shows anti-inflammatory action.

WO 88/01997 discloses that the compound represented by the formula

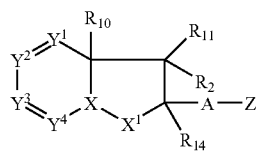

wherein one of $Y^1$ to $Y^4$ is —N—, and the others are —CH—, X is —C(R$_{15}$)—, $X^1$ is —N(R$_1$)—, $R_{10}$ and $R_{15}$, and, $R_{11}$ and $R_{14}$ form a bond, $R_1$ is primary or secondary $C_{1-4}$ alkyl, $R_2$ is substituted phenyl, primary or secondary $C_{1-6}$ alkyl, $C_{3-6}$ cycloalkyl or phenyl-(CH$_2$)$_m$—, A is —CH=CH— or —(CH$_2$)$_n$—, n=1, 2 or 3, and Z is —CH(OH)—CH$_2$—CH(OH)—CH$_2$—COOR$_8$ or

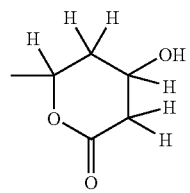

is useful as a hypolipoproteinemic and an agent for atherosclerosis.

Furthermore, as a compound having vanilloid receptor agonist activity, capsaicin derivatives disclosed in U.S. Pat. Nos. 5,099,030, 5,045,565, 5,403,868, 4,564,633, 4,544,669, 4,532,139, 4,544,668, 4,493,848, 4,460,602, 4,424,205, 4,443,473 and 4,401,663 are known.

U.S. Pat. No. 4,313,958 discloses that capsaicin can be used as an analgesic. JP-A-2001-513551 discloses that resiniferatoxin can be used as a therapeutic agent for urinary incontinence. JP-A-2001-158738 discloses a capsaicinoid-like substance as an analgesic. WO00/50387 also discloses a benzene derivative as a useful medicine.

DISCLOSURE OF INVENTION

It has been desired earnestly to develop a compound that has vanilloid receptor agonist activity and is useful as a medicine for treating acute/chronic, systemic and topical pain and/or inflammation, and for preventing and/or treating frequent urination and/or urinary incontinence, etc. caused by overactive bladder and cystitis. Therefore, an object of the present invention is to develop a compound which is useful as such medicine.

The present inventors have found that a novel pyrrolopyridine compound represented by the formula (I) which is characterized in the chemical structure by possessing an electron-attracting group at 3 position and an acrylamide group at 2 position, has unexpectedly excellent vanilloid receptor agonistic activity based on the specific chemical structure, and is useful as a medicine such as an analgesic and an agent for preventing and/or treating overactive bladder, and further they made extensive studies for it to reach completion of the present invention.

That is, the present invention provides:

(1) a compound represented by the formula

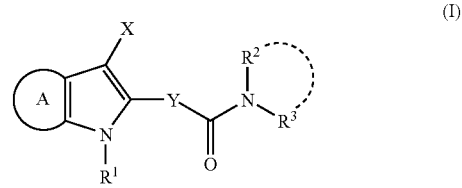

wherein Ring A represents an optionally substituted pyridine ring, X represents an electron-attracting group, Y represents an optionally substituted divalent $C_{1-6}$ chained hydrocarbon group, $R^1$ represents an optionally substituted hydrocarbon group, and $R^2$ and $R^3$ each independently represent a hydrogen atom, an optionally substituted hydrocarbon group or an optionally substituted heterocyclic group, or $R^2$ and $R^3$ may form an optionally substituted ring together with an adjacent nitrogen atom, or a salt thereof, (2) the compound as described in (1) which is a compound represented by the formula

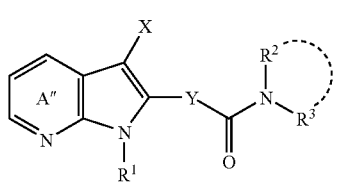

wherein Ring A" represents a pyridine ring which may have 1 to 3 substituents selected from a $C_{1-4}$ alkyl group and a mono-, di- or tri-halogeno-$C_{1-4}$ alkyl group and other symbols are as defined in (1), or a salt thereof, (3) the compound as described in (1), wherein X is a nitrile group, (4) the compound as described in (1), wherein Y is —CH=CH— or —(CH$_2$)$_2$—, (5) the compound as described in (1), wherein R$^1$ is (1) a C$_{5-7}$ cycloalkyl group optionally fused with a benzene ring, (2) a C$_{7-19}$ aralkyl group, (3) a 5- or 6-membered heterocyclic ring-C$_{1-4}$ alkyl group or (4) a C$_{6-14}$ aryloxy-C$_{1-4}$ alkyl group, each of which may have 1 to 4 substituents selected from a halogen atom, a C$_{1-4}$ alkyl group, a mono-, di- or tri-halogeno-C$_{1-4}$ alkyl group and a C$_{1-4}$ alkoxy group, (6) the compound as described in (1), wherein one of R$^2$ and R$^3$ is a hydrogen atom or a C$_{1-4}$ alkyl group, and the other is a 5- or 6-membered heterocyclic group, a C$_{6-14}$ aryl group, a C$_{7-19}$ aralkyl group, a C$_{3-10}$ cycloalkyl group, a 5- or 6-membered heterocyclic ring-C$_{1-4}$ alkyl group or C$_{1-6}$ alkyl group, each of which may have 1 to 4 substituents selected from a halogen atom, a C$_{1-4}$ alkyl group, a mono-, di- or tri-halogeno-C$_{1-4}$ alkyl group, a C$_{1-4}$ alkoxy group, a C$_{1-4}$ alkoxy-carbonyl group, a cyano group, a C$_{1-4}$ alkyl-carbonylamino group and a hydroxy group; or R$^2$ and R$^3$, together with an adjacent nitrogen atom, form a 5- or 6-membered nitrogen-containing heterocyclic ring optionally containing 1 to 3 hetero atoms selected from an oxygen atom, a sulfur atom and a nitrogen atom in addition to carbon atoms and one nitrogen atom, in which the nitrogen-containing heterocyclic ring may have 1 to 4 substituents selected from a halogen atom, a C$_{1-4}$ alkyl group, a mono-, di- or tri-halogeno-C$_{1-4}$ alkyl group, a C$_{1-4}$ alkoxy group and a C$_{1-4}$ alkoxy-carbonyl group, (7) (2E)-3-{3-cyano-4,6-dimethyl-1-[(1S)-1,2,3,4-tetrahydronaphthalen-1-yl]-1H-pyrrolo[2,3-b]pyridin-2-yl}-N-(3,4-dimethoxyphenyl)prop-2-enamide, (2E)-3-{3-cyano-4,6-dimethyl-1-[(1S)-1,2,3,4-tetrahydronaphthalen-1-yl]-1H-pyrrolo[2,3-b]pyridin-2-yl}-N-(3,4-dimethylphenyl)prop-2-enamide, (2E)-3-{3-cyano-4,6-dimethyl-1-[(1S)-1,2,3,4-tetrahydronaphthalen-1-yl]-1H-pyrrolo[2,3-b]pyridin-2-yl}-N-methyl-N-phenylprop-2-enamide, (2E)-3-{3-cyano-4,6-dimethyl-1-[(1S)-1,2,3,4-tetrahydronaphthalen-1-yl]-1H-pyrrolo[2,3-b]pyridin-2-yl}-N-(3-methylphenyl)prop-2-enamide, (2E)-3-{3-cyano-4,6-dimethyl-1-[(1S)-1,2,3,4-tetrahydronaphthalen-1-yl]-1H-pyrrolo[2,3-b]pyridin-2-yl}-N-(4-hydroxy-3-methoxyphenyl)prop-2-enamide, or salts thereof, (8) a prodrug of the compound as described in (1), (9) a medicine comprising the compound as described in (1) or a prodrug thereof,

(10) the medicine as described in (9) which is a vanilloid receptor agonist,

(11) the vanilloid receptor agonist as described in (10) which is for local administration,

(12) the vanilloid receptor agonist as described in (10) which is an agent for preventing and/or treating overactive bladder,

(13) the vanilloid receptor agonist as described in (10) which is an analgesic,

(14) a method of preventing and/or treating overactive bladder, comprising administering to a mammal in need an effective amount of the compound as described in (1) or a prodrug thereof,

(15) an analgesic method comprising administering to a mammal in need an effective amount of the compound as described in (1) or a prodrug thereof,

(16) use of the compound as described in (1) or a prodrug thereof for manufacturing an agent for preventing and/or treating overactive bladder, and

(17) use of the compound as described in (1) or a prodrug thereof for manufacturing an analgesic.

The present invention further provides:

(18) a method for producing the compound as described in (1), comprising subjecting a compound represented by the formula

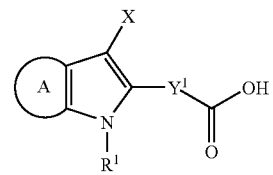

wherein y$^1$ represents an optionally substituted C$_{2-6}$ alkenylene group or C$_{2-6}$ alkynylene group and other symbols are as defined in (1), or a salt thereof, and a compound represented by the formula

wherein symbols are as defined in (1), or a salt thereof to reaction, and subsequently, if desired, to reduction reaction,

(19) a compound represented by the formula

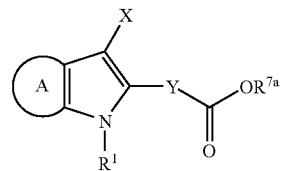

wherein R$^{7a}$ represents a hydrogen atom, an optionally substituted hydrocarbon group or an optionally substituted heterocyclic group and other symbols are as defined in (1), or a salt thereof.

BEST MODE FOR CARRYING OUT THE INVENTION

The "optionally substituted pyridine ring" represented by Ring A includes a pyridine ring represented by the formula

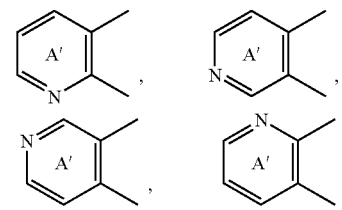

wherein Ring A' represents an optionally substituted pyridine ring.

The "substituent" of the "optionally substituted pyridine ring" represented by Ring A or Ring A' includes, for example, 1 to 3 substituents selected from a halogen atom (e.g., fluorine, chlorine, bromine, iodine, etc.), C$_{1-6}$ alkyl (e.g., methyl, ethyl, propyl, isopropyl, butyl, isobutyl, sec-butyl, tert-butyl, pentyl, hexyl, etc.), C$_{3-6}$ cycloalkyl (e.g., cyclopropyl, cyclobutyl, cyclopentyl, cyclohexyl, etc.), C$_{2-6}$ alkynyl (e.g., ethynyl, 1-propynyl, propargyl, etc.), C$_{2-6}$ alkenyl (e.g., vinyl, allyl, isopropenyl, butenyl, isobutenyl, etc.), $C_{7-11}$ aralkyl (e.g., benzyl, α-methylbenzyl, phenethyl, etc.), $C_{6-10}$ aryl (e.g., phenyl, naphthyl, etc.), $C_{1-6}$ alkoxy (e.g., methoxy, ethoxy, propoxy, isopropoxy, butoxy, isobutoxy, sec-butoxy, tert-butoxy, etc.), $C_{6-10}$ aryloxy (e.g., phenoxy, etc.), formyl, $C_{1-6}$ alkyl-carbonyl (e.g., acetyl, propionyl, butyryl, isobutyryl, etc.), $C_{6-10}$ aryl-carbonyl (e.g., a benzoyl group, a naphthoyl group, etc.), formyloxy, $C_{1-6}$ alkyl-carbonyloxy (e.g., acetyloxy, propionyloxy, butyryloxy, isobutyryloxy, etc.), $C_{6-10}$ aryl-carbonyloxy (e.g., benzoyloxy, naphthoyloxy, etc.), carboxyl, $C_{1-6}$ alkoxy-carbonyl (e.g., methoxycarbonyl, ethoxycarbonyl, propoxycarbonyl, isopropoxycarbonyl, butoxycarbonyl, isobutoxycarbonyl, tert-butoxycarbonyl, etc.), $C_{7-11}$ aralkyloxycarbonyl (e.g., benzyloxycarbonyl, etc.), carbamoyl, a mono-, di- or tri-halogeno-$C_{1-4}$ alkyl (e.g., chloromethyl, dichloromethyl, trifluoromethyl, 2,2,2-trifluoroethyl, etc.), oxo, amidino, imino, amino, mono-$C_{1-4}$ alkylamino (e.g., methylamino, ethylamino, propylamino, isopropylamino, butylamino, etc.), di-$C_{1-4}$ alkylamino (e.g., dimethylamino, diethylamino, dipropylamino, diisopropylamino, dibutylamino, methylethylamino, etc.), 3- to 6-membered cyclic amino optionally containing 1 to 3 hetero atoms selected from an oxygen atom, a sulfur atom and a nitrogen atom in addition to carbon atoms and one nitrogen atom (e.g., aziridinyl, azetidinyl, pyrrolidinyl, pyrrolinyl, pyrrolyl, imidazolyl, pyrazolyl, imidazolidinyl, piperidyl, morpholinyl, dihydropyridyl, pyridyl, N-methylpiperazinyl, N-ethylpiperazinyl, etc.), a 5- to 14-membered. (preferably 5- to 10-membered) (mono- to tri-cyclic, preferably mono- or bi-cyclic) heterocyclic group containing 1 to 4 (preferably 1 to 3) hetero atoms selected from a nitrogen atom, an oxygen atom and a sulfur atom in addition to carbon atoms (e.g., a 5-membered cyclic group containing 1 to 4 hetero atoms selected from an oxygen atom, a sulfur atom and a nitrogen atom in addition to carbon atoms such as 2- or 3-thienyl, 2- or 3-furyl, 1-, 2- or 3-pyrrolyl, 1-, 2- or 3-pyrrolidinyl, 2-, 4- or 5-oxazolyl, 3-, 4- or 5-isoxazolyl, 2-, 4- or 5-thiazolyl, 3-, 4- or 5-isothiazolyl, 3-, 4- or 5-pyrazolyl, 2-, 3- or 4-pyrazolidinyl, 2-, 4- or 5-imidazolyl, 1,2,3-triazolyl, 1,2,4-triazolyl and 1H- or 2H-tetrazolyl, a 6-membered cyclic group containing 1 to 4 hetero atoms selected from an oxygen atom, a sulfur atom and a nitrogen atom in addition to carbon atoms such as 2-, 3- or 4-pyridyl, N-oxide-2-, 3- or 4-pyridyl, 2-, 4- or 5-pyrimidinyl, N-oxide-2-, 4- or 5-pyrimidinyl, thiomorpholinyl, morpholinyl, piperidino, 2-, 3- or 4-piperidyl, tetrahydropyranyl, thiopyranyl, 1,4-oxazinyl, 1,4-thiazinyl, 1,3-thiazinyl, piperazinyl, triazinyl, 3- or 4-pyridazinyl, pyrazinyl and N-oxide-3- or 4-pyridazinyl, a bi- or tri-cyclic fused cyclic group containing 1 to 4 hetero atoms selected from an oxygen atom, a sulfur atom and a nitrogen atom in addition to carbon atoms (preferably, the 5- or 6-membered ring is a group formed by fusion of the above-mentioned 5- or 6-membered ring with one or two 5- or 6-membered cyclic groups optionally containing 1 to 4 hetero atoms selected from an oxygen atom, a sulfur atom and a nitrogen atom in addition to carbon atoms), such as indolyl, benzofuryl, benzothiazolyl, benzoxazolyl, benzimidazolyl, quinolyl, isoquinolyl, phthalazinyl, quinazolinyl, quinoxalinyl, indolizinyl, quinolizinyl, 1,8-naphthyridinyl, dibenzofuranyl, carbazolyl, acridinyl, phenanthridinyl, chromanyl, phenothiazinyl and phenoxazinyl, etc.), $C_{1-3}$ alkylenedioxy (e.g., methylenedioxy, ethylenedioxy, etc.), hydroxy, nitro, cyano, mercapto, sulfo, sulfino, phosphono, sulfamoyl, mono-$C_{1-6}$ alkylsulfamoyl (e.g., N-methylsulfamoyl, N-ethylsulfamoyl, N-propylsulfamoyl, N-isopropylsulfamoyl, N-butylsulfamoyl, etc.), di-$C_{1-6}$ alkylsulfamoyl (e.g., N,N-dimethylsulfamoyl, N,N-diethylsulfamoyl, N,N-dipropylsulfamoyl, N,N-dibutylsulfamoyl, etc.), $C_{1-6}$ alkylthio (e.g., methylthio, ethylthio, propylthio, isopropylthio, butylthio, sec-butylthio, tert-butylthio, etc.), $C_{6-10}$ arylthio (e.g., phenylthio, naphthylthio, etc.), $C_{1-6}$ alkylsulfinyl (e.g., methylsulfinyl, ethylsulfinyl, propylsulfinyl, butylsulfinyl, etc.), $C_{6-10}$ arylsulfinyl (e.g., phenylsulfinyl, naphthylsulfinyl, etc.), $C_{1-6}$ alkylsulfonyl (e.g., methylsulfonyl, ethylsulfonyl, propylsulfonyl, butylsulfonyl, etc.), $C_{6-10}$ arylsulfonyl (e.g., phenylsulfonyl, naphthylsulfonyl, etc.), etc.

Ring A, that is, the partial structure of the formula (I):

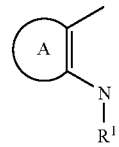

is preferably a ring represented by the formula

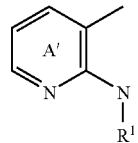

wherein symbols as defined above, that is, a pyridine ring represented by the formula

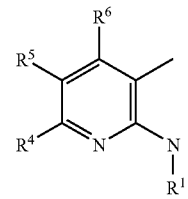

wherein $R^4$, $R^5$ and $R^6$ each independently represent, a hydrogen atom or those exemplified as the "substituent" of the "optionally substituted pyridine ring" represented by Ring A or Ring A or Ring A', more preferably those in which $R^4$ and $R^6$ is a $C_{1-4}$ alkyl group (e.g., methyl, ethyl, etc.) or a mono-, di- or tri-halogeno-$C_{1-4}$ alkyl group (e.g., trifluoromethyl, etc.), and $R^5$ is a hydrogen atom.

The "electron-attracting group" represented by X includes a nitrile group, a mono-, di- or tri-halogeno-$C_{1-4}$ alkyl group (e.g., trifluoromethyl, etc.), a halogen atom (e.g., fluorine, etc.), a $C_{1-4}$ alkoxy-carbonyl group (e.g., methoxycarbonyl, etc.), etc. X is preferably a nitrile group.

The "divalent $C_{1-6}$ chained hydrocarbon group" of the "optionally substituted divalent $C_{1-6}$ chained hydrocarbon group" represented by Y includes a $C_{1-6}$ alkylene group (e.g., —CH$_2$—, —(CH$_2$)$_2$—, —(CH$_2$)$_3$—, —(CH$_2$)$_4$—, —(CH$_2$)$_5$—, —(CH$_2$)$_6$—, —CH(CH$_3$)—CH$_2$—, etc.); a $C_{2-6}$ alkenylene group (e.g., —CH=CH—, —CH$_2$—CH=CH—, —CH=CH—CH$_2$—, —CH=CH—CH$_2$—CH$_2$—, —CH=CH—CH=CH—, —CH=CH—CH$_2$—CH$_2$—CH$_2$—, etc.); and a $C_{2-6}$ alkynylene group (e.g., —C≡C—, —CH$_2$—C≡C—, —CH$_2$—C≡C—CH$_2$—C≡C—, etc.)

The "substituent" of the "optionally substituted divalent $C_{1-6}$ chained hydrocarbon group" represented by Y includes, for example, the same groups as those exemplified with respect to the above-described "substituent" of the "optionally substituted pyridine ring" represented by Ring A or Ring A'. The number of the substituents is 1 to 4. The substituent is preferably a halogen atom (e.g., fluorine, chlorine, bromine, iodine, etc.), a mono-, di- or tri-halogeno-$C_{1-4}$ alkyl group (e.g., trifluoromethyl, etc.), a $C_{1-4}$ alkoxy group (e.g., methoxy, ethoxy, etc.), etc.

Y is preferably —CH=CH— or —(CH$_2$)$_2$—, more preferably —CH=CH—.

The "hydrocarbon group" of the "optionally substituted hydrocarbon group" represented by $R^1$, $R^2$ and $R^3$ includes, for example, aliphatic hydrocarbon group, alicyclic hydrocarbon group, alicyclic-aliphatic hydrocarbon group and aromatic hydrocarbon group, etc., preferably those having carbon number of 1 to 16. Specifically, for example, alkyl, alkenyl, alkynyl, cycloalkyl, cycloalkenyl, cycloalkylalkyl, cycloalkenylalkyl, aryl and aralkyl, etc. are used.

The "alkyl" is preferably, for example, lower alkyl, etc., and for example, $C_{1-6}$ alkyl such as methyl, ethyl, propyl, isopropyl, butyl, isobutyl, sec-butyl, tert-butyl, pentyl, 1-ethylpropyl and hexyl, etc. are used.

The "alkenyl" is preferably, for example, lower alkenyl, etc., and for example, $C_{2-7}$ alkenyl such as vinyl, 1-propenyl, allyl, isopropenyl, butenyl, isobutenyl and 2,2-dimethylpento-4-enyl, etc. are used.

The "alkynyl" is preferably, for example, lower alkynyl, etc., and for example, $C_{2-6}$ alkynyl such as ethynyl, propargyl and 1-propynyl, etc. are used.

The "cycloalkyl" is preferably, for example, lower cycloalkyl, etc., and for example, $C_{3-10}$ cycloalkyl such as cyclopropyl, cyclobutyl, cyclopentyl cyclohexyl, cycloheptyl, cyclooctyl, bicyclo[2.2.1]heptanyl and adamantyl, etc. are used.

The "cycloalkenyl" is preferably, for example, lower cycloalkenyl, and for example, $C_{3-6}$ cycloalkenyl such as cyclopropenyl, cyclobutenyl, cyclopentenyl, cyclohexenyl, etc. are used.

The "cycloalkylalkyl" is preferably, for example, lower cycloalkylalkyl, and for example, $C_{4-12}$ cycloalkylalkyl such as cyclopropylmethyl, cyclopropylethyl, cyclobutylmethyl, cyclopentylmethyl, cyclohexylmethyl and cyclohexylethyl, etc. are used.

The "cycloalkenylalkyl" is preferably, for example, lower cycloalkenylalkyl group, and for example, $C_{4-12}$ cycloalkenylalkyl such as cyclopentenylmethyl, cyclohexenylmethyl, cyclohexenylethyl, cyclohexenylpropyl, cycloheptenylmethyl, cycloheptenylethyl and bicyclo[2.2.1]hepto-5-en-2-ylmethyl, etc. are used The "aryl" is, for example, $C_{6-14}$ aryl such as phenyl, 1-naphthyl, 2-naphthyl, biphenylyl and 2-anthryl, etc., and phenyl, etc. is preferred.

The "aralkyl" is, for example, a $C_{7-19}$ aralkyl group such as benzyl, naphthylethyl, benzhydryl, trityl, etc., and benzyl, benzhydryl, etc. are preferred.

Furthermore, the "hydrocarbon group" of the "optionally substituted hydrocarbon group" represented by $R^1$, $R^2$ and $R^3$ includes a group formed by fusion of the cycloalkyl group of the "cycloalkyl" or the "cycloalkylalkyl" mentioned above with a benzene ring (e.g., a polycyclic hydrocarbon group such as 1,2,3,4-tetrahydro-1-naphthalenyl, 2,3-dihydro-1H-inden-1-yl, 2,3-dihydro-1H-inden-2-yl, etc.).

The "substituent" of the "optionally substituted hydrocarbon group" represented by $R^1$, $R^2$ and $R^3$ includes, for example, the same groups as those exemplified with respect to the above-described "substituent" of the "optionally substituted pyridine ring" represented by Ring A or Ring A'. The number of the substituents is 1 to 4.

The "heterocyclic group" of the "optionally substituted heterocyclic group" represented by $R^2$ and $R^3$ includes, for example, a 5- to 14-membered (preferably 5- to 10-membered) (mono- to tri-cyclic, preferably mono- or bi-cyclic) heterocyclic group containing 1 to 4 (preferably 1 to 3) hetero atoms selected from a nitrogen atom, an oxygen atom and a sulfur atom in addition to carbon atoms, etc. For example, a 5-membered cyclic group containing 1 to 4 hetero atoms selected from an oxygen atom, a sulfur atom and a nitrogen atom in addition to carbon atoms such as 2- or 3-thienyl, 2- or 3-furyl, 1-, 2- or 3-pyrrolyl, 1-, 2- or 3-pyrrolidinyl, 2-, 4- or 5-oxazolyl, 3-, 4- or 5-isoxazolyl, 2-, 4- or 5-thiazolyl, 3-, 4- or 5-isothiazolyl, 3-, 4- or 5-pyrazolyl, 2-, 3- or 4-pyrazolidinyl, 2-, 4- or 5-imidazolyl, 1,2,3-triazolyl, 1,2,4-triazolyl, 1H- or 2H-tetrazolyl, etc., a 6-membered cyclic group containing 1 to 4 hetero atoms selected from an oxygen atom, a sulfur atom and a nitrogen atom in addition to carbon atoms such as 2-, 3- or 4-pyridyl, N-oxide-2-, 3- or 4-pyridyl, 2-, 4- or 5-pyrimidinyl, N-oxide-2 -, 4- or 5-pyrimidinyl, thiomorpholinyl, morpholinyl, piperidino, 2-, 3- or 4-piperidyl, tetrahydropyranyl, thiopyranyl, 1,4-oxazinyl, 1,4-thiazinyl, 1,3-thiazinyl, piperazinyl, triazinyl, 3- or 4-pyridazinyl, pyrazinyl, N-oxide-3- or 4-pyridazinyl, etc., a bi- or tri-cyclic fused cyclic group containing 1 to 4 hetero atoms selected from an oxygen atom, a sulfur atom and a nitrogen atom in addition to carbon atoms (preferably, a group formed by fusion of the above-mentioned 5- or 6-membered ring with one or two 5- or 6-membered cyclic groups optionally containing 1 to 4 hetero atoms selected from an oxygen atom, a sulfur atom and a nitrogen atom in addition to carbon atoms) such as indolyl, benzofuryl, benzothiazolyl, benzoxazolyl, benzimidazolyl, quinolyl, isoquinolyl, phthalazinyl, quinazolinyl, quinoxalinyl, indolizinyl, quinolizinyl, 1,8-naphthyridinyl, dibenzofuranyl, carbazolyl, acridinyl, phenanthridinyl, chromanyl, phenothiazinyl, phenoxazinyl, etc. are used. Among these, preferred is a 5- to 7-membered (preferably 5- or 6-membered) heterocyclic group containing 1 to 3 hetero atoms selected from an oxygen atom, a sulfur atom and a nitrogen atom in addition to carbon atoms.

The "substituent" of the "optionally substituted heterocyclic group" represented by $R^2$ and $R^3$ includes, for example, the same groups as those exemplified with respect to the above-described "substituent" of the "optionally substituted pyridyl group" represented by Ring A or Ring A', etc.

The "heterocyclic group" of the "optionally substituted heterocyclic group" represented by $R^2$ and $R^3$ may contain 1 to 5, preferably 1 to 3 of the above-mentioned substituents at the substitutable positions of the heterocyclic group, respectively. If the number of substituents is 2 or more, each substituent may be the same or different.

The ring formed by $R^2$ and $R^3$ together with an adjacent nitrogen atom includes, for example, a 3- to 8-membered (preferably 5- or 6-membered) nitrogen-containing heterocyclic ring optionally containing 1 to 3 hetero atoms selected from an oxygen atom, a sulfur atom and a nitrogen atom in addition to carbon atoms and one nitrogen atom, etc. (e.g., aziridine, azetidine, pyrrolidine, pyrroline, pyrrole, imidazole, pyrazoline, imidazolidine, piperidine, morpholine, thiomorpholine, dihydropyridine, pyridine, piperazine, etc.). The ring may have 1 to 4 substituents similar to the above-described "substituent" of the "optionally substituted pyridine ring" represented by Ring A or Ring A'.

$R^1$ is preferably (1) a $C_{5-7}$ cycloalkyl group optionally fused with a benzene ring (e.g., tetrahydronaphthalenyl, indanyl, etc.), (2) a $C_{7-19}$ aralkyl group (e.g., benzyl, benzhydryl, etc.), (3) a 5- or 6-membered heterocyclic ring-$C_{1-4}$ alkyl group (e.g., a 5- or 6-membered aromatic or non-aromatic heterocyclic ring-$C_{1-4}$ alkyl group containing 1 to 3 hetero atoms selected from an oxygen atom, a sulfur atom and a nitrogen atom in addition to carbon atoms such as 2-thienylmethyl, 3-pyridylmethyl, tetrahydro-2-furanylmethyl, etc.) or (4) a $C_{6-14}$ aryloxy-$C_{1-4}$ alkyl group (e.g., 2-phenoxyethyl, etc.), each of which may have 1 to 4 (preferably 1 or 2) substituents selected from a halogen atom (e.g., fluorine, chlorine, bromine, iodine, etc.), a $C_{1-4}$ alkyl group (e.g., methyl, ethyl, etc.), a mono-, di- or tri-halogeno-$C_{1-4}$ alkyl group (e.g., trifluoromethyl, etc.) and a $C_{1-4}$ alkoxy group (e.g., methoxy, ethoxy, etc.) (Substituent group A), etc. Furthermore, the substituent group A may be substituted at either the ring moiety such as the benzene ring, the heterocyclic ring, etc. or the alkyl moiety of the groups of (1) to (4).

$R^1$ is more preferably a $C_{5-7}$ cycloalkyl group which may fused with a benzene ring and may be substituted with one or two $C_{1-4}$ alkoxy groups (e.g., tetrahydronaphthalenyl, indanyl, etc.) and most preferably, tetrahydronaphthalenyl.

One of $R^2$ and $R^3$ is preferably a hydrogen atom or a $C_{1-4}$ alkyl group (e.g., methyl, ethyl, etc.), and the other is preferably a 5- or 6-membered heterocyclic group (e.g., a 5- or 6-membered aromatic or non-aromatic heterocyclic group containing 1 to 3 hetero atoms selected from an oxygen atom, a sulfur atom and a nitrogen atom in addition to carbon atoms such as tetrahydropyranyl, pyridyl, etc.), a $C_{6-14}$ aryl group (e.g., phenyl, etc.), a $C_{7-19}$ aralkyl group (e.g., benzyl, etc.), a $C_{3-10}$ cycloalkyl group (e.g., cyclohexyl, etc.), a 5- or 6-membered heterocyclic ring-$C_{1-4}$ alkyl group (e.g., a 5- or 6-membered aromatic or non-aromatic heterocyclic group containing 1 to 3 hetero atoms selected from an oxygen atom, a sulfur atom and a nitrogen atom in addition to carbon atoms such as pyridylmethyl, etc.) or a $C_{1-6}$ alkyl group (e.g., methyl, ethyl, propyl, isopropyl, butyl, isobutyl, sec-butyl, tert-butyl, pentyl, 1-ethylpropyl, hexyl, etc.), etc., each of which may have 1 to 4 (preferably 1 or 2) substituents selected from a halogen atom (e.g., fluorine, chlorine, bromine, iodine, etc.), a $C_{1-4}$ alkyl group (e.g., methyl, ethyl, etc.), a mono-, di- or tri-halogeno-$C_{1-4}$ alkyl group (e.g., trifluoromethyl, etc.), a $C_{1-4}$ alkoxy group (e.g., methoxy, ethoxy, etc.), a $C_{1-4}$ alkoxy-carbonyl group (e.g., methoxycarbonyl, ethoxycarbonyl, etc.), a cyano group, a $C_{1-4}$ alkyl-carbonylamino group (e.g., methylcarbonylamino, etc.), a hydroxy group, etc. Alternatively, $R^2$ and $R^3$, together with an adjacent nitrogen atom, preferably form a 5- or 6-membered nitrogen-containing heterocyclic ring optionally containing 1 to 3 hetero atoms selected from an oxygen atom, a sulfur atom and a nitrogen atom in addition to carbon atoms and one nitrogen (e.g., morpholine, thiomorpholine, etc.), in which the nitrogen-containing heterocyclic ring may have 1 to 4 (preferably 1 or 2) substituents selected from a halogen atom (e.g., fluorine, chlorine, bromine, iodine, etc.), a $C_{1-4}$ alkyl group (e.g., methyl, ethyl, etc.), a mono-, di- or tri-halogeno-$C_{1-4}$ alkyl group (e.g., trifluoromethyl, etc.), a $C_{1-4}$ alkoxy group (e.g., methoxy, ethoxy, etc.), a $C_{1-4}$ alkoxy-carbonyl group (e.g., methoxycarbonyl, ethoxycarbonyl, etc.), etc.

More preferably, one of $R^2$ and $R^3$ is, for example, a hydrogen atom or a $C_{1-4}$ alkyl group, and the other is a $C_{6-14}$ aryl group (e.g., phenyl, etc.) which may have 1 to 2 substituents selected from a halogen atom, a $C_{1-4}$ alkyl group, a mono-, di- or tri-halogeno-$C_{1-4}$ alkyl group, a $C_{1-4}$ alkoxy group, a $C_{1-4}$ alkoxy-carbonyl group, a cyano group, a $C_{1-4}$ alkyl-carbonylamino group and a hydroxy group.

The compound represented by the formula (I) is preferably those in which Ring A is a ring represented by the formula

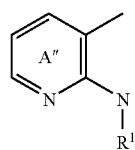

wherein Ring A" represents a pyridine ring which may have 1 to 3 (preferably 1 or 2) substituents selected from a $C_{1-4}$ alkyl group and a mono-, di- or tri-halogeno-$C_{1-4}$ alkyl group, X is a nitrile group, Y is —CH=CH— or —(CH$_2$)$_2$—, $R^1$ is (1) a $C_{5-7}$ cycloalkyl group optionally fused with a benzene ring, (2) a $C_{7-19}$ aralkyl group, (3) a 5- or 6-membered heterocyclic ring-$C_{1-4}$ alkyl group (e.g., a 5- or 6-membered aromatic or non-aromatic heterocyclic ring-$C_{1-4}$ alkyl group containing 1 to 3 hetero atoms selected from an oxygen atom, a sulfur atom and a nitrogen atom in addition to carbon atoms such as 2-thienylmethyl, 3-pyridylmethyl, tetrahydro-2-furanylmethyl, etc.) or (4) a $C_{6-14}$ aryloxy-$C_{1-4}$ alkyl group, each of which may have 1 to 4 (preferably 1 or 2) substituents selected from a halogen atom, a $C_{1-4}$ alkyl group, a mono-, di- or tri-halogeno-Cl$_4$ alkyl group and a $C_{1-4}$ alkoxy group, one of $R^2$ and $R^3$ is a hydrogen atom or a $C_{1-4}$ alkyl group, and the other is a 5- or 6-membered heterocyclic group (e.g., a 5- or 6-membered aromatic or non-aromatic heterocyclic group containing 1 to 3 hetero atoms selected from an oxygen atom, a sulfur atom and a nitrogen atom in addition to carbon atoms such as tetrahydropyranyl, pyridyl, etc.), a $C_{6-14}$ aryl group, a $C_{7-19}$ aralkyl group, a $C_{3-10}$ cycloalkyl group, a 5- or 6-membered heterocyclic ring-$C_{1-4}$ alkyl group (e.g., a 5- or 6-membered aromatic or non-aromatic heterocyclic group containing 1 to 3 hetero atoms selected from an oxygen atom, a sulfur atom and a nitrogen atom in addition to carbon atoms such as pyridylmethyl, etc.) or a $C_{1-6}$ alkyl group, each of which may have 1 to 4 (preferably 1 or 2) substituents selected from a halogen atom, a $C_{1-4}$ alkyl group, a mono-, di- or tri-halogeno-$C_{1-4}$ alkyl group, a $C_{1-4}$ alkoxy group, a $C_{1-4}$ alkoxy-carbonyl group, a cyano group, a $C_{1-4}$ alkyl-carbonylamino group and a hydroxy group; or $R^2$ and $R^3$ together with an adjacent nitrogen atom, form a 5- or 6-membered nitrogen-containing heterocyclic ring optionally containing 1 to 3 hetero atoms selected from an oxygen atom, a sulfur atom and a nitrogen atom in addition to carbon atoms and one nitrogen atom (e.g., morpholine, thiomorpholine, etc.), in which the nitrogen-containing heterocyclic ring may have 1 to 4 (preferably 1 or 2) substituents selected from a halogen atom, a $C_{1-4}$ alkyl group, a mono-, di- or tri-halogeno-$C_{1-4}$ alkyl group, a $C_{1-4}$ alkoxy group and a $C_{1-4}$ alkoxy-carbonyl group.

Examples of the salts of the compound of the present invention represented by the formula (I) and a synthetic intermediate thereof include, for example, an acid addition salt such as an inorganic acid salt (e.g., hydrochloride, sulfate, hydrobromide, phosphate, etc.), an organic acid salt (e.g., acetate, trifluoroacetate, succinate, maleate, fumarate, propionate, citrate, tartarate, lactate, oxalate, methanesulfonate, benzensulfonate, p-toluenesulfonate, etc.), as well as a salt with a base such as an alkali metal salt (e.g., a potassium salt, a sodium salt, a lithium salt, etc.), an alkaline earth metal salt (e.g. a calcium salt, a magnesium salt, etc.), a salt with an organic base (e.g., an ammonium salt, a trimethylamine salt, a triethylamine salt, a tert-butyldimethylamine salt, a dibenzylmethylamine salt, a benzyldimethylamine salt, an N,N-dimethylaniline salt, a pyridine salt, a quinoline salt), etc. Among others, a pharmaceutically acceptable salt is preferable.

Furthermore, the compound represented by the formula (I) or a salt thereof may be a hydrate or a solvate. Hereinafter, Compound (I) refers to those including a salt, a hydrate and a solvate thereof, respectively.

A prodrug of Compound (I) refers to a compound which is converted into Compound (I) by a reaction with an enzyme, gastric acid or the like in vivo.

Examples of the prodrug of Compound (I) include a compound in which in the case where Compound (I) contains an amino group, the amino group of Compound (I) is acylated, alkylated or phosphorylated (e.g., a compound in which the amino group of Compound (I) is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated, or tert-butylated); a compound in which in the case where Compound (I) contains a hydroxy group, the hydroxy group of Compound (I) is acylated, alkylated, phosphorylated or converted into borate (e.g. a compound in which the hydroxy group of Compound (I) is acetylated, palmitoylated, propanoylated, pivaloylated, succinylated, fumarylated, alanylated or dimethylaminomethylcarbonylated); a compound in which in the case where Compound (I) contains a carboxyl group, the carboxyl group of Compound (I) is esterified or amidated (e.g. a compound in which the carboxyl group of Compound (I) is ethyl esterified, phenyl esterified, carboxymethyl esterified, dimethylaminomethyl esterified, pivaloyloxymethyl esterified, ethoxycarbonyloxyethyl esterified, phthalidyl esterified, (5-methyl-2-oxo-1,3-dioxolen-4-yl)methyl esterified, cyclohexyloxycarbonylethyl esterified or methylamidated, etc.); etc. These compounds can be prepared by a known method per se. Furthermore, the prodrug of Compound (I) may be a compound which is converted into Compound (I) under physiological conditions as described in "Development of Drugs", Vol. 7, Molecular Design, Hirokawa Shoten, 1990; pp. 163-198.

The prodrug of Compound (I) may be itself or a pharmaceutically acceptable salt thereof. In the case where the prodrug of Compound (I) has an acidic group such as a carboxyl group, etc., examples of these salts include salts with an inorganic base (e.g., an alkali metal.such as sodium, potassium, etc., an alkaline earth metal such as calcium, magnesium, etc. and a transition metal such as zin c, iron, copper, etc.), and salts with an organic base (e.g., organic amines such as trimethylamine, triethylamine, pyridine, picoline, ethanolamine, diethanolamine, triethanolamine, dicyclohexylamine, N,N'-dibenzylethylenediamine, etc. and basic amino acids such as arginine, lysine, ornithine, etc.)).

In the case where the prodrug of Compound (I) has a basic group such as an amino group, etc., examples of the salts include salts with an inorganic acid or organic acid (e.g., hydrochloric acid, nitric acid, sulfuric acid, phosphoric acid, carbonic acid, bicarbonic acid, formic acid, acetic acid, propionic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, etc.) and an acidic amino acid such as aspartic acid, glutamic acid, etc.

Furthermore, the prodrug of Compound (I) may be a hydrate or a non-hydrate.

The compound (I) may contain one or more asymmetric carbon atoms in the molecule and the compounds having any one of R configuration and S configuration relating to the asymmetric carbon atoms are included in the scope of the present invention.

Compound (I) of the present invention can be prepared by, for example, Production Method 1 or modifications thereof.

[Production Method 1]

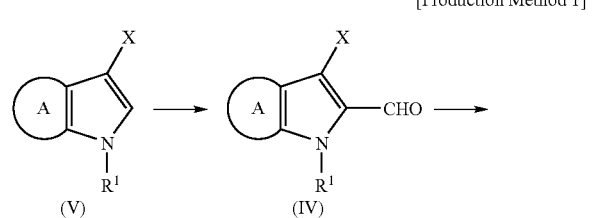

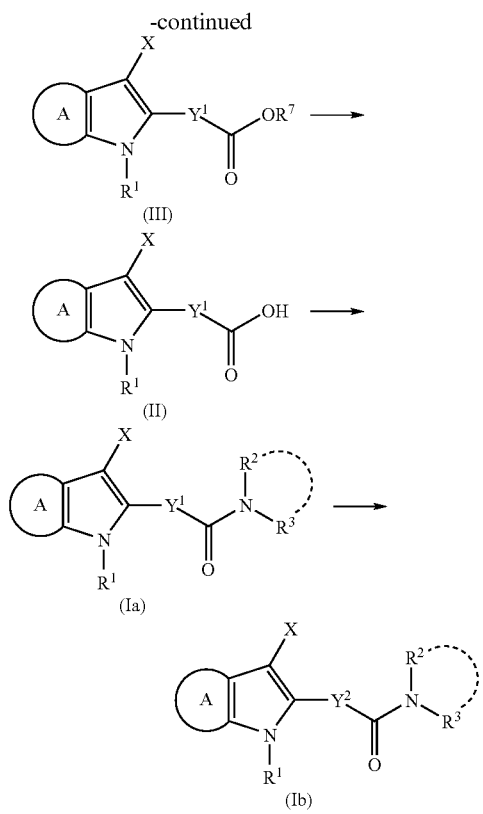

wherein $R^7$ is each an optionally substituted hydrocarbon group or heterocyclic group, $Y^1$ is each an optionally substituted $C_{2-6}$ alkenylene group or $C_{2-6}$ alkynylene group, $Y^2$ is an optionally substituted $C_{1-6}$ alkylene group and other symbols are as defined above The "optionally substituted hydrocarbon group" represented by $R^7$ includes the same groups as those exemplified with respect to the above-described "optionally substituted hydrocarbon group" represented by $R^2$ and $R^3$.

The "optionally substituted heterocyclic group" represented by $R^7$ includes the same groups as those exemplified with respect to the above-described "optionally substituted heterocyclic group" represented by $R^2$ and $R^3$.

The "substituent" of the "each optionally substituted $C_{2-6}$ alkenylene group or $C_{2-6}$ alkynylene group" represented by $Y^1$ and the "optionally substituted $C_{1-6}$ alkylene group" represented by $Y^2$ includes the same groups as those exemplified with respect to the above-described "substituent" of the "optionally substituted divalent $C_{1-6}$ chained hydrocarbon group" represented by Y.

According to Production Method 1, first, Compound (V) is subjected to formylation reaction to produce Compound (IV).

The formylation reaction is carried out in a solvent having no influence on the reaction in the presence of a base and a formylation agent according to a conventional method. The base includes lithium diisopropylamide, n-butyl lithium, sec-butyl lithium, tert-butyl lithium, etc.

The formylation agent includes N,N-dimethylformamide, N-formylpiperidine, N-formylmorpholine, N-formyl-N-methylaniline, etc.

The amount of the base and the formylation agent is preferably about 1 to about 5 molar equivalents, relative to Compound (V), respectively.

The solvent having no influence on the reaction includes, for example, ethers such as ether and tetrahydrofuran; aromatic hydrocarbons such as benzene; hydrocarbons such as hexane, etc. The amount of these solvents is, for example, 1 to 100 times by volume, relative to Compound (V).

The reaction temperature is usually about −100 to 100° C., preferably −80 to 25° C.

The reaction time is usually about 0.1 to about 24 hours.

Thus obtained Compound (IV) can be isolated and purified by known isolation and purification means, for example, concentration, concentration under reduced pressure, solvent extraction, crystallization, recrystallization, solvent convert, chromatography, etc.

Furthermore, Compound (IV) may be used in the next reaction without isolation.

Then, Compound (IV) is subjected to Wittig reaction to produce Compound (III). The Wittig reaction is carried out in a solvent having no influence on the reaction in the presence of a base and a phosphorus reagent according to a conventional method. The base includes sodium hydride, n-butyl lithium, bis(trimethylsilyl)amide lithium, potassium carbonate, sodium hydroxide, sodium carbonate, sodium ethoxide, triethylamine, pyridine, tert-butoxy potassium, etc.

The phosphorus reagent includes triethyl phosphonoacetate, trimethyl phosphonoacetate, (2-methoxy-2-oxoethyl) (triphenyl)phosphonium bromide, (2-ethoxy-2-oxoethyl) (triphenyl)phosphonium bromide, (2-ethoxy-1-iodo-2-oxoethyl) (triphenyl)phosphonium iodide, etc.

The amount of the base and the phosphorus reagent is preferably about 1 to about 5 molar equivalents, relative to Compound (IV), respectively.

The solvent having no influence on the reaction includes, for example, ethers such as ether and tetrahydrofuran; aromatic hydrocarbons such as benzene; hydrocarbons such as hexane; amides such as N,N-dimethylformamide; and sulfoxides such as dimethylsulfoxide; alcohols such as ethanol, etc. The amount of these solvents is, for example, 1 to 100 times by volume, relative to Compound (V).

The reaction temperature is usually about −100 to 250° C., preferably 0 to 125° C.

The reaction time is usually about 0.1 to about 24 hours.

Thus obtained Compound (IV) can be isolated and purified by known isolation and purification means, for example, concentration, concentration under reduced pressure, solvent extraction, crystallization, recrystallization, solvent convert, chromatography, etc.

Furthermore, Compound (III) may be used in the next reaction without isolation.

Then, Compound (III) is subjected to hydrolysis reaction to produce Compound (II).

The hydrolysis reaction is carried out in a solvent having no influence on the reaction in the presence of a base according to a conventional method. The base includes sodium hydroxide, potassium hydroxide, lithium hydroxide, potassium carbonate, sodium carbonate, sodium ethoxide, tert-butoxy potassium, etc.

The amount of the base is preferably about 1 to about 5 molar equivalents, relative to Compound (IV), respectively.

The solvent having no influence on the reaction includes, for example, ethers such as ether and tetrahydrofuran; aromatic hydrocarbons such as benzene; hydrocarbons such as hexane; amides such as N,N-dimethylformamide; sulfoxides such as dimethylsulfoxide; alcohols such as ethanol, etc. The amount of these solvents is, for example, 1 to 100 times by volume, relative to Compound (V).

The reaction temperature is usually about −100 to 250° C., preferably 0 to 125° C.

The reaction time is usually about 0.1 to about 24 hours.

Thus obtained Compound (IV) can be isolated and purified by known isolation and purification means, for example, concentration, concentration under reduced pressure, solvent extraction, crystallization, recrystallization, solvent convert, chromatography, etc.

Furthermore, Compound (II) may be used in the next reaction without isolation.

Then, Compound (II) is subjected to amidation reaction, that is, compound (II) is subjected to reaction with a compound represented by the formula

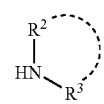

wherein symbols as defined above, or a salt thereof to produce Compound (Ia).

The amidation reaction is carried out in a solvent having no influence on the reaction in the presence of a base, an acid activator and suitable amine according to a conventional method.

The acid activator includes oxalyl chloride, thionyl chloride, N,N-dicyclohexylcarbodiimide, 1-ethyl-3-(3-dimethylaminopropyl)carbodiimide hydrochloride, chloroethyl carbonate, chloroethylisopropyl carbonate, carbodiimidazole, etc.

The base includes potassium carbonate, sodium hydroxide, potassium hydroxide, lithium hydroxide, sodium carbonate, sodium hydrocarbonate, triethylamine, diisopropylethylamine, pyridine, 4-dimethylaminopyridine, etc.

The amount of the base, the acid activator and the suitable amine is preferably about 1 to about 5 molar equivalents, relative to Compound (II), respectively.

The solvent having no influence. on the reaction includes, for example, ethers such as ether and tetrahydrofuran; aromatic hydrocarbons such as benzene; hydrocarbons such as hexane; amides such as N,N-dimethylformamide; sulfoxides such as dimethylsulfoxide, etc. The amount of these solvents is, for example, 1 to 100 times by volume, relative to Compound (V).

The reaction temperature is usually about −100 to 250° C., preferably −20 to 125° C.

The reaction time is usually about 0.1 to about 24 hours.

Thus obtained Compound (Ia) can be isolated and purified by known isolation and purification means, for example, concentration, concentration under reduced pressure, solvent extraction, crystallization, recrystallization, solvent convert, chromatography, etc.

Then, if desired, Compound (Ia) is subjected to reduction reaction to produce Compound (Ib).

The reduction reaction is carried out in a solvent having no influence on the reaction in the presence of hydrogen and a catalyst according to a conventional method.

The catalyst includes palladium carbon, palladium hydroxide, platinum oxide, a Wilkinson's complex, etc. The amount of the catalyst is preferably about 0.1 to about 2 molar equivalents, relative to Compound (Ia), respectively.

The solvent having no influence on the reaction includes, for example, ethers such as ether and tetrahydrofuran; aromatic hydrocarbons such as benzene; hydrocarbons such as hexane; amides such as N,N-dimethylformamide; sulfoxides such as dimethylsulfoxide; alcohols such as ethanol, etc. The amount of these solvents is, for example, 1 to 100 times by volume, relative to Compound (Ia).

The reaction temperature is usually about −5 to 250° C., preferably 0 to 125° C.

A compound represented by the formula

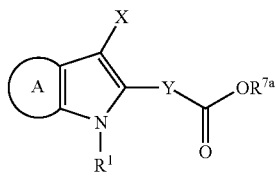

wherein $R^{7a}$ is a hydrogen atom, an optionally substituted hydrocarbon group or an optionally substituted heterocyclic group, and other symbols are as defined above, or a salt thereof, which is an intermediate in the synthesis of Compound (I), is a novel compound.

The "optionally substituted hydrocarbon group or optionally substituted heterocyclic group" represented by $R^{7a}$ includes the same groups as those represented by $R^7$.

Compound (V) used as a starting compound can be prepared by a known method per se, for example, the method described in Journal of Medicinal Chemistry, Vol. 42, pp. 819-832 (1999), Journal of the Chemical society, Perkin Transaction I, Vol. 19, pp. 1910-1913 (1975), Journal of the Chemical society, C, Vol. 3, pp 498-501 (1975), Comprehensive Heterocyclic Chemistry, Vol. 4, pp 497-529, etc., or modifications thereof.

Compound (I) of the present invention and a prodrug thereof have excellent vanilloid receptor agonistic actions. The vanilloid receptor is a nocireceptor which mediates pain, and an agonist thereof has the effect of desensitizing nerves.

Therefore, compound (I) of the present invention and a prodrug thereof having excellent vanilloid receptor agonistic actions, have analgesic actions and actions of preventing and/or treating urination disorders for a mammal (e.g., mouse, rat, hamster, rabbit, cat, dog, bovine, sheep, monkey, human, etc.), and a pharmaceutical composition comprising the same is useful as an analgesic and an agent for preventing and/or treating urination disorders, etc. That is, the pharmaceutical composition is useful for treating acute/chronic, systemic and topical pain and/or inflammation, for example, preventing and/or treating knee osteoarthritis, joint pain such as low back pain, arthritis deformans, chronic arthritic rheumatism, fibromyalgia, Guillain-Barre syndrome, meralgia paresthetica, pain by reflex sympathetic dystrophy, postoperative pain, diabetic neuropathy, herpes zoster pain, carcinomatous pain, migraine, myalgia, tooth pain, myocardiac infarction, reflex sympathetic nerve anomaly, pain by trigeminal neuralgia, postmastectomy pain; analgesia for pain, etc. by burns; preventing and/or treating pain by inflammatory gastrointestinal diseases and enterokinesis; treating allergic rhinitis and vasomotor rhinitis; treating atopic dermatitis, psoriasis, Lichen simplex chronicus, hemodialysis, itch by rash, etc.; preventing and/or treating urination disorders such as overactive bladder (e.g., frequent urination and/or urinary incontinence, etc.), etc. Furthermore, the pharmaceutical composition is useful for treating clamacteric disorders, or flush or glow by administration of gonadotrophin agonist; treating emesis by anti-emetic or anticancer drug; preventing obesity; a fat accumulation inhibitor (a fat metabolism enhancer); lowering cholesterol; an agent for enhancing secretion of adrenaline (increasing action of cardiac rate, etc.); reducing blood pressure; protecting gastric mucosa; promoting secretion of saliva or gastric juice; reducing blood glucose; treating irritable bowel syndrome; treating toxin shock, sepsis shock, atherosclerosis or cancer; preventing prognosis of nerve tissue degenerative disease such as cerebral apoplexy (cerebral infarction, cerebral hemorrhage); preventing and/or treating motor neuron diseases, a Parkinson's disease, an Alzheimer's disease, AIDS-associated dementia, a Lewy body disease, cranial nerve disorders, peripheral nerve disorders and prion disease.

Compound (I) of the present invention can be administered orally or parenterally, and can be provided for preventing and/or treating above-mentioned diseases by formulating it into preparations suitable for administration.

Compound (I) of the present invention can also be used in combination with a suitable amount of other drugs by appropriately compounding or combining them together. The other drugs include, for example, a diabetes treating agent, a diabetic complication treating agent, an antihyperlipidemic agent, a hypotensive agent, an anti-obesic, a diuretic, a chemotherapeutic agent, an immunotherapeutic agent, a cachexia improving agent, an anti-inflammatory agent, a glycosylation inhibitor, a neuranagenesis promoter, an anti-depressant, an anti-epileptic agent, an anti-arrhythmic agent, an acetylcholine receptor ligand, an endothelin receptor antagonist, a monoamine uptake inhibitor, an indoleamine uptake inhibitor, an opioid analgesic, a GABA receptor agonist, a GABA uptake inhibitor, an $\alpha_2$ receptor agonist, a local anesthesia, a protein kinase C inhibitor, an anxiolytic agent, a phosphodiesterase inhibitor, a dopamine receptor agonist and/or antagonist, a serotonin receptor agonist and antagonist, a serotonin uptake inhibitor, a hypnotic, an anti-cholinergic agent, an $\alpha_1$ receptor blocker, a muscle relaxant, a potassium channel opener, a calcium channel blocker, an Alzheimer's disease preventing and/or treating agent, a Parkinson's disease preventing and/or treating agent, a multiple sclerosis preventing and/or treating agent, a histamine $H_1$ receptor inhibitor, a proton pump inhibitor, an antithrombotic agent, an NK-2 receptor antagonist, a HIV infection treating agent, a chronic obstructive pulmonary disease treating agent, etc.

Compound (I) has low toxicity, and can be safely administered as it is or as mixed with a pharmacologically acceptable carrier according to a known method per se to be a pharmaceutical composition, for example, tablets (including sugar-coated tablet and a film-coated tablet), powders, granules, capsules (including soft capsules), liquid preparations, injections, nasal drops, suppositories, sustained-release preparations, patches, chewing gums, etc. orally or parenterally (e.g., locally (through the bladder, the urinary tract, etc.), rectally, intravenously, etc.). Among these, preparations for local administration are preferred.

The content of Compound (I) in the preparations of the present invention is from about 0.01% by weight to about 100% by weight based on the total weight of the preparations. The dose varies depending on the subject to be administered, the route for administration, diseases, etc. For example, in the case of oral administration for adult (50 kg body weight) as an analgesic, the daily dose of Compound (I) or Compound (Ia) as an active ingredient is about 5 mg to about 1000 mg, preferably about 10 to 600 mg, more preferably about 10 to 300 mg, and particularly preferably about 15 to 150 mg, and it can be administered once, or with being divided in 2 to 3 times per day.

When Compound (I) of the present invention may be used in combination with other drugs, these drugs, separately or simultaneously, may be formulated by mixing with pharmaceutically acceptable carriers, excipients, binders, diluents or the like to obtain a prophylactic and/or therapeutic pharmaceutical composition, which can be administered orally or parenterally. When the drug is prepared separately, the separately prepared drugs may be mixed with a diluent or the like before using and then administered, or each of the separately prepared preparations may be administered simultaneously or separately at an interval, to the same subject. Kit products for administering with mixing the separately prepared preparations with a diluent and the like before using (for example, an injection kit including ampoules containing each powdery drug, a diluent to be mixed and dissolved with 2 or more drugs before using, etc., and the like), kit products for administering each of the separately prepared preparations, simultaneously or separately at an interval, to the same person (for example, a tablet kit for administering 2 or more tablets simultaneously or separately at an interval, wherein the tablet containing each drugs was put into the same or the separate bags and, if necessary, a column wherein the drug administration date is to be indicated was provided on the bag), or the like are also included in the pharmaceutical composition of the present invention.

The pharmacologically acceptable carriers that can be used in the manufacture of a pharmaceutical composition of the present invention includes various kinds of organic or inorganic carriers which are conventionally used in pharmaceutical practice, such as an excipient, a lubricant, a binder and a disintegrator for solid preparations; or a solvent, a solubilizer, a suspending agent, an isotonizing agent, a buffer, and a soothing agent for liquid preparations. Further, additives such as common antiseptics, antioxidants, colorants, sweeteners, adsorbents, humectants, etc. can also be incorporated, if necessary.

The excipient includes, for example, lactose, sucrose, D-mannitol, starch, corn starch, crystalline cellulose, light silicic anhydride, etc.

The lubricant includes, for example, magnesium stearate, calcium stearate, talc, colloidal silica, etc.

The binder includes, for example, crystalline cellulose, sugar, D-mannitol, dextrin, hydroxypropylcellulose, hydroxypropylmethylcellulose, polyvinylpyrrolidone, starch, sucrose, gelatin, methylcellulose, carboxymethylcellulose sodium, etc.

The disintegrator includes, for example, starch, carboxymethylcellulose, carboxymethylcellulose calcium, croscarmellose sodium, carboxymethyl starch sodium, L-hydroxypropylcellulose, etc.

The solvent includes, for example, water for injection, alcohol, propylene glycol, macrogol, sesame oil, corn oil, olive oil, etc.

The solubilizer includes, for example, polyethylene glycol, propylene glycol, D-mannitol, benzyl benzoate, ethanol, trisaminomethane, cholesterol, triethanolamine, sodium carbonate, sodium citrate, etc.

The suspending agent includes, for example, surfactants such as stearyltriethanolamine, sodium lauryl sulfate, laurylaminopropionic acid, lecithin, benzalkonium chloride, benzethonium chloride, glyceryl monostearate, etc.; and hydrophilic macromolecular substances such as polyvinyl alcohol, polyvinylpyrrolidone, carboxymethylcellulose sodium, methylcellulose, hydroxymethylcellulose, hydroxyethylcellulose and hydroxypropylcellulose, etc.

The isotonizing agent includes, for example, glucose, D-sorbitol, sodium chloride, glycerin, D-mannitol, etc.

The buffer includes, for example, phosphate, acetate, carbonate, citrate, etc.

The soothing agent includes, for example, benzyl alcohol, etc.

The antiseptic includes, for example, p-hydroxybenzoic acid esters, chlorobutanol, benzyl alcohol, phenethyl alcohol, dehydroacetic acid, sorbic acid, etc.

The antioxidant includes, for example, sulfites, ascorbic acids, α-tocopherol, etc.

EXAMPLE

Further, the present invention is specifically explained through the following Examples and Experimental Examples, but these are merely practical examples and do not limit the present invention.

$^1$H-NMR spectrometry was measured with Varian Gemini200 (200 MHz) using tetramethylsilane as an internal standard. All of the δ values represent ppm. The numeric value indicated in the mixed solvent means a mixing ratio by volume unless otherwise stated. % means weight % unless otherwise stated. The eluting solvent in silica gel chromatography means a ratio by volume unless otherwise stated. Room temperature (normal temperature) in the present specification represents a temperature of about 20° C. to about 30° C.

LC-MS(Liquid chromatography mass spectrometry) was measured under the following conditions.

Measuring apparatus: ZMD (Micromass company)
Column: CAPCELL PAK UG-120 ODS (Shiseido)
Solvent: Liquid A; water containing 0.05% trifluoroacetic acid, Liquid B; acetonitrile containing 0.05% trifluoroacetic acid Gradient cycle: 0.00 min (Liquid A/Liquid B=90/10), 2.00 min (Liquid A/Liquid B=5/95), 2.75 min (Liquid A/Liquid B=5/95), 2.76 min (Liquid A/Liquid B=90/10), 3.45 min (Liquid A/Liquid B=90/10)

Injection amount: 2 ml, Flow rate: 0.5 ml/min, Detection method: UV 220 nm

Furthermore, HPLC was measured under the following conditions.

Measuring apparatus: Shimadzu Corporation LC-10 Avp system
Column: CAPCELLPAKCC18UG120, S-3 μm, 2.0×50 mm
Solvent: Liquid A (water containing 0.1% trifluoroacetic acid), Liquid B (acetonitrile containing 0.1% trifluoroacetic acid)

Gradient cycle: 0.00 min (Liquid A/Liquid B=90/10), 4.00 min (Liquid A/Liquid B=5/95), 5.50 min (Liquid A/Liquid B=5/95), 5.51 min (Liquid A/Liquid B=90/10), 8.00 min (Liquid A/Liquid B=90/10)

Flow rate: 0.5 ml/min

The abbreviations used in the Examples and Reference Examples mean as follows. s: singlet, d: doublet, t: triplet, q: quartet, br: broad, J: coupling constant, dd: double doublet, m: multiplet, Hz: Hertz, $CDCl_3$: deuterated chloroform, $DMSO-d_6$: deuterated dimethylsulfoxide, Me: methyl Reference Example 1

4,6-Dimethyl-1-(1,2,3,4-tetrahydro-1-naphthyl)-1H-pyrrolo[2,3-b]pyridine-3-carbonitrile To formyl succinonitrile potassium salt (10.5 g, 72 mmol) and 1,2,3,4-tetrahydro-1-naphthylamine (11.7 g, 79.2 mmol) was added water (30 ml), and acetic acid (30 ml) was added dropwise thereto over 10 minutes at room temperature with stirring. Then, the mixture was heated to 100° C., and stirred for 30 minutes. The reaction mixture was poured into ice-water (60 ml), made basic with adding potassium carbonate portionwise carefully, and distributed to ethyl acetate and saturated brine. The organic extract was washed with saturated brine and dried over anhydrous magnesium sulfate, and the solvent was removed under vacuum to yield a residue (16.3 g) as oily matter. To the residue were added tetrahydrofuran (75 ml) and ethanol (75 ml), to prepare a solution. Then, potassium ethoxide (11.1 g, 125 mmol) was added thereto over 5 minutes, and stirred for 1 hour at room temperature. After removing solvent under vacuum, the residue was distributed to ethyl acetate and water. The organic extract was washed with saturated brine and dried over anhydrous magnesium sulfate, and the solvent was removed under vacuum to yield a residue (15.2 g) as brownish powder. To the residue were added ethanol (250 ml), acetylacetone (6.9 ml, 67 mmol) and 12 N hydrochloric acid (3 ml), and the mixture was refluxed for 3 hours. After removing the solvent under vacuum, the residue was made basic with a saturated sodium hydrogen carbonate solution, and the product was extracted with ethyl acetate. The organic extract was washed with saturated brine and dried over anhydrous magnesium sulfate, and the solvent was removed under vacuum. To the residue was added ethyl acetate (30 ml), and the mixture was treated with ultrasonic wave for 10 minutes. The precipitate was collected by filtration with Kiriyama Roht, and washed with small amount of ethyl acetate to give the title compound (yield (amount) 5.3 g, yield (rate) 24%).

$^1$H-NMR (DMSO-$d_6$) δ: 1.88-1.99 (2H, m), 2.17-2.28 (2H, m), 2.56 (3H, s), 2.65 (3H, s), 2.75-3.02 (2H, m), 6.17 (1H, t, J=6.8 Hz), 6.54 (1H, d, J=7.4 Hz), 7.01-7.09 (2H, m), 7.17-7.23 (2H, m), 8.04 (1H, m)

The following compounds were synthesized in the same manner as in Reference Example 1.

Reference Example 2

1-(2,3-Dihydro-1H-inden-2-yl)-4,6-dimethyl-1H-pyrrolo[2,3-b]pyridine-3-carbonitrile Yield (amount) 5.6 g, yield (rate) 27% $^1$H-NMR (DMSO-$d_6$) δ: 2.54 (3H, s), 2.62 (3H, s), 2.29-3.36 (2H, m), 3.44-3.52 (2H, m), 5.64-5.69 (1H, m), 4.02 (1H, s), 7.21-7.32 (4H, m), 8.29 (1H, m)

Reference Example 3

1-(4,5-dimethoxy-2,3-dihydro-1H-inden-1-yl)-4,6-dimethyl-1H-pyrrolo[2,3-b]pyridine-3-carbonitrile Yield (amount) 1.4 g, yield (rate) 22% $^1$H-NMR (CDCl$_3$) δ: 2.05-2.22 (1H, m), 2.63 (3H, s), 2.71-2.88 (4H, m), 2.95-3.20 (2H, m), 3.89 (3H, s), 3.93 (3H, s), 6.43-6.50 (1H, m), 6.75-6.85 (2H, m), 6.91 (1H, s), 7.32 (1H, s)

Reference Example 4

1-(5,6-Dimethoxy-1,2,3,4-tetrahydro-1-naphthalenyl)-4,6-dimethyl-1H-pyrrolo[2,3-b]pyridine-3-carbonitrile Yield (amount) 2.2 g, yield (rate) 39% $^1$H-NMR (CDCl$_3$) δ: 1.70-1.91 (2H, m), 2.14-2.20 (2H, m), 2.63 (3H, s), 2.72-2.86 (4H, m), 2.93-3.01 (1H, m), 3.86 (3H, s), 3.87 (3H, s), 6.16 (1H, t, J=5.4 Hz), 6.58 (1H, d, J=9.0 Hz), 6.75 (1H, d, J=8.4 Hz), 6.91 (1H, s), 7.23 (1H, s)

Reference Example 5

1-(2,3-Dihydro-1H-inden-1-yl)-6-methyl-1H-pyrrolo[2,3-b]pyridine-3-carbonitrile

Yield (amount) 4.1 g, yield (rate) 20% $^1$H-NMR (CDCl$_3$) δ: 2.10-2.21 (1H, m), 2.70 (3H, s), 2.77-2.92 (1H, m), 3.05-3.17 (2H, m), 6.58 (1H, t, J=7.2 Hz), 7.06-7.41 (6H, m), 7.95 (1H, d, J=8.0 Hz)

Reference Example 6

1-(2,3-Dihydro-1H-inden-1-yl)-4,6-diethyl-1H-pyrrolo[2,3-b]pyridine-3-carbonitrile Yield (amount) 6.7 g, yield (rate) 29% $^1$H-NMR (CDCl$_3$) δ: 1.33-1.43 (6H, m), 2.08-2.25 (1H, m), 2.73-2.93 (3H, m), 2.97-3.17 (4H, m), 6.57 (1H, t, J=6.6 Hz), 6.97 (1H, s), 7.09 (1H, d, J=7.4 Hz), 7.19-7.40 (4H, m)

Reference Example 7

1-(2,3-Dihydro-1H-inden-1-yl)-4,6-diisopropyl-1H-pyrrolo[2,3-b]pyridine-3-carbonitrile Yield (amount) 9.6 g, yield (rate) 40% $^1$H-NMR (CDCl$_3$) δ: 1.34-1.42 (12H, m), 2.14-2.28 (1H, m), 2.75-2.89 (1H, m), 2.97-3.25 (3H, m), 3.71-3.85 (1H, m), 6.57 (1H, t, J=7.2 Hz), 7.03 (1H, s), 7.12 (1H, d, J=7.2 Hz), 7.19-7.40 (4H, m)

Example 1

(E)-3-[3-cyano-4,6-dimethyl-1-(1,2,3,4-tetrahydro-1-naphthalenyl)-1H-pyrrolo[2,3-b]pyridin-2-yl]-N-(2,2-dimethyltetrahydro-2H-pyran-4-yl)-2-propenamine (1) 4,6-Dimethyl-2-formyl-1-(1,2,3,4-tetrahydro-1-naphthalenyl)-1H-pyrrolo[2,3-b]pyridine-3-carbonitrile A 2 M solution (10 ml) of lithium diisopropylamide in heptane-THF-ethylbenzene was added to tetrahydrofuran (20 ml) under argon atmosphere, and the mixture was cooled to −78° C. in a dry ice-acetone bath. To the resultant solution was added dropwise over 30 minutes a solution of 4,6-dimethyl-1-(1,2,3,4-tetrahydro-1-naphthyl-1H-pyrrolo[2,3-b]pyridine-3-carbonitrile (3.0 g, 10 mmol) in tetrahydrofuran (30 ml), and after completion of the dropwise addition, the reaction mixture was stirred at −78° C. for 30 minutes. Next, DMF (3.1 ml, 40 mmol) was added thereto, the dry ice-acetone bath was removed, and then the mixture was stirred at room temperature for 2 hours. The reaction mixture was distributed to ethyl acetate and water. The organic extract was washed with saturated brine, dried over anhydrous magnesium sulfate, and the solvent was removed under vacuum. To the residue was added hexane, and the residue was finely crushed using a spatula. The solid material was collected by filtration and washed with hexane to give the title compound (yield (amount) 2.7 g, yield (rate) 82%).

$^1$H-NMR (CDCl$_3$) δ: 1.88-2.48 (4H, m), 2.60 (3H, s), 2.80 (3H, s), 2.86-3.04 (1H, m), 3.12-3.26 (1H, m), 6.33 (1H, d, J=7.6 Hz), 6.80-7.26 (5H, m), 9.89 (1H, s)

(2) Ethyl (E)-3-[3-cyano-4,6-dimethyl-1-(1,2,3,4-tetrahydro-1-naphthalenyl-1H-pyrrolo[2,3-b]pyridin-2-yl)-2-propenoate To a solution of 4,6-dimethyl-2-formyl-1-(1,2,3,4-tetrahydro-1-naphthalenyl)-1H-pyrrolo[2,3-b]pyridine-3-carbonitrile (2.65 g, 8.0 mmol) and ethyl diethylphosphonoacetate (1.84 g, 8.2 mmol) in DMF (30 ml), was added sodium hydride (oily) (328 mg, 8.2 mmol) under an ice bath. The ice bath was removed and the mixture was stirred at room temperature for 3 hours. Then, the reaction mixture was distributed to ethyl acetate and water. The organic extract was washed with saturated brine, dried over anhydrous magnesium sulfate, and the solvent was removed under vacuum. Ethyl acetate-hexane was added to the residue and the precipitated solid was collected by filtration using Kiriyama Roht to give the title compound (yield (amount) 1.5 g, yield (rate) 46%).

$^1$H-NMR (CDCl$_3$) δ: 1.26 (3H, t, J=7.2 Hz), 2.02-2.41 (4H, m), 2.60 (3H, s), 2.77 (3H, s), 2.88-3.09 (2H, m), 4.15 (2H, dd, J=7.2 Hz, 14.0 Hz), 6.54 (1H, d, J=7.8 Hz), 6.81-7.06 (4H, m), 7.13-7.27 (3H, m)

(3) (E)-3-[3-cyano-4,6-dimethyl-1-(1,2,3,4-tetrahydro-1-naphthalenyl)-1H-pyrrolo[2,3-b]pyridin-2-yl]-2-propenoic acid A solution of ethyl (E)-3-[3-cyano-4,6-dimethyl-1-(1,2,3,4-tetrahydro-1-naphthalenyl)-1H-pyrrolo[2,3-b]pyridin-2-yl]-2-propenoate (1.2 g, 3 mmol) in tetrahydrofuran (6 ml)-toluene (6 ml) was heated to 50° C. To the resultant solution was added a 2 N aqueous sodium hydroxide solution (4 ml, 8 mmol) and the mixture was stirred at 50° C. for 20 minutes. Then, water (100 ml) was added to the reaction mixture, which was adjusted to pH 3 to 4 with 12 N hydrochloric acid, and then the product was extracted using ethyl acetate-tetrahydrofuran (3:1, v/v). The organic extract was washed with saturated brine, dried over anhydrous magnesium sulfate, and the solvent was removed under vacuum. Hexane was added to the residue on a solid material and the residue was finely crushed using a spatula. The solid was collected by filtration using Kiriyama Roht and was washed with hexane to give the title compound (yield (amount) 1.0 g, yield (rate) 92%).
$^1$H-NMR (CDCl$_3$) δ: 2.05-2.19 (3H, m), 2.31-2.42 (1H, m), 2.60 (3H, s), 2.77 (3H, s), 2.91-3.10 (2H, m), 6.53 (1H, d, J=8.0 Hz), 6.79-7.06 (4H, m), 7.14-7.37 (3H, m)

(4) (E)-3-[3-cyano-4,6-dimethyl-1-(1,2,3,4-tetrahydro-1-naphthalenyl)-1H-pyrrolo[2,3-b]pyridin-2-yl]-N-(2,2-dimethyltetrahydro-2H-pyran-4-yl)-2-propenamide In the same manner described in (4) of Example 2, (E)-3-[3-cyano-4,6-dimethyl-1-(1,2,3,4-tetrahydro-1-naphthalenyl)-1H-pyrrolo[2,3-b]pyridin-2-yl]-N-(2,2-dimethyltetrahydro-2H-pyran-4-yl)-2-propenamide was synthesized from (E)-3-[3-cyano-4,6-dimethyl-1-(1,2,3,4-tetrahydro-1-naphthalenyl)-1H-pyrrolo[2,3-b]pyridin-2-yl]-2-propenoic acid and 2,2-dimethyltetrahydro-2H-pyran-4-ylamine.
Yield (amount) 21 mg LC-
MS(ESI-) analysis: Purity 90%, 483 (M+H) (retention time: 2.40 minutes)

Example 2

1-(2,3-Dihydro-1H-inden-2-yl)-4,6-dimethyl-2-[(E)-3-(4-morpholinyl)-3-oxo-1-propenyl]-1H-pyrrolo[2,3-b]pyridine-3-carbonitrile

(1) 1-(2,3-Dihydro-1H-inden-2-yl)-2-formyl-4,6-dimethyl-1H-pyrrolo[2,3-b]pyridine-3-carbonitrile In the same manner described in (1) of Example 1, 1-(2,3-dihydro-1H-inden-2-yl)-2-formyl-4,6-dimethyl-1H-pyrrolo[2,3-b]pyridine-3-carbonitrile was synthesized from 1-(2,3-dihydro-1H-inden-2-yl)-4,6-dimethyl-1H-pyrrolo[2,3-b]pyridine-3-carbonitrile.
Yield (amount) 2.9 g, yield (rate) 91% NMR (CDCl$_3$) δ: 2.55 (3H, s), 2.78 (3H, s), 3.30 (2H, dd, J=9.2 Hz, 14.6 Hz), 3.75 (2H, dd, J=9.6 Hz, 15.0 Hz), 6.51 (1H, m), 6.97 (1H, s), 7.23-7.28 (4H, m), 10.2 (1H, s)

(2) Ethyl (E)-3-[3-cyano]-1-(2,3-dihydro-1H-inden-2-yl)-4,6-dimethyl-1H-pyrrolo[2,3-b]pyridin-2-yl]-2-propenoate In the same manner described in (2) of Example 1, ethyl (E)-3-[3-cyano]-1-(2,3-dihydro-1H-inden-2-yl)-4,6-dimethyl-1H-pyrrolo[2,3-b]pyridin-2-yl]-2-propenoate was synthesized from 1-(2,3-dihydro-1H-inden-2-yl)-2-formyl-4,6-dimethyl-1H-pyrrolo[2,3-b]pyridine-3-carbonitrile.
Yield (amount) 1.9 g, yield (rate) 55% $^1$H-NMR (CDCl$_3$) δ: 1.25 (3H, t, J=7.2 Hz), 2.53 (3H, s), 2.74 (3H, s), 3.45 (2H, dd, J=9.4 Hz, 15.6 Hz), 3.80 (2H, dd, J=8.0 Hz, 16.2 Hz), 4.18 (2H, dd, J=7.4 Hz, 14.4 Hz), 5.93 (1H, m), 6.88 (1H, s), 7.02 (1H, d, J=16.4 Hz), 7.26-7.27 (4H, m), 7.61 (1H, d, J=16.2 Hz)

(3) (E)-3-[3-cyano-1-(2,3-dihydro-1H-inden-2-yl)-4,6-dimethyl-1H-pyrrolo[2,3-b]pyridin-2-yl]-2-propenoic acid In the same manner described in (3) of Example 1, (E)-3-[3-cyano-1-(2,3-dihydro-1H-inden-2-yl)-4,6-dimethyl-1H-pyrrolo[2,3-b]pyridin-2-yl]-2-propenoic acid was synthesized from ethyl (E)-3-[3-cyano-1-(2,3-dihydro-1H-inden-2-yl)-4,6-dimethyl-1H-pyrrolo[2,3-b]pyridin-2-yl]-2-propenoate.
Yield (amount) 1.4 g, yield (rate) 99% $^1$H-NMR (CDCl$_3$) δ: 2.54 (3H, s), 2.75 (3H, s), 3.49 (2H, dd, J=7.6 Hz, 16.0 Hz), 3.74 (2H, dd, J=8.0 Hz, 16.0 Hz), 5.99 (1H, m), 6.89 (1H, s), 7.00 (1H, d, J=16.2 Hz), 7.26-7.27. (4H, m), 7.67 (1H, d, J=15.6 Hz)

(4) 1-(2,3-Dihydro-1H-inden-2-yl)-4,6-dimethyl-2-[(E)-3-(4-morpholinyl)-3-oxo-1-propenyl]-1H-pyrrolo[2,3-b]pyridine-3-carbonitrile To a solution of (E)-3-[3-cyano-1-(2,3-dihydro-1H-inden-2-yl)-4,6-dimethyl-1H-pyrrolo[2,3-b]pyridin-2-yl]-2-propenoate (50 μmol) in tetrahydrofuran (600 μl) was sequentially added DMF (2 μl) and oxalylchloride (5.2 μl, 60 μmol) and the mixture was shaken for 1 hour under room temperature to give Solution A. To a solution of triethylamine (120 μmol) and morpholine (75 μmol) in dichloromethane (800 μl) was added the solution A and the mixture was stirred at room temperature for 1 hour. Then, PS-isocyanate (84 mg, 1.49 mmol/g) was added thereto and the mixture was stirred at room temperature for 2 hours. Then, MP-carbonate (134 mg, 2.69 mmol/g) was added thereto and the mixture was stirred at room temperature for 2 hours. A resin reagent was filtered from the reaction mixture and the remaining resin reagent was further twice washed with a dichloromethane/methanol (4:1, v/v) solvent (1 ml) to yield a filtrate. The solvent was removed to give the title compound (14 mg).
$^1$H-NMR (CDCl$_3$) δ: 2.51 (3H, s), 2.73 (3H, s), 3.35 (2H, dd, J=9.0 Hz, 15.3 Hz), 3.68-3.74 (8H, m), 3.90 (2H, dd, J=9.6 Hz, 15.3 Hz), 5.84 (1H, m), 6.87 (1H, s), 7.23-7.27 (4H, m), 7.53 (1H, d, J=15.6 Hz), 7.75 (1H, d, J=15.3 Hz). LC-MS(ESI-) analysis: Purity 97%, 427(M+H) (retention time: 2.26 minutes)

Example 3

(E)-3-[3-cyano-4,6-dimethyl-1-(1,2,3,4-tetrahydro-1-naphthalenyl)-1H-pyrrolo[2,3-b]pyridin-2-yl]-N-methyl 1-N-tetrahydro-2H-pyran-4-yl-2-propenamide In the same manner described in (4) of Example 2, (E)-3-[3-cyano-4,6-dimethyl-1-(1,2,3,4-tetrahydro-1-naphthalenyl)-1H-pyrrolo[2,3-b]pyridin-2-yl]-N-methyl 1-N-tetrahydro-2H-pyran-4-yl-2-propenamide was synthesized from (E)-3-[3-cyano-4,6-dimethyl-1-(1,2,3,4-tetrahydro-1-naphthalenyl)-1H-pyrrolo[2,3-b]pyridin-2-yl]-2-propenoic acid and N-methyltetrahydro-2H-pyran-4-ylamine.
Yield (amount) 16 mg LC-
MS(ESI-) analysis: Purity 91%, 469(M+H) (retention time: 2.37 minutes)

Example 4

(E)-3-[3-cyano-4,6-dimethyl-1-(1,2,3,4-tetrahydro-1-naphthalenyl)-1H-pyrrolo[2,3-b]pyridin-2-yl]-N-(3-pyridinyl)-2-propenamide In the same manner described in (4) of Example 2, (E)-3-[3-cyano-4,6-dimethyl-1-(1,2,3,4-tetrahydro-1-naphthalenyl)-1H-pyrrolo[2,3-b]pyridin-2-yl]-N-(3-pyridinyl)-2-propenamide was synthesized from (E)-3-[3-cyano-4,6-dimethyl-1-(1,2,3,4-tetrahydro-1-naphthalenyl)-1H-pyrrolo[2,3-b]pyridin-2-yl]-2-propenoic acid and 3-aminopyridine.

Yield (amount) 19 mg LC-
MS(ESI-) analysis: Purity 90%, 448(M+H) (retention time: 1.92 minutes)

Example 5

(E)-3-[3-cyano-4,6-dimethyl-1-(1,2,3,4-tetrahydro-1-naphthalenyl)-1H-pyrrolo[2,3-b]pyridin-2-yl]-N-(4-pyridinyl)-2-propenamide In the same manner described in (4) of Example 2, (E)-3-[3-cyano-4,6-dimethyl-1-(1,2,3,4-tetrahydro-1-naphthalenyl)-1H-pyrrolo[2,3-b]pyridin-2-yl]-N-(4-pyridinyl)-2-propenamide was synthesized from (E)-3-[3-cyano-4,6-dimethyl-1-(1,2,3,4-tetrahydro-1-naphthalenyl)-1H-pyrrolo[2,3-b]pyridin-2-yl]-2-propenoic acid and 4-aminopyridine.

Yield (amount) 11 mg LC-
MS(ESI-) analysis: Purity 88%, 448(M+H) (retention time: 1.91 minutes)

Example 6

4,6-Dimethyl-2-[(E)-3-(4-morpholinyl)-3-oxo-1-propenyl]-1-(1,2,3,4-tetrahydro-1-naphthalenyl)-1H-pyrrolo[2,3-b]pyridine-3-carbonitrile In the same manner described in (4) of Example 2, 4,6-dimethyl-2-[(E)-3-(4-morpholinyl)-3-oxo-1-propenyl]-1-(1,2,3,4-tetrahydro-1-naphthalenyl)-1H-pyrrolo[2,3-b]pyridine-3-carbonitrile was synthesized from (E)-3-[3-cyano-4,6-dimethyl-1-(1,2,3,4-tetrahydro-1-naphthalenyl)-1H-pyrrolo[2,3-b]pyridin-2-yl]-2-propenoic acid and morpholine.

Yield (amount) 17 mg LC-
MS(ESI-) analysis: Purity 95%, 441(M+H) (retention time: 2.31 minutes)

Example 7

4,6-Dimethyl 1-2-[(E)-3-oxo-3-(4-thiomorpholinyl)-1-propenyl]-1-(1,2,3,4-tetrahydro-1-naphthalenyl)-1H-pyrrolo[2,3-b]pyridine-3-carbonitrile In the same manner described in (4) of Example 2, 4,6-dimethyl 1-2-[(E)-3-oxo-3-(4-thiomorpholinyl)-1-propenyl]-1-(1,2,3,4-tetrahydro-1-naphthalenyl)-1H-pyrrolo[2,3-b]pyridine-3-carbonitrile was synthesized from (E)-3-[3-cyano-4,6-dimethyl-1-(1,2,3,4-tetrahydro-1-naphthalenyl)-1H-pyrrolo[2,3-b]pyridin-2-yl]-2-propenoic acid and thiomorpholine.

Yield (amount) 20 mg LC-
MS(ESI-) analysis: Purity 93%, 457(M+H) (retention time: 2.45 minutes)

Example 8

2-[(E)-3-(2,6-dimethyl-4-morpholinyl)-3-oxo-1-propenyl]-4,6-dimethyl-1-(1,2,3,4-tetrahydro-1-naphthalenyl)-1H-pyrrolo[2,3-b]pyridine-3-carbonitrile In the same manner described in (4) of Example 2, 2-[(E)-3-(2,6-dimethyl-4-morpholinyl)-3-oxo-1-propenyl]-4,6-dimethyl-1-(1,2,3,4-tetrahydro-1-naphthalenyl)-1H-pyrrolo[2,3-b]pyridine-3-carbonitrile was synthesized from (E)-3-[3-cyano-4,6-dimethyl-1-(1,2,3,4-tetrahydro-1-naphthalenyl)-1H-pyrrolo[2,3-b]pyridin-2-yl]-2-propenoic acid and 2,6-dimethylmorpholine.

Yield (amount) 19 mg LC-
MS(ESI-) analysis: Purity 94%, 469(M+H) (retention time: 2.47 minutes)

Example 9

(E)-3-[3-cyano-1-(2,3-dihydro-1H-inden-2-yl)-4,6-dimethyl-1H-pyrrolo[2,3-b]pyridin-2-yl]-N-methyl-N-tetrahydro-2H-pyran-4-yl-2-propenamide In the same manner described in (4) of Example 2, (E)-3-[3-cyano-1-(2,3-dihydro-1H-inden-2-yl)-4,6-dimethyl-1H-pyrrolo[2,3-b]pyridin-2-yl]-N-methyl-N-tetrahydro-2H-pyran-4-yl-2-propenamide was synthesized from (E)-3-[3-cyano-1-(2,3-dihydro-1H-inden-2-yl)-4,6-dimethyl-1H-pyrrolo[2,3-b]pyridin-2-yl]-2-propenoic acid and N-methyltetrahydro-2H-pyran-4-ylamine.

Yield (amount) 16 mg LC-
MS(ESI-) analysis: Purity 94%, 455(M+H) (retention time: 2.33 minutes)

Example 10

(E)-3-[3-cyano-1-(2,3-dihydro-1H-inden-2-yl)-4,6-dimethyl-1H-pyrrolo[2,3-b]pyridin-2-yl]-N-(3-pyridyl)-2-propenamide In the same manner described in (4) of Example 2, (E)-3-[3-cyano-1-(2,3-dihydro-1H-inden-2-yl)-4,6-dimethyl-1H-pyrrolo[2,3-b]pyridin-2-yl]-N-(3-pyridyl)-2-propenamide was synthesized from (E)-3-[3-cyano-1-(2,3-dihydro-1H-inden-2-yl)-4,6-dimethyl-1H-pyrrolo[2,3-b]pyridin-2-yl]-2-propenoic acid and 3-aminopyridine.

Yield (amount) 18 mg LC-
MS(ESI-) analysis: Purity 89%, 434(M+H) (retention time: 1.92 minutes)

Example 11

(E)-3-[3-cyano-1-(2,3-dihydro-1H-inden-2-yl)-4,6-dimethyl-1H-pyrrolo[2,3-b]pyridin-2-yl]-N-(4-pyridinyl)-2-propenamide In the same manner described in (4) of Example 2, (E)-3-[3-cyano-1-(2,3-dihydro-1H-inden-2-yl)-4,6-dimethyl-1H-pyrrolo[2,3-b]pyridin-2-yl]-N-(4-pyridinyl)-2-propenamide was synthesized from (E)-3-[3-cyano-1-(2,3-dihydro-1H-inden-2-yl)-4,6-dimethyl-1H-pyrrolo[2,3-b]pyridin-2-yl]-2-propenoic acid and 4-aminopyridine.

Yield (amount) 17 mg LC-
MS(ESI-) analysis: Purity 91%, 434(M+H) (retention time: 1.90 minutes)

Example 12

1-(2,3-Dihydro-1H-inden-2-yl)-4,6-dimethyl-2-[(E)-3-oxo-3-(4-thiomorpholinyl)-1-propenyl]-1H-pyrrolo[2,3-b]pyridine-3-carbonitrile In the same manner described in (4) of Example 2, 1-(2,3-dihydro-1H-inden-2-yl)-4,6-dimethyl-2-[(E)-3-oxo-3-(4-thiomorpholinyl)-1-propenyl]-1H-pyrrolo[2,3-b]pyridine-3-carbonitrile was synthesized from (E)-3-[3-cyano-1-(2,3-dihydro-1H-inden-2-yl)-4,6-dimethyl-1H-pyrrolo[2,3-b]pyridin-2-yl]-2-propenoic acid and thiomorpholine.

Yield (amount) 17 mg LC-MS(ESI-) analysis: Purity 93%, 443(M+H) (retention time: 2.42 minutes)

Example 13

1-(2,3-Dihydro-1H-inden-2-yl)-2-[(E)-3-(2,6-dimethyl-4-morpholinyl)-3-oxo-1-propenyl]-4,6-dimethyl-1H-pyrrolo[2,3-b]pyridine-3-carbonitrile In the same manner described in (4) of Example 2, 1-(2,3-dihydro-1H-inden-2-yl)-2-[(E)-3-(2,6-dimethyl-4-morpholinyl)-3-oxo-1-propenyl]-4,6-dimethyl-1H-pyrrolo[2,3-b]pyridine-3-carbonitrile was synthesized from (E)-3-[3-cyano-1-(2,3-dihydro-1H-inden-2-yl)-4,6-dimethyl-1H-pyrrolo[2,3-b]pyridin-2-yl]-2-propenoic acid and 2,6-dimethylmorpholine.

Yield (amount) 20 mg LC-MS(ESI-) analysis: Purity 97%, 455(M+H) (retention time: 2.44 minutes)

Example 14

(E)-3-[3-cyano-1-(4,5-dimethoxy-2,3-dihydro-1H-inden-1-yl)-4,6-dimethyl-1H-pyrrolo[2,3-b]pyridin-2-yl]-N-(2,2-dimethyltetrahydro-2H-pyran-4-yl)-2-propenamide (1) 1-(4,5-dimethoxy-2,3-dihydro-1H-inden-1-yl)-2-formyl-4,6-dimethyl-1H-pyrrolo[2,3-b]pyridine-3-carbonitrile In the same manner described in (1) of Example 1, 1-(4,5-dimethoxy-2,3-dihydro-1H-inden-1-yl)-2-formyl-4,6-dimethyl-1H-pyrrolo[2,3-b]pyridine-3-carbonitrile was synthesized from 1-(4,5-dimethoxy-2,3-dihydro-1H-inden-1-yl)-4,6-dimethyl-1H-pyrrolo[2,3-b]pyridine-3-carbonitrile.

Yield (amount) 1.0 g, yield (rate) 92% $^1$H-NMR (CDCl$_3$) δ: 2.56 (4H, m), 2.69-2.84 (4H, m), 3.00-3.17 (1H, m), 3.46-3.57 (1H, m), 3.82 (3H, s), 3.93 (3H, s), 6.46 (1H, d, J=8.0 Hz), 6.67 (1H, d, J=8.2 Hz), 6.96 (1H, s), 7.13 (1H, t, J=8.2 Hz), 9.93 (1H, br)

(2) Ethyl (E)-3-[3-cyano-1-(4,5-dimethoxy-2,3-dihydro-1H-inden-1-yl)-4,6-dimethyl-1H-pyrrolo[2,3-b]pyridin-2-yl]-2-propenoate In the same manner described in (2) of Example 1, ethyl (E)-3-[3-cyano-1-(4,5-dimethoxy-2,3-dihydro-1H-inden-1-yl)-4,6-dimethyl-1H-pyrrolo[2,3-b]pyridin-2-yl]-2-propenoate was synthesized from 1-(4,5-dimethoxy-2,3-dihydro-1H-inden-1-yl)-2-formyl-4,6-dimethyl-1H-pyrrolo[2,3-b]pyridine-3-carbonitrile.

Yield (amount) 780 mg, yield (rate) 69% NMR (CDCl$_3$) δ: 1.26 (3H, t, J=7.0 Hz), 2.20-2.40 (1H, m), 2.59 (3H, s), 2.78-2.96 (4H, m), 3.01-3.18 (1H, m), 3.34-3.49 (1H, m), 3.85 (3H, s), 3.95 (3H, s), 4.16 (2H, dd, J=7.0 Hz, 14.2Hz), 6.54 (1H, d, J=9.2 Hz), 6.72-6.96 (4H, m), 7.18-7.26 (1H, m)

(3) (E)-3-[3-cyano-1-(4,5-dimethoxy-2,3-dihydro-1H-inden-1-yl)-4,6-dimethyl-1H-pyrrolo[2,3-b]pyridin-2-yl]-2-propenoic acid In the same manner described in (3) of Example 1, (E)-3-[3-cyano-1-(4,5-dimethoxy-2,3-dihydro-1H-inden-1-yl)-4,6-dimethyl-1H-pyrrolo[2,3-b]pyridin-2-yl]-2-propenoic acid was synthesized from ethyl (E)-3-[3-cyano-1-(4,5-dimethoxy-2,3-dihydro-1H-inden-1-yl)-4,6-dimethyl-1H-pyrrolo[2,3-b]pyridin-2-yl]-2-propenoate.

Yield (amount) 600 mg, yield (rate) 92% $^1$H-NMR (CDCl$_3$) δ: 2.20-2.35 (1H, m), 2.61 (3H, s), 2.76 (3H, s), 2.85-2.96 (1H, m), 3.06-3.17 (1H, m), 3.35-3.43 (1H, m), 3.86 (3H, s), 3.93 (3H, s), 6.56 (1H, d, J=8.4 Hz), 6.74-6.87 (2H, m), 6.93-7.00 (2H, m), 7.26-7.31 (1H, m)

(4) (E)-3-[3-cyano-1-(4,5-dimethoxy-2,3-dihydro-1H-inden-1-yl)-4,6-dimethyl-1H-pyrrolo[2,3-b]pyridin-2-yl]-N-(2,2-dimethyltetrahydro-2H-pyran-4-yl)-2-propenamide In the same manner described in (4) of Example 2, (E)-3-[3-cyano-1-(4,5-dimethoxy-2,3-dihydro-1H-inden-1-yl)-4,6-dimethyl-1H-pyrrolo[2,3-b]pyridin-2-yl]-N-(2,2-dimethyltetrahydro-2H-pyran-4-yl)-2-propenamide was synthesized from (E)-3-[3-cyano-1-(4,5-dimethoxy-2,3-dihydro-1H-inden-1-yl)-4,6-dimethyl-1H-pyrrolo[2,3-b]pyridin-2-yl]-2-propenoic acid and 2,2-dimethyltetrahydro-2H-pyran-4-ylamine.

Yield (amount) 23 mg LC-MS(ESI-) analysis: Purity 95%, 529(M+H) (retention time: 2.26 minutes)

Example 15

(E)-3-[3-cyano-1-(4,5-dimethoxy-2,3-dihydro-1H-inden-1-yl)-4,6-dimethyl-1H-pyrrolo[2,3-b]pyridin-2-yl]-N-methyl-N-tetrahydro-2H-pyran-4-yl-2-propenamide In the same manner described in (4) of Example 2, (E)-3-[3-cyano-1-(4,5-dimethoxy-2,3-dihydro-1H-inden-1-yl)-4,6-dimethyl-1H-pyrrolo[2,3-b]pyridin-2-yl]-N-methyl-N-tetrahydro-2H-pyran-4-yl-2-propenamide was synthesized from (E)-3-[3-cyano-1-(4,5-dimethoxy-2,3-dihydro-1H-inden-1-yl)-4,6-dimethyl-1H-pyrrolo[2,3-b]pyridin-2-yl]-2-propenaote and N-methyltetrahydro-2H-pyran-4-ylamine.

Yield (amount) 23 mg LC-MS(ESI-) analysis: Purity 97%, 515(M+H) (retention time: 2.24 minutes)

Example 16

(E)-3-[3-cyano-1-(4,5-dimethoxy-2,3-dihydro-1H-inden-1-yl)-4,6-dimethyl-1H-pyrrolo[2,3-b]pyridin-2-yl]-N-(3-pyridinyl)-2-propenamide In the same manner described in (4) of Example 2, (E)-3-[3-cyano-1-(4,5-dimethoxy-2,3-dihydro-1H-inden-1-yl)-4,6-dimethyl-1H-pyrrolo[2,3-b]pyridin-2-yl]-N-(3-pyridinyl)-2-propenamide was synthesized from (E)-3-[3-cyano-1-(4,5-dimethoxy-2,3-dihydro-1H-inden-1-yl)-4,6-dimethyl-1H-pyrrolo[2,3-b]pyridin-2-yl]-2-propenoic acid and 3-aminopyridine.

Yield (amount) 21 mg LC-
MS(ESI−) analysis: Purity 93%, 494(M+H) (retention time: 1.85 minutes)

Example 17

(E)-3-[3-cyano-1-(4,5-dimethoxy-2,3-dihydro-1H-inden-1-yl)-4,6-dimethyl-1H-pyrrolo[2,3-b]pyridin-2-yl]-N-(4-pyridinyl)-2-propenamide In the same manner described in (4) of Example 2, (E)-3-[3-cyano-1-(4,5-dimethoxy-2,3-dihydro-1H-inden-1-yl)-4,6-dimethyl-1H-pyrrolo[2,3-b]pyridin-2-yl]-N-(4-pyridinyl)-2-propenamide was synthesized from (E)-3-[3-cyano-1-(4,5-dimethoxy-2,3-dihydro-1H-inden-1-yl)-4,6-dimethyl-1H-pyrrolo[2,3-b]pyridin-2-yl]-2-propenoic acid and 4-aminopyridine.

Yield (amount) 20 mg LC-
MS(ESI-) analysis: Purity 90%, 494(M+H) (retention time: 1.84 minutes)

Example 18

1-(4,5-Dimethoxy-2,3-dihydro-1H-inden-1-yl)-4,6-dimethyl-2-[(E)-3-(4-morpholinyl)-3-oxo-1-propenyl]-1H-pyrrolo[2,3-b]pyridine-3-carbonitrile In the same manner described in (4) of Example 2, 1-(4,5-dimethoxy-2,3-dihydro-1H-inden-1-yl)-4,6-dimethyl-2-[(E)-3-(4-morpholinyl)-3-oxo-1-propenyl]-1H-pyrrolo[2,3-b]pyridine-3-carbonitrile was synthesized from (E)-3-[3-cyano-1-(4,5-dimethoxy-2,3-dihydro-1H-inden-1-yl)-4,6-dimethyl-1H-pyrrolo[2,3-b]pyridin-2-yl]-2-propenoic acid and morpholine.

Yield (amount) 21 mg LC-
MS(ESI-) analysis: Purity 99%, 487(M+H) (retention time: 2.18 minutes)

Example 19

1-(4,5-Dimethoxy-2,3-dihydro-1H-inden-1-yl)-4,6-dimethyl-2-[(E)-3-oxo-3-(4-thiomorpholinyl)-1-propenyl]-1H-pyrrolo[2,3-b]pyridine-3-carbonitrile In the same manner described in (4) of Example 2, 1-(4,5-dimethoxy-2,3-dihydro-1H-inden-1-yl)-4,6-dimethyl-2-[(E)-3-oxo-3-(4-thiomorpholinyl)-1-propenyl]-1H-pyrrolo[2,3-b]pyridine-3-carbonitrile was synthesized from (E)-3-[3-cyano-1-(4,5-dimethoxy-2,3-dihydro-1H-inden-2-yl)-4,6-dimethyl-1H-pyrrolo[2,3-b]pyridin-2-yl]-2-propenoic acid and thiomorpholine.

Yield (amount) 20 mg LC-
MS(ESI-) analysis: Purity 95%, 503(M+H) (retention time: 2.33 minutes)

Example 20

1-(4,5-Dimethoxy-2,3-dihydro-1H-inden-1-yl)-2-[(E)-3-(2,6-dimethyl-4-morpholinyl)-3-oxo-1-propenyl]-4,6-dimethyl-1H-pyrrolo[2,3-b]pyridine-3-carbonitrile In the same manner described in (4) of Example 2, 1-(4,5-dimethoxy-2,3-dihydro-1H-inden-1-yl)-2-[(E)-3.-(2,6-dimethyl-4-morpholinyl)-3-oxo-1-propenyl]-4,6-dimethyl-1H-pyrrolo[2,3-b]pyridine-3-carbonitrile was synthesized from (E)-3-[3-cyano-1-(4,5-dimethoxy-2,3-dihydro-1H-inden-2-yl)-4,6-dimethyl-1H-pyrrolo[2,3-b]pyridin-2-yl]-2-propenoic acid and 2,6-dimethylmorpholine.

Yield (amount) 19 mg LC-
MS(ESI-) analysis: Purity 96%, 515(M+H) (retention time: 2.35 minutes)

Reference Example 8

5,6-Dimethoxy-1,2,3,4-tetrahydronaphthalen-1-ylamine 5,6-Dimethoxy-1,2,3,4-tetrahydronaphthalen-1-one (5.1 g, 25 mmol) and hydroxylamine hydrate (3.5 g) were dissolved in ethanol 100 ml and the resultant solution was stirred at room temperature overnight. After distilling off the solvent, ethyl acetate was added thereto and the mixture washed with water. The organic layer was dried over sodium sulfate and then the solvent was distilled off to give an oxime product. The resultant product was dissolved in ethanol 150 ml and water 50 ml, concentrated hydrochloric acid 3 ml was added thereto, and reduced with 10% palladium/carbon (NE Chemcat Corporation) as a catalyst under hydrogen atmosphere for 3 days. After removing the catalyst by celite filtration, the solvent was distilled off. Ethyl acetate was added thereto and the mixture was distributed to a 1 N aqueous sodium hydroxide solution and saturated brine. The organic layer was dried over sodium sulfate and then the solvent was distilled off to give the title compound as oily matter.

$^1$H-NMR (CDCl$_3$) δ: 1.60-1.78 (2H, m), 1.87-1.98 (2H, m), 2.66-2.84 (2H, m), 3.79 (3H, s), 3.85 (3H, s), 3.94 (1H, t, J=6.0 Hz), 6.8 (1H, d, J=9.0 Hz), 7.13 (1H, d, J=9.0 Hz)

Example 21

(E)-3-[3-cyano-1-(5,6-dimethoxy-1,2,3,4-tetrahydro-1-naphthalenyl)-4,6-dimethyl-1H-pyrrolo[2,3-b]pyridin-2-yl]-N-(2,2-dimethyltetrahydro-2H-pyran-4-yl)-2-propenamide (1) 1-(5,6-Dimethoxy-1,2,3,4-tetrahydro-1-naphthalenyl)-2-formyl-4,6-dimethyl-1H-pyrrolo[2,3-b]pyridine-3-carbonitrile In the same manner described in (1) of Example 1, 1-(5,6-dimethoxy-1,2,3,4-tetrahydro-1-naphthalenyl)-2-formyl-4,6-dimethyl-1H-pyrrolo[2,3-b]pyridine-3-carbonitrile was synthesized from 1-(5,6-dimethoxy-1,2,3,4-tetrahydro-1-naphthalenyl)-4,6-dimethyl-1H-pyrrolo[2,3-b]pyridine-3-carbonitrile.

Yield (amount) 1.8 g, yield (rate) 91% $^1$H-NMR (CDCl$_3$) δ: 1.80-2.01 (1H, m), 2.13-2.31 (3H, m), 2.59 (3H, s), 2.80-2.95 (4H, m), 3.01-3.22 (1H, m), 3.78 (3H, s), 3.85 (3H, s), 6.08 (1H, d, J=8.0 Hz), 6.54 (1H, d, J=8.6 Hz), 6.77 (1H, t, J=8.4 Hz), 6.99 (1H, s), 9.88 (1H, br)

(2) Ethyl (E)-3-[3-cyano-1-(5,6-dimethoxy-1,2,3,4-tetrahydro-1-naphthalenyl)-4,6-dimethyl-1H-pyrrolo[2,3-b]pyridin-2-yl]-2-propenoate In the same manner described in (2) of Example 1, ethyl (E)-3-[3-cyano-1-(5,6-dimethoxy-1,2,3,4-tetrahydro-1-naphthalenyl)-4,6-dimethyl-1H-pyrrolo[2,3-b]pyridin-2-yl]-2-propenoate was synthesized from 1-(5,6-dimethoxy-1,2,3,4-tetrahydro-1-naphthalenyl)-2-formyl-4,6-dimethyl-1H-pyrrolo[2,3-b]pyridine-3-carbonitrile.

Yield (amount) 1.5 g, yield (rate) 73% $^1$H-NMR (CDCl$_3$) δ: 1.26 (3H, t, J=7.2 Hz), 1.87-2.35 (4H, m), 2.59 (3H, s), 2.71-2.96 (4H, m), 3.13-3.22 (1H, m), 3.80 (3H, s), 3.87 (3H, s), 4.15 (2H, dd, J=7.0 Hz, 14.4 Hz), 6.26 (1H, d, J=8.4 Hz), 6.60-6.69 (2H, m), 6.78-6.92 (2H, m), 7.23-7.31 (1H, m)

(3) (E)-3-[3-cyano-1-(5,6-dimethoxy-1,2,3,4-tetrahydro-1-naphthalenyl)-4,6-dimethyl-1H-pyrrolo[2,3-b]pyridin-2-yl]-2-propenoic acid In the same manner described in (3) of Example 1, (E)-3-[3-cyano-1-(5, 6-dimethoxy-1,2,3,4-tetrahydro-1-naphthalenyl)-4,6-dimethyl-1H-pyrrolo[2,3-b]pyridin-2-yl]-2-propenoic acid was synthesized from ethyl (E)-3-[3-cyano-1-(5,6-dimethoxy-1,2,3,4-tetrahydro-1-naphthalenyl)-4,6-dimethyl-1H-pyrrolo[2,3-b]pyridin-2-yl]-2-propenoate.

Yield (amount) 880 mg, yield (rate) 68% $^1$H-NMR (CDCl$_3$) δ: 1.87-2.17 (3H, m), 2.31-2.37 (1H, m), 2.61 (3H, s), 2.73-2.82 (4H, m), 3.16-3.24 (1H, m), 3.81 (3H, s), 3.84 (3H, s), 6.29 (1H, d, J=9.0 Hz), 6.61-6.71 (2H, m), 6.80 (1H, d, J=15.9 Hz), 6.94 (1H, s), 7.34 (1H, d, J=15.9Hz)

(4) (E)-3-[3-cyano-1-(5,6-dimethoxy-1,2,3,4-tetrahydro-1-naphthalenyl)-4,6-dimethyl-1H-pyrrolo[2,3-b]pyridin-2-yl]-N-(2,2-dimethyltetrahydro-2H-pyran-4-yl)-2-propenamide In the same manner described in (4) of Example 2, (E)-3-[3-cyano-1-(5,6-dimethoxy-1,2,3,4-tetrahydro-1-naphthalenyl)-4,6-dimethyl-1H-pyrrolo[2,3-b]pyridin-2-yl]-N-(2,2-dimethyltetrahydro-2H-pyran-4-yl)-2-propenamide was synthesized from (E)-3-[3-cyano-1-(5,6-dimet-hoxy-1,2,3,4-tetrahydro-1-naphthalenyl)-4,6-dimethyl-1H-pyrrolo[2,3-b]pyridin-2-yl]-2-propenoic acid and 2,2-dimethyltetrahydro-2H-pyran-4-ylamine.

Yield (amount) 20 mg LC-MS(ESI-) analysis: Purity 92%, 543(M+H) (retention time: 2.36 minutes)

Example 22

(E)-3-[3-cyano-1-(5,6-dimethoxy-1,2,3,4-tetrahydro-1-naphthalenyl)-4,6-dimethyl-1H-pyrrolo[2,3-b]pyridin-2-yl]-N-methyl-N-tetrahydro-2H-pyran-4-yl-2-propenamide In the same manner described in (4) of Example 2, (E)-3-[3-cyano-1-(5,6-dimethoxy-1,2,3,4-tetrahydro-1-naphthalenyl)-4,6-dimethyl-1H-pyrrolo[2,3-b]pyridin-2-yl]-N-methyl-N-tetrahydro-2H-pyran-4-yl-2-propenamide was synthesized from (E)-3-[3-cyano-1-(5,6-dimethoxy-1,2,3,4-tetrahydro-1-naphthalenyl)-4,6-dimethyl-1H-pyrrolo[2,3-b]pyridin-2-yl]-2-propenoic acid and N-methyltetrahydro-2H-pyran-4-ylamine.

Yield (amount) 21 mg LC-MS(ESI-) analysis: Purity 94%, 529(M+H) (retention time: 2.32 minutes)

Example 23

(E)-3-[3-cyano-1-(5,6-dimethoxy-1,2,3,4-tetrahydro-1-naphthalenyl)-4,6-dimethyl-1H-pyrrolo[2,3-b]pyridin-2-yl]-N-(3-pyridine)-2-propenamide In the same manner described in (4) of Example 2, (E)-3-[3-cyano-1-(5,6-dimethoxy-1,2,3,4-tetrahydro-1-naphthalenyl)-4,6-dimethyl-1H-pyrrolo[2,3-b]pyridin-2-yl]-N-(3-pyridine)-2-propenamide was synthesized from (E)-3-[3-cyano-1-(5,6-dimethoxy-1,2,3,4-tetrahydro-1-naphthalenyl)-4,6-dimethyl-1H-pyrrolo[2,3-b]pyridin-2-yl]-2-propenoic acid and 3-aminopyridine.

Yield (amount) 23 mg LC-MS(ESI-) analysis: Purity 94%, 508(M+H) (retention time: 1.91 minutes)

Example 24

(E)-3-[3-cyano-1-(5,6-dimethoxy-1,2,3,4-tetrahydro-1-naphthalenyl)-4,6-dimethyl-1H-pyrrolo[2,3-b]pyridin-2-yl]-N-(4-pyridinyl)-2-propenamide In the same manner described in (4) of Example 2, (E)-3-[3-cyano-1-(5,6-dimethoxy-1,2,3,4-tetrahydro-1-naphthalenyl)-4,6-dimethyl-1H-pyrrolo[2,3-b]pyridin-2-yl]-N-(4-pyridinyl)-2-propenamide was synthesized from (E)-3-[3-cyano-1-(5,6-dimethoxy-1,2,3,4-tetrahydro-1-naphthalenyl)-4,6-dimethyl-1H-pyrrolo[2,3-b]pyridin-2-yl]-2-propenoic acid and 4-aminopyridine.

Yield (amount) 22 mg LC-MS(ESI-) analysis: Purity 95%, 508(M+H) (retention time: 1.89 minutes)

Example 25

1-(5,6-Dimethoxy-1,2,3,4-tetrahydro-1-naphthalenyl)-4,6-dimethyl-2-[(E)-3-(4-morpholinyl)-3-oxo-1-propenyl]-1H-pyrrolo[2,3-b]pyridine-3-carbonitrile In the same manner described in (4) of Example 2, 1-(5,6-dimethoxy-1,2,3,4-tetrahydro-1-naphthalenyl)-4,6-dimethyl-2-[(E)-3-(4-morpholinyl)-3-oxo-1-propenyl]-1H-pyrrolo[2,3-b]pyridine-3-carbonitrile was synthesized from (E)-3-[3-cyano-1-(5,6-dimethoxy-1,2,3,4-tetrahydro-1-naphthalenyl)-4,6-dimethyl-1H-pyrrolo[2,3-b]pyridin-2-yl]-2-propenoic acid and morpholine.

Yield (amount) 21 mg LC-MS(ESI-) analysis: Purity 99%, 501(M+H) (retention time: 2.26 minutes)

Example 26

1-(5,6-Dimethoxy-1,2,3,4-tetrahydro-1-naphthalenyl)-4,6-dimethyl-2-[(E)-3-oxo-3-(4-thiomorphollinyl)-1-propenyl]-1H-pyrrolo[2,3-b]pyridine-3-carbonitrile In the same manner described in (4) of Example 2, 1-(5,6-dimethoxy-1,2,3,4-tetrahydro-1-naphthalenyl)-4,6-dimethyl-2-[(E)-3-oxo-3-(4-thiomorphollinyl)-1-propenyl]-1H-pyrrolo[2,3-b]pyridine-3-carbonitrile was synthesized from (E)-3-[3-cyano-1-(5,6-dimethoxy-1,2,3,4-tetrahydro-1-naphthalenyl)-4,6-dimethyl-1H-pyrrolo[2,3-b]pyridin-2-yl]-2-propenoic acid and thiomorpholine.

Yield (amount) 18 mg LC-MS(ESI-) analysis: Purity 94%, 517(M+H) (retention time: 2.42 minutes)

Example 27

1-(5,6-Dimethoxy-1,2,3,4-tetrahydro-1-naphthalenyl)-2-[(E)-3-(2,6-dimethyl-4-morpholinyl)-3-oxo-1-propenyl]-4,6-dimethyl-1H-pyrrolo[2,3-b]pyridine-3-carbonitrile In the same manner described in (4) of Example 2, 1-(5,6-dimethoxy-1,2,3,4-tetrahydro-1-naphthalenyl)-2-[(E)-3-(2,6-dimethyl-4-morpholinyl)-3-oxo-1-propenyl]-4,6-dimethyl-1H-pyrrolo[2,3-b]pyridine-3-carbonitrile was synthesized from (E)-3-[3-cyano-1-(5,6-dimethoxy-1,2,3,4-tetrahydro-1-naphthalenyl)-4,6-dimethyl-1H-pyrrolo[2,3-b]pyridin-2-yl]-2-propenoic acid and 2,6-dimethylmorpholine.

Yield (amount) 17 mg LC-

MS(ESI-) analysis: Purity 95%, 529(M+H) (retention time: 2.44 minutes)

Example 28

(E)-3-[3-cyano-1-(2,3-dihydro-1H-inden-1-yl)-6-methyl-1H-pyrrolo[2,3-b]pyridin-2-yl]-N-(2,2-dimethyltetrahydro-2H-pyran-4-yl)-2-propenamide (1) 1-(2,3-Dihydro-1H-inden-1-yl)-2-formyl-6-methyl-1H-pyrrolo[2,3-b]pyridine-3-carbonitrile In the same manner described in (1) of Example 1, 1-(2,3-dihydro-1H-inden-1-yl)-2-formyl-6-methyl-1H-pyrrolo[2,3-b]pyridine-3-carbonitrile was synthesized from 1-(2,3-dihydro-1H-inden-1-yl)-6-methyl-1H-pyrrolo[2,3-b]pyridine-3-carbonitrile.

Yield (amount) 1.3 g, yield (rate) 88% $^1$H-NMR (CDCl$_3$) δ: 2.54-2.70 (4H, m), 2.77-2.96 (1H, m), 3.05-3.17 (1H, m), 3.22-3.51 (1H, m), 6.76 (1H, d, J=7.4 Hz), 7.06-7.37 (5H, m), 8.09 (1H, d, J=8.4 Hz), 9.89 (1H, br)

(2) Ethyl (E)-3-[3-cyano-1-(2,3-dihydro-1H-inden-1-yl)-6-methyl-1H-pyrrolo[2,3-b]pyridin-2-yl]-2-propenoate In the same manner described in (2) of Example 1, ethyl (E)-3-[3-cyano-1-(2,3-dihydro-1H-inden-1-yl)-6-methyl-1H-pyrrolo[2,3-b]pyridin-2-yl]-2-propenoate was synthesized from 1-(2,3-dihydro-1H-inden-1-yl)-2-formyl-6-methyl-1H-pyrrolo[2,3-b]pyridine-3-carbonitrile.

Yield (amount) 1.1 g, yield (rate) 69% $^1$H-NMR (CDCl$_3$) δ: 1.24 (3H, t, J=7.2 Hz), 2.26-2.42 (1H, m), 2.70 (3H, s), 2.78-2.96 (1H, m), 3.06-3.42 (2H, m), 4.14 (2H, dd, J=7.4 Hz, 14.4 Hz), 6.81-6.92 (2H, m), 7.01-7.42 (6H, m), 7.95 (1H, d, J=8.0 Hz)

(3) (E)-3-[3-cyano-1-(2,3-dihydro-1H-inden-1-yl)-6-methyl-1H-pyrrolo[2,3-b]pyridin-2-yl]-2-propenoic acid In the same manner described in (3) of Example 1, (E)-3-[3-cyano-1-(2,3-dihydro-1H-inden-1-yl)-6-methyl-1H-pyrrolo[2,3-b]pyridin-2-yl]-2-propenoic acid was synthesized from ethyl (E)-3-[3-cyano-1-(2,3-dihydro-1H-inden-1-yl)-6-methyl-1H-pyrrolo[2,3-b]pyridin-2-yl]-2-propenoate.

Yield (amount) 840 mg, yield (rate) 91% $^1$H-NMR (CDCl$_3$) δ : 2.26-2.42 (1H, m), 2.67 (3H, s), 2.83-2.96 (1H, m), 3.07-3.43 (2H, m), 6.79-6.89 (2H, m), 7.01-7.42 (6H, m), 7.97 (1H, d, J=8.2 Hz)

(4) (E)-3-[3-cyano-1-(2,3-dihydro-1H-inden-1-yl)-6-methyl-1H-pyrrolo[2,3-b]pyridin-2-yl]-N-(2,2-dimethyltetrahydro-2H-pyran-4-yl)-2-propenamide In the same manner described in (4) of Example 2, (E)-3-[3-cyano-1-(2,3-dihydro-1H-inden-1-yl)-6-methyl-1H-pyrrolo[2,3-b]pyridin-2-yl]-N-(2,2-dimethyltetrahydro-2H-pyran-4-yl)-2-propenamide was synthesized from (E)-3-[3-cyano-1-(2,3-dihydro-1H-inden-1-yl)-6-methyl-1H-pyrrolo[2,3-b]pyridin-2-yl]-2-propenoic acid and 2,2-dimethyltetrahydro-2H-pyran-4-ylamine.

Yield (amount) 22 mg LC-

MS(ESI-) analysis: Purity 90%, 455(M+H) (retention time: 2.25 minutes)

Example 29

(E)-3-[3-cyano-1-(2,3-dihydro-1H-inden-1-yl)-6-methyl-1H-pyrrolo[2,3-b]pyridin-2-yl]-N-methyl-N-tetrahydro-2H-pyran-4-yl-2-propenamide In the same manner described in (4) of Example 2, (E)-3-[3-cyano-1-(2,3-dihydro-iH-inden-1-yl)-6-methyl-1H-pyrrolo[2,3-b]pyridin-2-yl]-N-methyl-N-tetrahydro-2H-pyran-4-yl-2-propenamide was synthesized from (E)-3-[3-cyano-1-(2,3-dihydro-1H-inden-1-yl)-6-methyl-1H-pyrrolo[2,3-b]pyridin-2-yl]-2-propenoic acid and N-methyltetrahydro-2H-pyran-4-ylamine.

Yield (amount) 21 mg LC-

MS(ESI-) analysis: Purity 83%, 441(M+H) (retention time: 2.20 minutes)

Example 30

(E)-3-[3-cyano-1-(2,3-dihydro-1H-inden-1-yl)-6-methyl-1H-pyrrolo[2,3-b]pyridin-2-yl]-N-(3-pyridinyl)-2-propenamide In the same manner described in (4) of Example 2, (E)-3-[3-cyano-1-(2,3-dihydro-1H-inden-1-yl)-6-methyl-1H-pyrrolo[2,3-b]pyridin-2-yl]-N-(3-pyridinyl)-2-propenamide was synthesized from (E)-3-[3-cyano-1-(2,3-dihydro-1H-inden-1-yl)-6-methyl-1H-pyrrolo[2,3-b]pyridin-2-yl]-2-propenoic acid and 3-aminopyridine.

Yield (amount) 17 mg LC-

MS(ESI-) analysis: Purity 91%, 420(M+H) (retention time: 1.82 minutes)

Example 31

(E)-3-[3-cyano-1-(2,3-dihydro-1H-inden-1-yl)-6-methyl-1H-pyrrolo[2,3-b]pyridin-2-yl]-N-(4-pyridinyl)-2-propenamide In the same manner described in (4) of Example 2, (E)-3-[3-cyano-1-(2,3-dihydro-1H-inden-1-yl)-6-methyl-1H-pyrrolo[2,3-b]pyridin-2-yl]-N-(4-pyridinyl)-2-propenamide was synthesized from (E)-3-[3-cyano-1-(2,3-dihydro-1H-inden-1-yl)-6-methyl-1H-pyrrolo[2,3-b]pyridin-2-yl]-2-propenoic acid and 4-aminopyridine.

Yield (amount) 20 mg LC-

MS(ESI-) analysis: Purity 88%, 420(M+H) (retention time: 1.82 minutes)

Example 32

1-(2,3-Dihydro-1H-inden-1-yl)-6-methyl-2-[(E)-3-(4-morpholinyl)-3-oxo-1-propenyl]-1H-pyrrolo[2,3-b]pyridine-3-carbonitrile In the same manner described in (4) of Example 2, 1-(2,3-dihydro-1H-inden-1-yl)-6-methyl-2-[(E)-3-(4-morpholinyl)-3-oxo-1-propenyl]-1H-pyrrolo[2,3-b]pyridine-3-carbonitrile was synthesized from (E)-3-[3-cyano-1-(2,3-dihydro-1H-inden-1-yl)-6-methyl-1H-pyrrolo[2,3-b]pyridin-2-yl]-2-propenoic acid and morpholine.

Yield (amount) 19 mg LC-

MS(ESI-) analysis: Purity 93%, 413(M+H) (retention time: 2.14 minutes)

Example 33

1-(2,3-Dihydro-1H-inden-1-yl)-6-methyl-2-[(E)-3-oxo-3-(4-thiomorpholinyl)-1-propenyl]-1H-pyrrolo[2,3-b]pyridine-3-carbonitrile In the same manner described in (4) of Example 2, 1-(2,3-dihydro-1H-inden-1-yl)-6-methyl-2-[(E)-3-oxo-3-(4-thiomorpholinyl)-1-propenyl]-1H-pyrrolo[2,3-b]pyridine-3-carbonitrile was synthesized from (E)-3-[3-cyano-1-(2,3-dihydro-1H-inden-1-yl)-6-methyl-1H-pyrrolo[2,3-b]pyridin-2-yl]-2-propenoic acid and thiomorpholine.

Yield (amount) 17 mg LC-

MS(ESI-) analysis: Purity 87%, 429(M+H) (retention time: 2.30 minutes)

Example 34

1-(2,3-Dihydro-1H-inden-1-yl)-2-[(E)-3-(2,6-dimethyl-4-morpholinyl)-3-oxo-1-propenyl]-6-methyl-1H-pyrrolo[2,3-b]pyridine-3-carbonitrile In the same manner described in (4) of Example 2, 1-(2,3-dihydro-1H-inden-1-yl)-2-[(E)-3-(2,6-dimethyl-4-morpholinyl)-3-oxo-1-propenyl]-6-methyl-1H-pyrrolo[2,3-b]pyridine-3-carbonitrile was synthesized from (E)-3-[3-cyano-1-(2,3-dihydro-1H-inden-1-yl)-6-methyl-1H-pyrrolo[2,3-b]pyridin-2-yl]-2-propenoic acid and 2,6-dimethylmorpholine.

Yield (amount) 15 mg LC-

MS(ESI-) analysis: Purity 96%, 441(M+H) (retention time: 2.32 minutes)

Example 35

(E)-3-[3-cyano-1-(2,3-dihydro-1H-inden-1-yl)-4,6-diethyl-1H-pyrrolo[2,3-b]pyridin-2-yl]-N-(2,2-dimethyltetrahydro-2H-pyran-4-yl)-2-propenamide (1) 1-(2,3-Dihydro-1H-inden-1-yl)-4,6-diethyl-2-formyl-1H-pyrrolo[2,3-b]pyridine-3-carbonitrile In the same manner described in (1) of Example 2, 1-(2,3-dihydro-1H-inden-1-yl)-4,6-diethyl-2-formyl-1H-pyrrolo[2,3-b]pyridine-3-carbonitrile was synthesized from 1-(2,3-dihydro-1H-inden-1-yl)-4,6-diethyl-1H-pyrrolo[2,3-b]pyridine-3-carbonitrile.

Yield (amount) 2.9 g, yield (rate) 85% $^1$H-NMR (CDCl$_3$) δ: 1.22-1.45 (6H, m), 2.58-2.93 (3H, m), 2.97-3.24 (4H, m), 3.40-3.52 (1H, m), 6.75 (1H, t, J=7.4 Hz), 6.99-7.11 (2H, m), 7.20-7.36 (3H, m), 9.98 (1H, br)

(2) Ethyl (E)-3-[3-cyano-1-(2,3-dihydro-1H-inden-1-yl)-4,6-diethyl-1H-pyrrolo[2,3-b]pyridin-2-yl]-2-propenoate In the same manner described in (2) of Example 2, ethyl (E)-3-[3-cyano-1-(2,3-dihydro-1H-inden-1-yl)-4,6-diethyl-1H-pyrrolo[2,3-b]pyridin-2-yl]-2-propenoate was synthesized from 1-(2,3-dihydro-1H-inden-1-yl)-4,6-diethyl-1H-pyrrolo[2,3-b]pyridine-3-carbonitrile.

Yield (amount) 1.4 g, yield (rate) 69% $^1$H-NMR (CDCl$_3$) δ: 1.22-1.45 (9H, m), 2.28-2.40 (1H, m), 2.76-2.92 (3H, m), 3.05-3.21 (3H, m), 3.29-3.42 (1H, m), 4.15 (2H, dd, J=7.4 Hz, 14.2 Hz), 6.83-6.96 (3H, m), 7.01-7.41 (5H, m)

(3) (E)-3-[3-cyano-1-(2,3-dihydro-1H-inden-1-yl)-4,6-diethyl-1H-pyrrolo[2,3-b]pyridin-2-yl]-2-propenoic acid In the same manner described in (3) of Example 2, (E)-3-[3-cyano-1-(2,3-dihydro-1H-inden-1-yl)-4,6-diethyl-1H-pyrrolo[2,3-b]pyridin-2-yl]-2-propenoic acid was synthesized from ethyl (E)-3-[3-cyano-1-(2,3-dihydro-1H-inden-1-yl)-4,6-diethyl-1H-pyrrolo[2,3-b]pyridin-2-yl]-2-propenoate.

Yield (amount) 1.1 g, yield (rate) 94% $^1$H-NMR (CDCl$_3$) δ: 1.28-1.45 (6H, m), 2.25-2.42 (1H, m), 2.81-2.93 (3H, m), 3.07-3.22 (3H, m), 3.32-3.45 (1H, m), 6.81-7.41 (8H, m)

(4) (E)-3-[3-cyano-1-(2,3-dihydro-1H-inden-1-yl)-4,6-diethyl-1H-pyrrolo[2,3-b]pyridin-2-yl]-N-(2,2-dimethyltetrahydro-2H-pyran-4-yl)-2-propenamide In the same manner described in (4) of Example 2, ((E)-3-[3-cyano-1-(2,3-dihydro-1H-inden-1-yl)-4,6-diethyl-1H-pyrrolo[2,3-b]pyridin-2-yl]-N-(2,2-dimethyltetrahydro-2H-pyran-4-yl)-2-propenamide was synthesized from (E)-3-[3-cyano-1-(2,3-dihydro-1H-inden-1-yl)-4,6-diethyl-1H pyrrolo[2,3-b]pyridin-2-yl]-2-propenoic acid and 2,2-dimethyltetrahydro-2H-pyran-4-ylamine.

Yield (amount) 23 mg LC-

MS(ESI-) analysis: Purity 87%, 497(M+H) (retention time: 2.53 minutes)

Example 36

(E)-3-[3-cyano-1-(2,3-dihydro-1H-inden-1-yl)-4,6-diethyl-1H-pyrrolo[2,3-b]pyridin-2-yl]-N-methyl-N-tetrahydro-2H-pyran-4-yl-2-propenamide In the same manner described in (4) of Example 2, (E)-3-[3-cyano-1-(2,3-dihydro-1H-inden-1-yl)-4,6-diethyl-1H-pyrrolo[2,3-b]pyridin-2-yl]-N-methyl-N-tetrahydro-2H-pyran-4-yl-2-propenamide was synthesized from (E)-3-[3-cyano-1-(2,3-dihydro-1H-inden-1-yl)-4,6-diethyl-1H-pyrrolo[2,3-b]pyridin-2-yl]-2-propenoic acid and N-methyltetrahydro-2H-pyran-4-ylamine.

Yield (amount) 20 mg LC-

MS(ESI-) analysis: Purity 90%, 483(M+H) (retention time: 2.51 minutes)

Example 37

(E)-3-[3-cyano-1-(2,3-dihydro-1H-inden-1-yl)-4,6-diethyl-1H-pyrrolo[2,3-b]pyridin-2-yl]-N-(3-pyridinyl)-2-propenamide In the same manner described in (4) of Example 2, (E)-3-[3-cyano-1-(2,3-dihydro-1H-inden-1-yl)-4,6-diethyl-1H-pyrrolo[2,3-b]pyridin-2-yl]-N-(3-pyridinyl)-2-propenamide was synthesized from (E)-3-[3-cyano-1-(2,3-dihydro-1H-inden-1-yl)-4,6-diethyl-1H-pyrrolo[2,3-b]pyridin-2-yl]-2-propenoic acid and 3-aminopyridine.

Yield (amount) 20 mg LC-

MS(ESI-) analysis: Purity 92%, 462(M+H) (retention time: 2.04 minutes)

Example 38

(E)-3-[3-cyano-1-(2,3-dihydro-1H-inden-1-yl)-4,6-diethyl-1H-pyrrolo[2,3-b]pyridin-2-yl]-N-(4-pyridinyl)-2-propenamide In the same manner described in (4) of Example 2, (E)-3-[3-cyano-1-(2,3-dihydro-1H-inden-1-yl)-4,6-diethyl-1H-pyrrolo[2,3-b]pyridin-2-yl]-N-(3-pyridinyl)-2-propenamide was synthesized from (E)-3-[3-cyano-1-(2,3-dihydro-1H-inden-1-yl)-4,6-diethyl-1H-pyrrolo[2,3-b]pyridin-2-yl]-2-propenoic acid and 4-aminopyridine.

Yield (amount) 12 mg LC-
MS(ESI-) analysis: Purity 93%, 462(M+H) (retention time: 2.02 minutes)

Example 39

1-(2,3-Dihydro-1H-inden-1-yl)-4,6-diethyl-2-[(E)-3-(4-morpholinyl)-3-oxo-1-propenyl]-1H-pyrrolo[2,3-b]pyridine-3-carbonitrile In the same manner described in (4) of Example 2, 1-(2,3-dihydro-1H-inden-1-yl)-4,6-diethyl-2-[(E)-3-(4-morpholinyl)-3-oxo-1-propenyl]-1H-pyrrolo[2,3-b]pyridine-3-carbonitrile was synthesized from (E)-3-[3-cyano-1-(2,3-dihydro-1H-inden-1-yl)-4,6-diethyl-1H-pyrrolo[2,3-b]pyridin-2-yl]-2-propenoic acid and morpholine.

Yield (amount) 18 mg LC-
MS(ESI-) analysis: Purity 92%, 455(M+H) (retention time: 2.45 minutes)

Example 40

1-(2,3-Dihydro-1H-inden-1-yl)-4,6-diethyl-2-[(E)-3-oxo-3-(4-thiomorpholinyl)-1-propenyl]-1H-pyrrolo[2,3-b]pyridine-3-carbonitrile In the same manner described in (4) of Example 2, 1-(2,3-dihydro-1H-inden-1-yl)-4,6-diethyl-2-[(E)-3-oxo-3-(4-thiomorpholinyl)-1-propenyl]-1H-pyrrolo[2,3-b]pyridine-3-carbonitrile was synthesized from (E)-3-[3-cyano-1-(2,3-dihydro-1H-inden-1-yl)-4,6-diethyl-1H-pyrrolo[2,3-b]pyridin-2-yl]-2-propenoic acid and thiomorpholine.

Yield (amount) 15 mg LC-
MS(ESI-) analysis: Purity 89%, 471(M+H) (retention time: 2.59 minutes)

Example 41

1-(2,3-Dihydro-1H-inden-1-yl)-2-[(E)-3-(2,6-dimethyl-4-morpholinyl)-3-oxo-1-propenyl]-4,6-diethyl-1H-pyrrolo[2,3-b]pyridine-3-carbonitrile In the same manner described in (4) of Example 2, 1-(2,3-dihydro-1H-inden-1-yl)-2-[(E)-3-(2,6-dimethyl-4-morpholinyl)-3-oxo-1-propenyl]-4,6-diethyl-1H-pyrrolo[2,3-b]pyridine-3-carbonitrile was synthesized from (E)-3-[3-cyano-1-(2,3-dihydro-1H-inden-1-yl)-4,6-diethyl-1H-pyrrolo[2,3-b]pyridin-2-yl]-2-propenoic acid and 2,6-dimethylmorpholine.

Yield (amount) 14 mg LC-
MS(ESI-) analysis: Purity 96%, 483(M+H) (retention time: 2.61 minutes)

Example 42

(E)-3-[3-cyano-1-(2,3-dihydro-1H-inden-2-yl)-4,6-dimethyl-1H-pyrrolo[2,3-b]pyridin-2-yl]-N-(2,2-dimethyltetrahydro-2H-pyran-4-yl)-2-propenamide In the same manner described in (4) of Example 2, (E)-3-[3-cyano-1-(2,3-dihydro-1H-inden-2-yl)-4,6-dimethyl-1H-pyrrolo[2,3-b]pyridin-2-yl]-N-(2,2-dimethyltetrahydro-2H-pyran-4-yl)-2-propenamide was synthesized from (E)-3-[3-cyano-1-(2,3-dihydro-1H-inden-2-yl)-4,6-dimethyl-1H-pyrrolo[2,3-b]pyridin-2-yl]-2-propenoic acid and 2,2-dimethyltetrahydro-2H-pyran-4-ylamine.

Yield (amount) 19 mg LC-
MS(ESI-) analysis: Purity 92%, 459(M+H) (retention time: 2.36 minutes)

Example 43

(E)-3-[3-cyano-1-(2,3-dihydro-1H-inden-1-yl)-4,6-diisopropyl-1H-pyrrolo[2,3-b]pyridin-2-yl]-N-(2,2-dimethyltetrahydro-2H-pyran-4-yl)-2-propenamide (1) 1-(2,3-Dihydro-1H-inden-1-yl)-2-formyl-4,6-diisopropyl-1H-pyrrolo[2,3-b]pyridine-3-carbonitrile In the same manner described in (1) of Example 1, 1-(2,3-dihydro-1H-inden-1-yl)-2-formyl-4,6-diisopropyl-1H-pyrrolo[2,3-b]pyridine-3-carbonitrile was synthesized from 1-(2,3-dihydro-1H-inden-1-yl)-4,6-diisopropyl-1H-pyrrolo[2,3-b]pyridine-3-carbonitrile.

Yield (amount) 3.7 g, yield (rate) 99% $^1$H-NMR (CDCl$_3$) δ: 1.16-1.42 (12H, m), 2.62-2.80 (2H, m), 3.01-3.19 (2H, m), 3.40-3.52 (1H, m), 3.82-3.91 (1H, m), 6.77 (1H, d, J=7.8 Hz), 7.04-7.13 (2H, m), 7.20-7.37 (3H, m), 10.07 (1H, br)

(2) Ethyl (E)-3-[3-cyano-1-(2,3-dihydro-1H-inden-1-yl)-4,6-diisopropyl-1H-pyrrolo[2,3-b]pyridin-2-yl]-2-propenoate In the same manner described in (2) of Example 1, ethyl (E)-3-[3-cyano-1-(2,3-dihydro-1H-inden-1-yl)-4,6-diisopropyl-1H-pyrrolo[2,3-b]pyridin-2-yl]-2-propenoate was synthesized from 1-(2,3-dihydro-1H-inden-1-yl)-2-formyl-4,6-diisopropyl-1H-pyrrolo[2,3-b]pyridine-3-carbonitrile.

Yield (amount) 3.2 g, yield (rate) 71% $^1$H-NMR (CDCl$_3$) δ: 1.22-1.31 (9H, m), 1.39-1.43 (6H, m), 2.35-2.48 (1H, m), 2.75-2.85 (1H, m), 3.02-3.23 (2H, m), 3.36-3.42 (1H, m), 3.79-3.93 (1H, m), 4.17 (2H, dd, J=7.2 Hz, 14.2 Hz), 6.86-7.02 (4H, m), 7.11-7.41 (4H, m)

(3) (E)-3-[3-cyano-1-(2,3-dihydro-1H-inden-1-yl)-4,6-diisopropyl-1H-pyrrolo[2,3-b]pyridin-2-yl]-2-propenoic acid In the same manner described in (3) of Example 1, (E)-3-[3-cyano-1-(2,3-dihydro-1H-inden-1-yl)-4,6-diisopropyl-1H-pyrrolo[2,3-b]pyridin-2-yl]-2-propenoic acid was synthesized from ethyl (E)-3-[3-cyano-1-(2,3-dihydro-1H-inden-1-yl)-4,6-diisopropyl-1H-pyrrolo[2,3-b]pyridin-2-yl]-2-propenoate.

Yield (amount) 1.5 g, yield (rate) 92% $^1$H-NMR (CDCl$_3$) δ: 1.25-1.31 (6H, m), 1.40-1.43 (6H, m), 2.38-2.43 (1H, m), 2.79-2.91 (1H, m), 3.05-3.21 (2H, m), 3.33-3.43 (1H, m), 3.82-3.91 (1H, m), 6.86-6.91 (2H, m), 7.03 (1H, s), 7.14 (1H, t, J=7.2 Hz), 7.26-7.41 (4H, m)

(4) (E)-3-[3-cyano-1-(2,3-dihydro-1H-inden-1-yl)-4, 6-diisopropyl-1H-pyrrolo[2,3-b]pyridin-2-yl]-N-(2, 2-dimethyltetrahydro-2H-pyran-4-yl)-2-propenamide In the same manner described in (4) of Example 2, (E)-3-[3-cyano-1-(2,3-dihydro-1H-inden-1-yl)-4,6-diisopropyl-1H-pyrrolo[2,3-b]pyridin-2-yl]-N-(2,2-dimethyltetrahydro-2H-pyran-4-yl)-2-propenamide was synthesized from (E)-3-[3-cyano-1-(2,3-dihydro-1H-inden-1-yl)-4,6-diisopropyl-1H-pyrrolo[2,3-b]pyridin-2-yl]-2-propenoic acid and 2,2-dimethyltetrahydro-2H-pyran-4-ylamine.

Yield (amount) 23 mg LC-MS(ESI-) analysis: Purity 89%, 525(M+H) (retention time: 2.68 minutes)

Example 44

(E)-3-[3-cyano-1-(2,3-dihydro-1H-inden-1-yl)-4,6-diisopropyl-1H-pyrrolo[2,3-b]pyridin-2-yl]-N-methyl-N-tetrahydro-2H-pyran-4-yl-2-propenamide In the same manner described in (4) of Example 2, (E)-3-[3-cyano-1-(2,3-dihydro-1H-inden-1-yl)-4,6-diisopropyl-1H-pyrrolo[2,3-b]pyridin-2-yl]-N-methyl-N-tetrahydro-2H-pyran-4-yl-2-propenamide was synthesized from (E)-3-[3-cyano-1-(2,3-dihydro-1H-inden-1-yl)-4,6-diisopropyl-1H-pyrrolo[2,3-b]pyridin-2-yl]-2-propenoic acid and N-methyltetrahydro-2H-pyran-4-ylamine.

Yield (amount) 20 mg LC-MS(ESI-) analysis: Purity 84%, 511(M+H) (retention time: 2.67 minutes)

Example 45

(E)-3-[3-cyano-1-(2,3-dihydro-1H-inden-1-yl)-4,6-diisopropyl-1H-pyrrolo[2,3-b]pyridin-2-yl]-N-(3-pyridyl)-2-propenamide In the same manner described in (4) of Example 2, (E)-3-[3-cyano-1-(2,3-dihydro-1H-inden-1-yl)-4,6-diisopropyl-1H-pyrrolo[2,3-b]pyridin-2-yl]-N-(3-pyridyl)-2-propenamide was synthesized from (E)-3-[3-cyano-1-(2,3-dihydro-1H-inden-1-yl)-4,6-diisopropyl-1H-pyrrolo[2,3-b]pyridin-2-yl]-2-propenoic acid and 3-aminopyridine.

Yield (amount) 19 mg LC-MS(ESI-) analysis: Purity 87%, 490 (M+H) (retention time: 2.17 minutes)

Example 46

(E)-3-[3-cyano-1-(2,3-dihydro-1H-inden-1-yl)-4,6-diisopropyl-1H-pyrrolo[2,3-b]pyridin-2-yl]-N-(3-pyridyl)-2-propenamide In the same manner described in (4) of Example 2, (E)-3-[3-cyano-1-(2,3-dihydro-1H-inden-1-yl)-4,6-diisopropyl-1H-pyrrolo[2,3-b]pyridin-2-yl]-N-(3-pyridyl)-2-propenamide was synthesized from (E)-3-[3-cyano-1-(2,3-dihydro-1H-inden-1-yl)-4,6-diisopropyl-1H-pyrrolo[2,3-b]pyridin-2-yl]-2-propenoic acid and 4-aminopyridine.

Yield (amount) 19 mg LC-MS(ESI-) analysis: Purity 87%, 490(M+H) (retention time: 2.14 minutes)

Example 47

1-(2,3-Dihydro-1H-inden-1-yl)-4,6-diisopropyl-2-[(E)-3-(4-morpholinyl)-3-oxo-1-propenyl]-1H-pyrrolo[2,3-b]pyridine-3-carbonitrile In the same manner described in (4) of Example 2, 1-(2,3-dihydro-1H-inden-1-yl)-4,6-diisopropyl-2-[(E)-3-(4-morpholinyl)-3-oxo-1-propenyl]-1H-pyrrolo[2,3-b]pyridine-3-carbonitrile was synthesized from (E)-3-[3-cyano-1-(2,3-dihydro-1H-inden-1-yl)-4,6-diisopropyl-1H-pyrrolo[2,3-b]pyridin-2-yl]-2-propenoic acid and morpholine.

Yield (amount) 19 mg LC-MS(ESI-) analysis: Purity 88%, 483(M+H) (retention time: 2.61 minutes)

Example 48

1-(2,3-Dihydro-1H-inden-1-yl)-4,6-diisopropyl-2-[(E)-3-oxo-3-(4-thiomorpholinyl)-1-propenyl]-1H-pyrrolo[2,3-b]pyridine-3-carbonitrile In the same manner described in (4) of Example 2, 1-(2,3-dihydro-1H-inden-1-yl)-4,6-diisopropyl-2-[(E)-3-oxo-3-(4-thiomorpholinyl)-1-propenyl]-1H-pyrrolo[2,3-b]pyridine-3-carbonitrile was synthesized from (E)-3-[3-cyano-1-(2,3-dihydro-1H-inden-1-yl)-4,6-diisopropyl-1H-pyrrolo[2,3-b]pyridin-2-yl]-2-propenoic acid and thiomorpholine.

Yield (amount) 17 mg LC-MS(ESI-) analysis: Purity 100%, 499(M+H) (retention time: 2.72 minutes)

Example 49

1-(2,3-Dihydro-1H-inden-1-yl)-2-[(E)-3-(2,6-dimethyl-4-morpholinyl)-3-oxo-1-propenyl]-4,6-diisopropyl-1H-pyrrolo[2,3-b]pyridine-3-carbonitrile In the same manner described in (4) of Example 2, 1-(2,3-dihydro-1H-inden-1-yl)-2-[(E)-3-(2,6-dimethyl-4-morpholinyl)-3-oxo-1-propenyl]-4,6-diisopropyl-1H-pyrrolo[2,3-b]pyridine-3-carbonitrile was synthesized from (E)-3-[3-cyano-1-(2,3-dihydro-1H-inden-1-yl)-4,6-diisopropyl-1H-pyrrolo[2,3-b]pyridin-2-yl]-2-propenoic acid and 2,6-dimethylmorpholine.

Yield (amount) 17 mg LC-MS(ESI-) analysis: Purity 100%, 511(M+H) (retention time: 2.74 minutes)

Reference Example 9

1-(Indan-1-yl)-4,6-dimethyl-1H-pyrrolo[2,3-b]pyridine-3-carbonitrile

Formyl succinonitrile potassium salt (36.5 g) and 1-aminoindane (36.6 g) were dissolved in water (100 ml), and acetic acid (100 ml) was added thereto. After agitating the mixture at 100° C. for 30 minutes, the reaction solution was poured into water (1200 ml). The reaction mixture was made basic by adding potassium carbonate and then extracted with ethyl acetate. After the organic layer was washed with water and dried ($MgSO_4$), the solvent was distilled off under reduced pressure and the residue (37.4 g) was dissolved in ethanol (450 ml). After potassium ethoxide (35.2 g) was added thereto and the mixture was stirred at room temperature for 30 minutes, the reaction solution was poured into iced water (1500 ml) and extracted with ethyl acetate. After the organic layer was washed with water and dried ($MgSO_4$), the solvent was distilled off under reduced pressure. The residue was subjected to silica gel column chromatography eluting with ethyl acetate-hexane (1:2, v/v) and the fractions were concentrated under reduced pressure to give 2-amino-1-(indan-1-yl)pyrrole-4-carbonitrile (20.4 g, 37%) as oily matter.

To a solution of 2-amino-1-(indan-1-yl)pyrrole-4-carbonitrile (19.4 g), acetylacetone (9.6 g) and ethanol (375 ml) was added concentrated hydrochloric acid (3 ml), and the mixture was heated under reflux for 3 hours. The reaction solution was concentrated under reduced pressure and an aqueous sodium hydrogen carbonate solution was added to the residue, which was extracted with ethyl acetate. After the organic layer was washed with water and dried ($MgSO_4$), the solvent was distilled off under reduced pressure and the crystal was collected by filtration to give 1-(indan-1-yl)-4,6-dimethyl-1H-pyrrolo[2,3-b]pyridine-3-carbonitrile (11.4 g, 46%).

Various amines were appropriately selected as starting materials and the compounds of following Reference Examples 10 to 15 were synthesized by the same method as in Reference Example 9.

Reference Example 10

1-(2,2-Diphenylethyl)-4,6-dimethyl-1H-pyrrolo[2,3-b]pyridine-3-carbonitrile

Reference Example 11

1-Benzyl-4,6-dimethyl-1H-pyrrolo[2,3-b]pyridine-3-carbonitrile

Reference Example 12

4,6-Dimethyl-1-(2-thienylmethyl)-1H-pyrrolo[2,3-b]pyridine-3-carbonitrile

Reference Example 13

4,6-Dimethyl-1-(2-phenoxyethyl)-1H-pyrrolo[2,3-b]pyridine-3-carbonitrile

Reference Example 14

4,6-Dimethyl-1-(3-pyridylmethyl)-1H-pyrrolo[2,3-b]pyridine-3-carbonitrile

Reference Example 15

4,6-Dimethyl-1-(tetrahydro-2-furanylmethyl)-1H-pyrrolo[2,3-b]pyridine-3-carbonitrile

Example 50

(2E)-3-[3-cyano-1-(indan-1-yl)-4,6-dimethyl-1H-pyrrolo[2,3-b]pyridin-2-yl]-N-3-pyridylacrylamide (1) 3-Cyano-1-(indan-1-yl)-4,6-dimethyl-1H-pyrrolo[2,3-b]pyridine-2-carboxyaldehyde A lithium diisopropylamide solution was prepared from diisopropylamine (5.8 g), n-butyllithium (a 1.6 M hexane solution) (36.0 ml) and tetrahydrofuran (75 ml). A solution of 3-cyano-1-(indan-1-yl)-4,6-dimethyl-1H-pyrrolo[2,3-b]pyridine (11.0 g) in tetrahydrofuran (110 ml) was added dropwise at −78° C. After agitating at −78° C. for 30 minutes, N,N-dimethylformamide (8.4 g) was added thereto and the mixture was further stirred at room temperature for 1.5 hours. The reaction solution was poured into iced water (500 ml) and extracted with ethyl acetate. After the organic layer was washed with water and dried (over anhydrous magnesium sulfate), the solvent was distilled off under reduced pressure, and the crystal was collected by filtration to give 3-cyano-1-(indan-1-yl)-4,6-dimethyl-1H-pyrrolo[2,3-b]pyridine-2-carboxyaldehyde (10.8 g, 89%).

$^1$H-NMR (CDCl$_3$) δ: 2.57 (3H, s), 2.79 (3H, s), 3.04-3.20 (2H, m), 3.38-3.43 (2H, m), 6.75 (1H, d, J=8.0 Hz), 6.98 (1H, s), 7.08 (1H, t, J 7.0 Hz), 7.20 (1H, t, J=8.0 Hz), 7.22 (1H, d, J=8.0 Hz), 7.32 (1H, t, J=8.0 Hz), 9.90 (1H, s)

IR(KBr) cm$^{-1}$; 2222, 1672, 1497

(2) Ethyl (2E)-3-[3-cyano-1-(indan-1-yl)-4,6-dimethyl-1H-pyrrolo[2,3-b]pyridin-2-yl]acrylate 3-Cyano-1-(indan-1-yl)-4,6-dimethyl-1H-pyrrolo[2,3-b]pyridine-2-carboxyaldehyde (5.36 g) and triethyl phosphonoacetate (3.89 g) were dissolved in N,N-dimethylformamide (65 ml) and ice-cooled, and sodium hydride (60% in oil) (0.69 g) was added thereto. After agitating the mixture at room temperature for 40 minutes, the reaction solution was poured into iced water (350 ml) and extracted with ethyl acetate. After the organic layer was washed with water and dried (over anhydrous magnesium sulfate), the solvent was distilled off under reduced pressure and the crystal was collected by filtration to give ethyl (2E)-3-[3-cyano-1-(indan-1-yl)-4,6-dimethyl-1H-pyrrolo[2,3-b]pyridin-2-yl]acrylate (5.59 g, 85%).

$^1$H-NMR (CDCl$_3$) δ: 1.24 (3H, t, J=7.1 Hz), 2.20-3.41 (4H, m), 2.60 (3H, s), 2.76 (3H, s), 4.14 (2H, q, J=7.1 Hz), 6.81-7.41 (8H, m)

IR(KBr) cm$^{-1}$; 2213, 1721, 1632, 1184

HPLC (220 nm) Purity 96% (retention time 4.95 minutes)

MS(APCI+, m/e) 386 (M+1)

(3) (2E)-3-[3-cyano-1-(indan-1-yl)-4,6-dimethyl-1H-pyrrolo[2,3-b]pyridin-2-yl]acrylic acid Ethyl (2E)-3-[3-cyano-1-(indan-1-yl)-4,6-dimethyl-1H-pyrrolo[2,3-b]pyridin-2-yl]acrylate (5.54 g) was dissolved in ethanol-tetrahydrofuran (1 : 1, v/v) (60 ml) and a 2 N aqueous sodium hydroxide solution (14.4 ml) was added thereto at 50° C. After agitating the mixture at 50° C. for 40 minutes, the reaction solution was poured into water (300 ml), and concentrated hydrochloric acid was added thereto to adjust the pH to 3 to 4. The resultant mixture was extracted with ethyl acetate-tetrahydrofuran (3:1, v/v). After the organic layer was washed with water and dried (over anhydrous magnesium sulfate), the solvent was distilled off under reduced pressure and the crystal was collected by filtration to give (2E)-3-[3-cyano-1-(indan-1-yl)-4,6-dimethyl-1H-pyrrolo[2,3-b]pyridin-2-yl]acrylic acid (4.55 g, 89%).

$^1$H-NMR (CDCl$_3$) δ: 2.24-3.41 (4H, m), 2.61 (3H, s), 2.76 (3H, s), 6.78-7.41 (8H, m)

IR(KBr) cm$^{-1}$; 2951, 2213, 1688, 1628, 1433

HPLC (220 nm) Purity 98% (retention time 4.22 minutes)

MS(APCI−, m/e) 356 (M−1)

(4) (2E)-3-[3-cyano-1-(indan-1-yl)-4,6-dimethyl-1H-pyrrolo[2,3-b]pyridin-2-yl]-N-3-pyridylacrylamide (2E)-3-[3-cyano-1-(indan-1-yl)-4,6-dimethyl-1H-pyrrolo[2,3-b]pyridin-2-yl]acrylic acid (29 mg) was dissolved in tetrahydrofuran (0.3 ml), and N,N-dimethylformamide (0.5 µl) and oxalylchloride (13 mg) were added thereto, and the mixture was agitated at room temperature for 2 hours. The resultant solution was added to a solution of 3-aminopyridine (9 mg) and triethylamine (19 mg) in dichloromethane (0.8 ml) and the mixture was reacted with a FlexChem reactor at room temperature for 1 hour. After completion of the reaction, the mixture was treated at room temperature for 1.5 hours by adding a PS-isocyanate resin (from Argonaut company, 1.79 mmol/g) (70 mg). Further, it was treated at room temperature for 1 hour by adding an MP-carbonate resin (from Argonaut company, 3.20 mmol/g) (124 mg). The resin was removed by filtration and the filtrate was concentrated under reduced pressure (GeneVac) and the crystal was collected by filtration to give (2E)-3-[3-cyano-1-(indan-1-yl)-4,6-dimethyl-1H-pyrrolo[2,3-b]pyridin-2-yl]-N-3-pyridylacrylamide (29 mg, 84%).

HPLC (220 nm) Purity 98% (retention time 3.61 minutes)
MS(APCI+, m/e) 434 (M+1)

Example 51

(2E)-3-[3-cyano-1-(indan-1-yl)-4,6-dimethyl-1H-pyrrolo[2,3-b]pyridin-2-yl]-N-(2,2-dimethyltetrahydro-2H-pyran-4-yl)acrylamide In the same manner described in (4) of Example 50, (2E)-3-[3-cyano-1-(indan-1-yl)-4,6-dimethyl-1H-pyrrolo[2,3-b]pyridin-2-yl]-N-(2,2-dimethyltetrahydro-2H-pyran-4-yl)acrylamide was synthesized from (2E)-3-[3-cyano-1-(indan-1-yl)-4,6-dimethyl-1H-pyrrolo[2,3-b]pyridin-2-yl]acrylic acid and 2,2-dimethyltetrahydro-2H-pyran-4-ylamine.
HPLC (220 nm) purity 94% (retention time 4.47 minutes)
MS(APCI+, m/e) 469 (M+1)

Example 52

1-(Indan-1-yl)-4,6-dimethyl-2-[(1E)-3-morpholino-3-oxo-1-propenyl]-1H-pyrrolo[2,3-b]pyridine-3-carbonitrile In the same manner described in (4) of Example 50, 1-(indan-1-yl)-4,6-dimethyl-2-[(1E)-3-morpholino-3-oxo-1-propenyl]-1H-pyrrolo[2,3-b]pyridine-3-carbonitrile was synthesized from (2E)-3-[3-cyano-1-(indan-1-yl)-4,6-dimethyl-1H-pyrrolo[2,3-b]pyridin-2-yl]acrylic acid and morpholine.
HPLC (220 nm) purity 97% (retention time 4.27 minutes)
MS(APCI+, m/e) 427 (M+1)

Example 53

(2E)-3-[3-cyano-1-(2,2-diphenylethyl)-4,6-dimethyl-1H-pyrrolo[2,3-b]pyridin-2-yl]-N-3-pyridylacrylamide (1) 3-Cyano-1-(2,2-diphenylethyl)-4,6-dimethyl-1H-pyrrolo[2,3-b]pyridine-2-carboxyaldehyde In the same manner described in (1) of Example 50, 3-cyano-1-(2,2-diphenylethyl)-4,6-dimethyl-1H-pyrrolo[2,3-b]pyridine-2-carboxyaldehyde was synthesized from 1-(2,2-diphenylethyl)-4,6-dimethyl-1H-pyrrolo[2,3-b]pyridine-3-carbonitrile.
$^1$H-NMR (CDCl$_3$) δ: 2.59 (3H, s), 2.70 (3H, s), 4.69 (1H, d, J=8.2 Hz), 5.37 (2H, d, J=8.2 Hz), 6.90 (1H, s), 7.08-7.30 (10H, m), 9.94 (1H, s)
IR(KBr) cm$^{-1}$; 3029, 2841, 2222, 1682, 1588, 1505, 1462

(2) Ethyl (2E)-3-[3-cyano-1-(2,2-diphenylethyl)-4,6-dimethyl-1H-pyrrolo[2,3-b]pyridin-2-yl]acrylate In the same manner described in (2) of Example 50, 3-cyano-1-(2,2-diphenylethyl)-4,6-dimethyl-1H-pyrrolo[2,3-b]pyridine-2-carboxyaldehyde.
HPLC (220 nm) purity 96% (retention time 5.04 minutes)
MS(APCI+, m/e) 450 (M+1)

(3) (2E)-3-[3-cyano-1-(2,2-diphenylethyl)-4,6-dimethyl-1H-pyrrolo[2,3-b]pyridin-2-yl]acrylic acid In the same manner described in (3) of Example 50, (2E)-3-[3-cyano-1-(2,2-diphenylethyl)-4,6-dimethyl-1H-pyrrolo[2,3-b]pyridin-2-yl]acrylic acid was synthesized from ethyl (2E)-3-[3-cyano-1-(2,2-diphenylethyl)-4,6-dimethyl-1H-pyrrolo[2,3-b]pyridin-2-yl]acrylate.
HPLC (220 nm) purity 98% (retention time 4.41 minutes)
MS(APCI−, m/e) 420 (M−1)

(4) (2E)-3-[3-cyano-1-(2,2-diphenylethyl)-4,6-dimethyl-1H-pyrrolo[2,3-b]pyridin-2-yl]-N-3-pyridylacrylamide In the same manner described in (4) of Example 50, (2E)-3-[3-cyano-1-(2,2-diphenylethyl)-4,6-dimethyl-1H-pyrrolo[2,3-b]pyridin-2-yl]-N-3-pyridylacrylamide was synthesized from (2E)-3-[3-cyano-1-(2,2-diphenylethyl)-4,6-dimethyl-1H-pyrrolo[2,3-b]pyridin-2-yl]acrylic acid and 3-pyridylamine.
HPLC (220 nm) purity 98% (retention time 3.82 minutes)
MS(APCI+, m/e) 498 (M+1)

Example 54

(2E)-3-[3-cyano-1-(2,2-diphenylethyl)-4,6-dimethyl-1H-pyrrolo[2,3-b]pyridin-2-yl]-N-(2,2-dimethyltetrahydro-2H-pyran-4-yl)acrylamide In the same manner described in (4) of Example 50, (2E)-3-[3-cyano-1-(2,2-diphenylethyl)-4,6-dimethyl-1H-pyrrolo[2,3-b]pyridin-2-yl]-N-(2,2-dimethyltetrahydro-2H-pyran-4-yl)acrylamide was synthesized from (2E)-3-[3-cyano-1-(2,2-diphenylethyl)-4,6-dimethyl-1H-pyrrolo[2,3-b]pyridin-2-yl]acrylic acid and 2,2-dimethyltetrahydro-2H-pyran-4-ylamine.
HPLC (220 nm) purity 87% (retention time 4.58 minutes)
MS(APCI+, m/e) 533 (M+1)

Example 55

1-(2,2-Diphenylethyl)-4,6-dimethyl-2-[(1E)-3-morpholino-3-oxo-1-propenyl]-1H-pyrrolo[2,3-b]pyridine-3-carbonitrile In the same manner described in (4) of Example 50, 1-(2,2-diphenylethyl)-4,6-dimethyl-2-[(1E)-3-morpholino-3-oxo-1-propenyl]-1H-pyrrolo[2,3-b]pyridine-3-carbonitrile was synthesized from (2E)-3-[3-cyano-1-(2,2-diphenylethyl)-4,6-dimethyl-1H-pyrrolo[2,3-b]pyridin-2-yl]acrylic acid and morpholine.

HPLC (220 nm) purity 100% (retention time 4.48 minutes)
MS(APCI+, m/e) 491 (M+1)

Example 56

(2E)-3-[1-benzyl-3-cyano-4,6-dimethyl-1H-pyrrolo[2,3-b]pyridin-2-yl]-N-3-pyridylacrylamide

(1) 1-Benzyl-3-cyano-4,6-dimethyl-1H-pyrrolo[2,3-b]pyridine-2-carboxyaldehyde In the same manner described in (1) of Example 50, 1-benzyl-3-cyano-4,6-dimethyl-1H-pyrrolo[2,3-b]pyridine-2-carboxyaldehyde was synthesized from 1-benzyl-4,6-dimethyl-1H-pyrrolo[2,3-b]pyridine-3-carbonitrile.

$^1$H-NMR (CDCl$_3$) δ: 2.66 (3H, s), 2.77 (3H, s), 5.93 (2H, s), 7.00 (1H, s), 7.22-7.31 (5H, m), 10.14 (1H, s)

IR(KBr) cm$^{-1}$; 2220, 1676, 1588, 1456, 694

(2) Ethyl (2E)-3-[1-benzyl-3-cyano-4,6-dimethyl-1H-pyrrolo[2,3-b]pyridin-2-yl]acrylate In the same manner described in (2) of Example 50, ethyl (2E)-3-[1-benzyl-3-cyano-4,6-dimethyl-1H-pyrrolo[2,3-b]pyridin-2-yl]acrylate was synthesized from 1-benzyl-3-cyano-4,6-dimethyl-1H-pyrrolo[2,3-b]pyridine-2-carboxyaldehyde.

HPLC (220 nm) purity 94% (retention time 4.67 minutes)
MS(APCI+, m/e) 360 (M+1)

(3) (2E)-3-[1-benzyl-3-cyano-4,6-dimethyl-1H-pyrrolo[2,3-b]pyridin-2-yl]acrylic acid HPLC (220 nm) purity 93% (retention time 3.97 minutes)
MS(APCI-, m/e) 330 (M-1)

(4) (2E)-3-[1-benzyl-3-cyano-4,6-dimethyl-1H-pyrrolo[2,3-b]pyridin-2-yl]-N-3-pyridylacrylamide In the same manner described in (4) of Example 50, (2E)-3-[1-benzyl-3-cyano-4,6-dimethyl-1H-pyrrolo[2,3-b]pyridin-2-yl]-N-3-pyridylacrylamide was synthesized from (2E)-3-[1-benzyl-3-cyano-4,6-dimethyl-1H-pyrrolo[2,3-b]pyridin-2-yl]acrylic acid and 3-pyridine.

HPLC (220 nm) purity 94% (retention time 3.42 minutes)
MS(APCI+, m/e) 408 (M+1)

Example 57

(2E)-3-[1-benzyl-3-cyano-4,6-dimethyl-1H-pyrrolo[2,3-b]pyridin-2-yl]-N-(2,2-dimethyltetrahydro-2H-pyran-4-yl)acrylamide In the same manner described in (4) of Example 50, (2E)-3-[1-benzyl-3-cyano-4,6-dimethyl-1H-pyrrolo[2,3-b]pyridin-2-yl]-N-(2,2-dimethyltetrahydro-2H-pyran-4-yl)acrylamide was synthesized from (2E)-3-[1-benzyl-3-cyano-4,6-dimethyl-1H-pyrrolo[2,3-b]pyridin-2-yl]acrylic acid and 2,2-dimethyltetrahydro-2H-pyran-4-ylamine.

HPLC (220 nm) purity 88% (retention time 4.17 minutes)
MS(APCI+, m/e) 443 (M+1)

Example 58

1-Benzyl-4,6-dimethyl-2-[(1E)-3-morpholino-3-oxo-1-propenyl]-1H-pyrrolo[2,3-b]pyridine-3-carbonitrile In the same manner described in (4) of Example 50, 1-benzyl-4,6-dimethyl-2-[(1E)-3-morpholino-3-oxo-1-propenyl]-1H-pyrrolo[2,3-b]pyridine-3-carbonitrile was synthesized from (2E)-3-[1-benzyl-3-cyano-4,6-dimethyl-1H-pyrrolo[2,3-b]pyridin-2-yl]acrylic acid and morpholine.

HPLC (220 nm) purity 96% (retention time 3.99 minutes)
MS(APCI+, m/e) 401 (M+1)

Example 59

(2E)-3-[3-cyano-4,6-dimethyl-1-(2-thienylmethyl)-1H-pyrrolo[2,3-b]pyridin-2-yl]-N-3-pyridylacrylamide

(1) 3-Cyano-4,6-dimethyl-1-(2-thienylmethyl)-1H-pyrrolo[2,3-b]pyridine-2-carboxyaldehyde In the same manner described in (1) of Example 50, 3-cyano-4,6-dimethyl-1-(2-thienylmethyl)-1H-pyrrolo[2,3-b]pyridine-2-carboxyaldehyde was synthesized from 4,6-dimethyl-1-(2-thienylmethyl)-1H-pyrrolo[2,3-b]pyridine-3-carbonitrile.

$^1$H-NMR (CDCl$_3$) δ: 2.69 (3H, s), 2.75 (3H, s), 6.09 (2H, s), 6.88 (1H, dd, J=5.0, 4.0 Hz), 7.00 (1H, s), 7.16 (1H, dd, J=5.0, 1.0 Hz), 7.19-7.21 (1H, m), 10.19 (1H, s)

IR(KBr) cm$^{-1}$; 2222, 1674, 1590, 1458

(2) Ethyl (2E)-3-[3-cyano-4,6-dimethyl-1-(2-thienylmethyl)-1H-pyrrolo[2,3-b]pyridin-2-yl]acrylate In the same manner described in (2) of Example 50, ethyl (2E)-3-[3-cyano-4,6-dimethyl-1-(2-thienylmethyl)-1H-pyrrolo[2,3-b]pyridin-2-yl]acrylate was synthesized from 3-cyano-4,6-dimethyl-1-(2-thienylmethyl)-1H-pyrrolo[2,3-b]pyridine-2-carboxyaldehyde.

HPLC (220 nm) purity 93% (retention time 4.60 minutes)
MS(APCI+, m/e) 366 (M+1)

(3) (2E)-3-[3-cyano-4,6-dimethyl-1-(2-thienylmethyl)-1H-pyrrolo[2,3-b]pyridin-2-yl]acrylic acid In the same manner described in (3) of Example 50, (2E)-3-[3-cyano-4,6-dimethyl-1-(2-thienylmethyl)-1H-pyrrolo[2,3-b]pyridin-2-yl]acrylic acid was synthesized from ethyl (2E)-3-[3-cyano-4,6-dimethyl-1-(2-thienylmethyl)-1H-pyrrolo[2,3-b]pyridin-2-yl]acrylate.

HPLC (220 nm) purity 95% (retention time 3.89 minutes)
MS(APCI-, m/e) 336 (M-1)

(4) (2E)-3-[3-cyano-4,6-dimethyl-1-(2-thienylmethyl)-1H-pyrrolo[2,3-b]pyridin-2-yl]-N-3-pyridylacrylamide In the same manner described in (4) of Example 50, (2E)-3-[3-cyano-4,6-dimethyl-1-(2-thienylmethyl)-1H-pyrrolo[2,3-b]pyridin-2-yl]-N-3-pyridylacrylamide was synthesized from (2E)-3-[3-cyano-4,6-dimethyl-1-(2-thienylmethyl)-1H-pyrrolo[2,3-b]pyridin-2-yl]acrylic acid and 3-pyridine.

HPLC (220 nm) purity 84% (retention time 3.34 minutes)
MS(APCI+, m/e) 414 (M+1)

Example 60

(2E)-3-[3-cyano-4,6-dimethyl-1-(2-thienylmethyl)-1H-pyrrolo[2,3-b]pyridin-2-yl]-N-(2,2-dimethyltetrahydro-2H-pyran-4-yl)acrylamide In the same manner described in (4) of Example 50, (2E)-3-[3-cyano-4,6-dimethyl-1-(2-thienylmethyl)-1H-pyrrolo[2,3-b]pyridin-2-yl]-N-(2,2-dimethyltetrahydro-2H-pyran-4-yl)acrylamide was synthesized from (2E)-3-[3-cyano-4,6-dimethyl-1-(2-thienylmethyl)-1H-pyrrolo[2,3-b]pyridin-2-yl]acrylic acid and 2,2-dimethyltetrahydro-2H-pyran-4-ylamine.

HPLC (220 nm) purity 88% (retention time 4.11 minutes)
MS(APCI+, m/e) 449 (M+1)

Example 61

4,6-Dimethyl-2-[(1E)-3-morpholino-3-oxo-1-propenyl]-1-(2-thienylmethyl)-1H-pyrrolo[2,3-b]pyridine-3-carbonitrile In the same manner described in (4) of Example 50, 4,6-dimethyl-2-[(1E)-3-morpholino-3-oxo-1-propenyl]-1-(2-thienylmethyl)-1H-pyrrolo[2,3-b]pyridine-3-carbonitrile was synthesized from (2E)-3-[3-cyano-4,6-dimethyl-1-(2-thienylmethyl)-1H-pyrrolo[2,3-b]pyridin-2-yl]acrylic acid and morpholine.

HPLC (220 nm) purity 92% (retention time 3.89 minutes)
MS(APCI+, m/e) 407 (M+1)

Example 62

(2E)-3-[3-cyano-4,6-dimethyl-1-(2-phenoxyethyl)-1H-pyrrolo[2,3-b]pyridin-2-yl]-N-3-pyridylacrylamide

(1) 3-Cyano-4,6-dimethyl-1-(2-phenoxyethyl)-1H-pyrrolo[2,3-b]-pyridine-2-carboxyaldehyde In the same manner described in (1) of Example 50, 3-cyano-4,6-dimethyl-1-(2-phenoxyethyl)-1H-pyrrolo[2,3-b]-pyridine-2-carboxyaldehyde was synthesized from 4,6-dimethyl-1-(2-phenoxyethyl)-1H-pyrrolo[2,3-b]pyridine-3-carbonitrile.

$^1$H-NMR (CDCl$_3$) δ: 2.63 (3H, s), 2.76 (3H, s), 4.32 (2H, t, J=6.0 Hz), 5.16 (2H, t, J=6.0 Hz), 6.76-6.81 (2H, m), 6.88-6.95 (1H, m), 6.99 (1H, s), 7.17-7.23 (2H, m), 10.23 (1H, s)
IR(KBr) cm$^{-1}$; 2226, 1672, 1586, 1501, 1466, 1252

(2) Ethyl (2E)-3-[3-cyano-4,6-dimethyl-1-(2-phenoxyethyl)-1H-pyrrolo[2,3-b]pyridin-2-yl]acrylate In the same manner described in (2) of Example 50, ethyl (2E)-3-[3-cyano-4,6-dimethyl-1-(2-phenoxyethyl)-1H-pyrrolo[2,3-b]pyridin-2-yl]acrylate was synthesized from 3-cyano-4,6-dimethyl-1-(2-phenoxyethyl)-1H-pyrrolo[2,3-b]pyridine-2-carboxyaldehyde.

HPLC (220 nm) purity 94% (retention time 4.66 minutes)
MS(APCI+, m/e) 390 (M+1)

(3) (2E)-3-[3-cyano-4,6-dimethyl-1-(2-phenoxyethyl)-1H-pyrrolo[2,3-b]pyridin-2-yl]acrylic acid In the same manner described in (3) of Example 50, (2E)-3-[3-cyano-4,6-dimethyl-1-(2-phenoxyethyl)-1H-pyrrolo[2,3-b]pyridin-2-yl]acrylic acid was synthesized from ethyl (2E)-3-[3-cyano-4,6-dimethyl-1-(2-phenoxyethyl)-1H-pyrrolo[2,3-b]pyridin-2-yl]acrylate.

HPLC (220 nm) purity 95% (retention time 3.95 minutes)
MS(APCI−, m/e) 360 (M−1)

(4) (2E)-3-[3-cyano-4,6-dimethyl-1-(2-phenoxyethyl)-1H-pyrrolo[2,3-b]pyridin-2-yl]-N-3-pyridylacrylamide In the same manner described in (4) of Example 50, (2E)-3-[3-cyano-4,6-dimethyl-1-(2-phenoxyethyl)-1H-pyrrolo[2,3-b]pyridin-2-yl]-N-3-pyridylacrylamide was synthesized from (2E)-3-[3-cyano-4,6-dimethyl-1-(2-phenoxyethyl)-1H-pyrrolo[2,3-b]pyridin-2-yl]acrylic acid and 3-pyridine.

HPLC (220 nm) purity 82% (retention time 3.41 minutes)
MS(APCI+, m/e) 438 (M+1)

Example 63

(2E)-3-[3-cyano-4,6-dimethyl-1-(2-phenoxyethyl)-1H-pyrrolo[2,3-b]pyridin-2-yl]-N-(2,2-dimethyltetrahydro-2H-pyran-4-yl)acrylamide In the same manner described in (4) of Example 50, (2E)-3-[3-cyano-4,6-dimethyl-1-(2-phenoxyethyl)-1H-pyrrolo[2,3-b]pyridin-2-yl]-N-(2,2-dimethyltetrahydro-2H-pyran-4-yl)acrylamide was synthesized from (2E)-3-[3-cyano-4,6-dimethyl-1-(2-phenoxyethyl)-1H-pyrrolo[2,3-b]pyridin-2-yl]acrylic acid and 2,2-dimethyltetrahydro-2H-pyran-4-ylamine.

HPLC (220 nm) purity 92% (retention time 4.12 minutes)
MS(APCI+, m/e) 473 (M+1)

Example 64

4,6-Dimethyl-2-[(1E)-3-morpholino-3-oxo-1-propenyl]-1-(2-phenoxyethyl)-1H-pyrrolo[2,3-b]pyridine-3-carbonitrile In the same manner described in (4) of Example 50, 4,6-dimethyl-2-[(1E)-3-morpholino-3-oxo-1-propenyl]-1-(2-phenoxyethyl)-1H-pyrrolo[2,3-b]pyridine-3-carbonitrile was synthesized from (2E)-3-[3-cyano-4,6-dimethyl-1-(2-phenoxyethyl)-1H-pyrrolo[2,3-b]pyridin-2-yl]acrylic acid and morpholine.

HPLC (220 nm) purity 96% (retention time 3.96 minutes)
MS(APCI+, m/e) 431 (M+1)

Example 65

(2E)-3-[3-cyano-4,6-dimethyl-1-(3-pyridylmethyl)-1H-pyrrolo[2,3-b]pyridin-2-yl]-N-3-pyridylacrylamide

(1) 3-Cyano-4,6-dimethyl-1-(3-pyridylmethyl)-1H-pyrrolo[2,3-b]pyridine-2-carboxyaldehyde In the same manner described in (1) of Example 50, 3-cyano-4,6-dimethyl-1-(3-pyridylmethyl)-1H-pyrrolo[2,3-b]pyridine-2-carboxyaldehyde was synthesized from 4,6-dimethyl-1-(3-pyridylmethyl)-1H-pyrrolo[2,3-b]pyridine-3-carbonitrile.

$^1$H-NMR (CDCl$_3$) δ: 2.67 (3H, s), 2.77 (3H, s), 5.94 (2H, s), 7.03 (1H, s), 7.20 (1H, dd, J=8.0, 5.0 Hz), 7.71 (1H, dt, J=8.0, 2.0 Hz), 8.49 (1H, dd, J=5.0, 2.0 Hz), 8.70 (1H, d, J=2 Hz), 10.16 (1H, s)
IR(KBr) cm$^{-1}$; 2222, 1674, 1590, 1460

(2) Ethyl (2E)-3-[3-cyano-4,6-dimethyl-1-(3-pyridylmethyl)-1H-pyrrolo[2,3-b]pyridin-2-yl]acrylate In the same manner described in (2) of Example 50, ethyl (2E)-3-[3-cyano-4,6-dimethyl-1-(3-pyridylmethyl)-1H-pyrrolo[2,3-b]pyridin-2-yl]acrylate was synthesized from 3-cyano-4,6-dimethyl-1-(3-pyridylmethyl)-1H-pyrrolo[2,3-b]pyridine-2-carboxyaldehyde.
HPLC (220 nm) purity 92% (retention time 3.05 minutes)
MS(APCI+, m/e) 361 (M+1)

(3) (2E)-3-[3-cyano-4,6-dimethyl-1-(3-pyridylmethyl)-1H-pyrrolo[2,3-b]pyridin-2-yl]acrylic acid In the same manner described in (3) of Example 50, (2E)-3-[3-cyano-4,6-dimethyl-1-(3-pyridylmethyl)-1H-pyrrolo[2,3-b]pyridin-2-yl]acrylic acid was synthesized from ethyl (2E)-3-[3-cyano-4,6-dimethyl-1-(3-pyridylmethyl)-1H-pyrrolo[2,3-b]pyridin-2-yl]acrylate.
HPLC (220 nm) purity 98% (retention time 2.64 minutes)
MS(APCI−, m/e) 331 (M−1)

(4) (2E)-3-[3-cyano-4,6-dimethyl-1-(3-pyridylmethyl)-1H-pyrrolo[2,3-b]pyridin-2-yl]-N-3-pyridylacrylamide In the same manner described in (4) of Example 50, (2E)-3-[3-cyano-4,6-dimethyl-1-(3-pyridylmethyl)-1H-pyrrolo[2,3-b]pyridin-2-yl]-N-3-pyridylacrylamide was synthesized from (2E)-3-[3-cyano-4,6-dimethyl-1-(3-pyridylmethyl)-1H-pyrrolo[2,3-b]pyridin-2-yl]acrylic acid and 3-pyridine.
HPLC (220 nm) purity 89% (retention time 2.43 minutes)
MS(APCI+, m/e) 409 (M+1)

Example 66

(2E)-3-[3-cyano-4,6-dimethyl-1-(3-pyridylmethyl)-1H-pyrrolo[2,3-b]pyridin-2-yl]-N-(2,2-dimethyltetrahydro-2H-pyran-4-yl)acrylamide In the same manner described in (4) of Example 50, (2E)-3-[3-cyano-4,6-dimethyl-1-(3-pyridylmethyl)-1H-pyrrolo[2,3-b]pyridin-2-yl]-N-(2,2-dimethyltetrahydro-2H-pyran-4-yl)acrylamide was synthesized from (2E)-3-[3-cyano-4,6-dimethyl-1-(3-pyridylmethyl)-1H-pyrrolo[2,3-b]pyridin-2-yl]acrylic acid and 2,2-dimethyltetrahydro-2H-pyran-4-ylamine.
HPLC (220 nm) purity 93% (retention time 2.81 minutes)
MS(APCI+, m/e) 444 (M+1)

Example 67

(2E)-3-[3-cyano-4,6-dimethyl-1-(tetrahydro-2-furanylmethyl)-1H-pyrrolo[2,3-b]pyridin-2-yl]-N-3-pyridylacrylamide

(1) 3-Cyano-4,6-dimethyl-1-(tetrahydro-2-furanylmethyl)-1H-pyrrolo[2,3-b]pyridine-2-carboxyaldehyde In the same manner described in (1) of Example 50, 3-cyano-4,6-dimethyl-1-(tetrahydro-2-furanylmethyl)-1H-pyrrolo[2,3-b]pyridine-2-carboxyaldehyde was synthesized from 4,6-dimethyl-1-(tetrahydro-2-furanylmethyl)-1H-pyrrolo[2,3-b]pyridine-3-carbonitrile.
$^1$H-NMR (CDCl$_3$) δ: 1.66-2.09 (4H, m), 2.62 (3H, s), 2.76 (3H, s), 3.63-3.89 (2H, m), 4.30-4.38 (1H, m), 4.65 (1H, dd, J=13.0, 4.0 Hz), 4.89 (1H, dd, J=13.0, 9.0 Hz), 6.96 (1H, s), 10.19 (1H, s)
IR(KBr) cm$^{-1}$; 2224, 1680, 1586, 1462

(2) Ethyl (2E)-3-[3-cyano-4,6-dimethyl-1-(tetrahydro-2-furanylmethyl)-1H-pyrrolo[2,3-b]pyridin-2-yl]acrylate In the same manner described in (2) of Example 50, ethyl (2E)-3-[3-cyano-4,6-dimethyl-1-(tetrahydro-2-furanylmethyl)-1H-pyrrolo[2,3-b]pyridin-2-yl]acrylate was synthesized from 3-cyano-4,6-dimethyl-1-(tetrahydro-2-furanylmethyl)-1H-pyrrolo[2,3-b]pyridine-2-carboxyaldehyde.
HPLC (220 nm) purity 95% (retention time 4.26 minutes)
MS(APCI+, m/e) 354 (M+1)

(3) (2E)-3-[3-cyano-4,6-dimethyl-1-(tetrahydro-2-furanylmethyl)-1H-pyrrolo[2,3-b]pyridin-2-yl]acrylic acid In the same manner described in (3) of Example 50, (2E)-3-[3-cyano-4,6-dimethyl-1-(tetrahydro-2-furanylmethyl)-1H-pyrrolo[2,3-b]pyridin-2-yl]acrylic acid was synthesized from ethyl (2E)-3-[3-cyano-4,6-dimethyl-1-(tetrahydro-2-furanylmethyl)-1H-pyrrolo[2,3-b]pyridin-2-yl]acrylate.
HPLC (220 nm) purity 96% (retention time 3.48 minutes)
MS(APCI−, m/e) 324 (M−1) tk

(4) (2E)-3-[3-cyano-4,6-dimethyl-1-(tetrahydro-2-furanylmethyl)-1H-pyrrolo[2,3-b]pyridin-2-yl]-N-3-pyridylacrylamide In the same manner described in (4) of Example 50, (2E)-3-[3-cyano-4,6-dimethyl-1-(tetrahydro-2-furanylmethyl)-1H-pyrrolo[2,3-b]pyridin-2-yl]acrylic acid and 3-pyridine.
HPLC (220 nm) purity 93% (retention time 3.02 minutes)
MS(APCI+, m/e) 402 (M+1)

Example 68

(2E)-3-[3-cyano-4,6-dimethyl-1-(tetrahydro-2-furanylmethyl)-1H-pyrrolo[2,3-b]pyridin-2-yl]-N-(2,2-dimethyltetrahydro-2H-pyran-4-yl)acrylamide In the same manner described in (4) of Example 50, (2E)-3-[3-cyano-4,6-dimethyl-1-(tetrahydro-2-furanylmethyl)-1H-pyrrolo[2,3-b]pyridin-2-yl]-N-(2,2-dimethyltetrahydro-2H-pyran-4-yl)acrylamide was synthesized from (2E)-3-[3-cyano-4,6-dimethyl-1-(tetrahydro-2-furanylmethyl)-1H-pyrrolo[2,3-b]pyridin-2-yl]acrylic acid and 2,2-dimethyltetrahydro-2H-pyran-4-ylamine.
HPLC (220 nm) purity 88% (retention time 3.63 minutes)
MS(APCI+, m/e) 437 (M+1)

Example 69

4,6-Dimethyl-2-[(1E)-3-morpholino-3-oxo-1-propenyl]-1-(tetrahydro-2-furanylmethyl)-1H-pyrrolo[2,3-b]pyridine-3-carbonitrile In the same manner described in (4) of Example 50, 4,6-dimethyl-2-[(1E)-3-morpholino-3-oxo-1-propenyl]-1-(tetrahydro-2-furanylmethyl)-1H-pyrrolo[2,3-b]pyridine-3-carbonitrile was synthesized from (2E)-3-[3-cyano-4,6-dimethyl-1-(tetrahydro-2-furanylmethyl)-1H-pyrrolo[2,3-b]pyridin-2-yl]acrylic acid and morpholine.
HPLC (220 nm) purity 92% (retention time 3.42 minutes)
MS(APCI+, m/e) 395 (M+1)

Reference Example 16

1-Benzhydryl-4,6-dimethyl-1H-pyrrolo[2,3-b]pyridine-3-carbonitrile (1) Formyl succinonitrile potassium salt To a mixed solution of succinonitrile (50.0 g, 656 mmol), ethyl formate (50.9 g, 687 mmol), tert-butanol (60 ml) and toluene (600 ml) was slowly added potassium tert-butoxide (73.6 g, 656 mmol) under ice-cooling, and the mixture was stirred at room temperature for 4 hours. Precipitates were filtered off and washed with ethanol-ether (1:1).
Yield (amount) 83.0 g, yield (rate) 91.2% $^1$H-NMR (DMSO-$d_6$) δ: 3.03 (2H, s), 8.24 (0.8H, s), 8.55 (0.2 H, s).

(2) 1-Benzhydryl-4,6-dimethyl-1H-pyrrolo[2,3-b]pyridine-3-carbonitrile

To a solution of formyl succinonitrile potassium salt (10.5 g, 72.0 mmol) and amino diphenylmethane (14.5 g, 79.2 mmol) in water (30 ml) was added acetic acid (30 ml) at room temperature. The mixture was stirred at 100° C. for 30 minutes and poured into iced water. The reaction mixture was made basic with potassium carbonate and then extracted with ethyl acetate. The extract was washed with water, dried over anhydrous magnesium sulfate and the solvent was distilled off under reduced pressure to give an oily matter.
To a solution of the oily matter in tetrahydrofuran (75 ml) and ethanol (75 ml) was slowly added potassium ethoxide (10.5 g, 125 mmol). The mixture was stirred at room temperature for 1 hour and poured into iced water. The resultant mixture was extracted with ethyl acetate, the extract was washed with water, dried over anhydrous magnesium sulfate and the solvent was distilled off under reduced pressure to yield an oily matter. To a solution of the oily matter in ethanol (75 ml) was sequentially added acetylacetone (5.86 g, 58.6 mmol) and concentrated hydrochloric acid (2.0 ml), the mixture was heated under reflux for 3 hours, poured into saturated sodium bicarbonate solution and extracted with ethyl acetate. The extract was washed with water, dried over anhydrous magnesium sulfate and the solvent was distilled off under reduced pressure. The residue was recrystallized from ethyl acetate.
Yield (amount) 7.44 g, yield (rate) 31.8% $^1$H-NMR (CDCl$_3$) δ: 2.55 (3H, s), 2.72 (3H, s), 6.88 (1H, s), 7.08-7.49 (12H, m)
IR(KBr) cm$^{-1}$; 2220, 1586, 1524, 1449, 1410, 1395, 1188, 750, 733, 700.

Reference Example 17

Tetrahydro-2H-pyran-4-ylamine hydrochloride

To a solution of tetrahydro-4H-pyran-4-one (4.30 g, 43.0 mmol) in methanol (112 ml) was added an aqueous solution (12.5 ml) of ammonium formate (25 g, 400 mmol). Insolubles were completely dissolved and then 10% palladium carbon (5.1 g) was added thereto, which was stirred at room temperature overnight. After the insolubles were filtrated off to obtain a filtrate, which was concentrated, and to the residue was added ethanol (100 ml) and concentrated hydrochloric acid (7.5 ml). The solvent was distilled off under reduced pressure to give an objective product, which was collected by filtration and washed with ether.
$^1$H-NMR (DMSO-$d_6$) δ: 1.54-1.74 (2H, m), 1.82-1.98 (2H, m), 3.27-3.38 (3H, m), 3.87-3.94 (2H, m), 9.05 (3H, bs).
IR(KBr) cm$^{-1}$; 2966, 1377, 1163, 1088, 1015, 986, 862.

Example 70

(2E)-3-(1-benzhydryl-3-cyano-4,6-dimethyl-1H-pyrrolo[2,3-b]pyridin-2-yl)-N-(3,3-dimethylbutyl)prop-2-enamide (1) 1-Benzhydryl-2-formyl-4,6-dimethyl-1H-pyrrolo[2,3-b]pyridine-3-carbonitrile To a solution of diisopropylamine (1.21 ml, 9.26 mmol) in tetrahydrofuran (12 ml) was added a 1.6 N solution of butyllithium in hexane (5.78 ml, 9.26 mmol) at −78° C., and the mixture was stirred at −78° C. for 15 minutes. To the resultant solution was added dropwise 1-benzhydryl-4,6-dimethyl-1H-pyrrolo[2,3-b]pyridine-3-carbonitrile (2.00 g, 6.17 mmol), at −78° C. and the mixture was stirred at −78° C. for 30 minutes.
Dimethylformamide (1.43 ml, 18.5 mmol) was added thereto and the mixture was stirred at room temperature for 1.5 hours. The resultant mixture was poured into iced water and extracted with ethyl acetate. The extract was washed with water and dried over anhydrous magnesium sulfate. The solvent was distilled off under reduced pressure to give an objective product as a solid material.
Yield (amount) 1.97 g, yield (rate) 87.6% $^1$H-NMR (CDCl$_3$) δ: 2.53 (3H, s), 2.78 (3H, s), 6.96 (1H, s), 7.26-7.33 (10H, m), 8.18 (1H, s), 9.96 (1H, s).
IR(KBr) cm$^{-1}$; 2224, 1682, 1588, 1497, 1441, 733, 700.

(2) Ethyl (2E)-3-(1-benzhydryl-3-cyano-4,6-dimethyl-1H-pyrrolo[2,3-b]pyridin-2-yl)propenoate To 1-benzhydryl-2-formyl-4,6-dimethyl-1H-pyrrolo[2,3-b]pyridine-3-carbonitrile (1.80 g, 4.93 mmol) and triethyl phosphonoacetate(1.12 g, 5.02 mmol) in DMF (19 ml) was added sodium hydride (60%, 201 mg, 5.02 mmol) under ice-cooling, and then the mixture was stirred at room temperature for 40 minutes. The resultant mixture was poured into iced water and extracted with ethyl acetate. The extract was washed with water and dried over anhydrous magnesium sulfate. The solvent was distilled off under reduced pressure to give the objective product as a solid material.
Yield (amount) 1.62 g, yield (rate) 77.5% $^1$H-NMR (CDCl$_3$) δ: 1.24 (3H, t, J=7.4 Hz), 2.57 (3H, s), 2.76 (3H, s), 4.13 (2H, q, J=7.4 Hz), 6.77 (1H, d, J=16.2 Hz), 6.92 (1H, s), 7.17-7.42 (11H, m), 8.05 (1H, s).
IR(KBr) cm$^{-1}$; 2216, 1717, 1632, 1591, 1426, 1312, 1265, 1181, 735, 698, 667.

(3) (2E)-3-(1-benzhydryl-3-cyano-4,6-dimethyl-1H-pyrrolo[2,3-b]pyridin-2-yl)propenoic acid To a solution of ethyl (2E)-3-(1-benzhydryl-3-cyano-4,6-dimethyl-1H-pyrrolo[2,3-b]pyridin-2-yl)propenoate (1.52 g, 3.59 mmol) in ethanol (14 ml) and THF (10 ml) was added a 1 N aqueous sodium hydroxide solution (7.2 ml) and the mixture was stirred at room temperature for 7 hours. The reaction solution was poured into water, neutralized with 1 N hydrochloric acid and extracted with ethyl acetate. The extract was dried over anhydrous magnesium sulfate and the solvent was distilled off under reduced pressure to give the objective product as a solid material.
Yield (amount) 1.36 g, yield (rate) 95.8% $^1$H-NMR (CDCl$_3$) δ: 2.58 (3H, s), 2.76 (3H, s), 6.73 (1H, d, J=15.8 Hz), 6.94 (1H, s), 7.16-7.50 (11H, m), 8.06 (1H, s).
IR(KBr) cm$^{-1}$; 2975, 2216, 1694, 1630, 1591, 1495, 1435, 1323, 1273, 1215, 974, 910, 735, 700.

(4) (2E)-3-(1-benzhydryl-3-cyano-4,6-dimethyl-1H-pyrrolo[2,3-b]pyridin-2-yl)-N-(3,3-dimethylbutyl)prop-2-enamide To a solution of (2E)-3-(1-benzhydryl-3-cyano-4,6-dimethyl-1H-pyrrolo[2,3-b]pyridin-2-yl)propenoate (200 mg, 0.506 mmol) in THF (2 ml) were added DMF (0,01 ml) and oxalylchloride (0.053 ml, 0.607 mmol), the mixture was stirred at room temperature 1 hour, and the solvent was distilled off under reduced pressure. The residue was added under ice-cooling to a solution of 3,3-dimethylbutylamine (0.103 mg, 0.760 mmol), triethylamine (0.177 ml, 1.27 mmol) and THF (4 ml), and the mixture was stirred under ice-cooling for 1 hour. After stirring at room temperature for 4 hours, the reaction solution was poured into water and extracted with ethyl acetate. The extract was washed with water, dried over anhydrous magnesium sulfate and the solvent was distilled off under reduced pressure. The residue was purified by silica gel column chromatography (hexane:ethyl acetate=9:1) to give the objective product as a solid material. The resultant material was recrystallized from hexane and ethyl acetate.

Yield (amount) 78.0 mg, yield (rate) 31.5% $^1$H-NMR (CDCl$_3$) δ: 0.92 (9H, s), 1.37-1.45 (2H, m), 2.56 (3H, s), 2.75 (3H, s), 3.24-3.35 (2H, m), 5.48 (1H, bs), 6.75 (1H, d, J=15.6 Hz), 6.91 (1H, s), 7.21-7.44 (11H, m), 8.04 (1H, s).

IR(KBr) cm$^{-1}$; 3279, 2216, 1661, 1622, 1591, 1557, 1507, 1497, 1449, 1426, 1331, 735, 698.

Example 71

2E)-3-(1-benzhydryl-3-cyano-4,6-dimethyl-1H-pyrrolo[2,3-b]pyridin-2-yl)-N-tetrahydro-2H-pyran-4-ylprop-2-enamide To a solution of (2E)-3-(1-benzhydryl-3-cyano-4,6-dimethyl-1H-pyrrolo[2,3-b]pyridin-2-yl)propenoate (300 mg, 0.759 mmol) in THF (3 ml) were added DMF (0.03 ml) and oxalylchloride (0.0796 ml, 0.912 mmol), the mixture was stirred at room temperature for 1 hour, and the solvent was distilled off under reduced pressure.

The residue was added under ice-cooling to a solution of tetrahydro-2H-pyran-4-ylamine hydrochloride (184 mg, 1.51 mmol), triethylamine (0.560 ml, 4.01 mmol) and THF (3 ml), the mixture was stirred under ice-cooling for 1 hour and at room temperature for 12 hours. The reaction solution was poured into water, and extracted with ethyl acetate. The extract was washed with water, dried over anhydrous magnesium sulfate and the solvent was distilled off under reduced pressure. The residue was recrystallized from hexane and ethyl acetate.

Yield (amount) 173 mg, yield (rate) 46.5% $^1$H-NMR (CDCl$_3$) δ: 1.26-1.62 (2H, m), 1.84-1.90 (2H, m), 2.57 (3H, s), 2.75 (3H, s), 3.38-3.49 (2H, m), 3.92-4.10 (3H, m), 5.54 (1H, d, J=8.2 Hz), 6.78 (1H, d, J=15.8 Hz), 6.92 (1H, s), 7.20-7.45 (11H, m), 8.05 (1H, s)

IR(KBr) cm$^{-1}$; 3300, 2215, 1657, 1618, 1591, 1547, 1426, 1335, 912, 735, 698.

Reference Example 18

4,6-Dimethyl-1-[(1R)-1,2,3,4-tetrahydronaphthalen-1-yl]-1H-pyrrolo[2,3-b]pyridine-3-carbonitrile To a solution of formyl succinonitrile potassium salt (10.5 g, 72.0 mmol) and (1R)-1,2,3,4-tetrahydro-1-naphthylamine (11.6 g, 79.2 mmol) in water (30 ml) was added at room temperature acetic acid (30 ml). The mixture was stirred at 100° C. for 30 minutes and poured into iced water. The reaction mixture was made basic with potassium carbonate and then extracted with ethyl acetate. The extract was washed with water, dried over anhydrous magnesium sulfate and the solvent was distilled off under reduced pressure to give an oily matter. To a solution of the oily matter in tetrahydrofuran (75 ml) and ethanol (75 ml) was slowly added potassium ethoxide (10.5 g, 125 mmol), the mixture was stirred at room temperature for 1 hour and poured into iced water. The resultant mixture was extracted with ethyl acetate, the extract was washed with water, dried over anhydrous magnesium sulfate and the solvent was distilled off under reduced pressure to give an oily matter. To a solution of the oily matter in ethanol (75 ml) was sequentially added acetylacetone (5.86 g, 58.6 mmol) and concentrated hydrochloric acid (2.0 ml), the mixture was heated under reflux for 3 hours, poured into saturated sodium bicarbonate solution and extracted with ethyl acetate. The extract was washed with water, dried over anhydrous magnesium sulfate and the solvent was distilled off under reduced pressure. The residue was recrystallized from ethyl acetate.

Yield (amount) 6.71 g, yield (rate) 38.1% $^1$H-NMR (CDCl$_3$) δ: 1.79-1.94 (2H, m), 2.16-2.55 (2H, m), 2.63 (3H, s), 2.72 (3H, s), 2.88-2.98 (2H, m), 6.24 (1H, t, J=5.8 Hz), 6.81 (1H, d, J=7.2 Hz), 6.92 (1H, s), 7.10-7.30 (4H, m).

IR(KBr) cm$^{-1}$; 2218, 1588, 1524, 1447, 1391, 1188, 745.

Example 72

(2E)-3-{3-cyano-4,6-dimethyl-1-[(1R)-1,2,3,4-tetrahydronaphthalen-1-yl]-1H-pyrrolo[2,3-b]pyridin-2-yl}-N-[(4S)-2,2-dimethyltetrahydro-2H-pyran-4-yl]prop-2-enamide

Example 73

(2E)-3-{3-cyano-4,6-dimethyl-1-[(1R)-1,2,3,4-tetrahydronaphthalen-1-yl]-1H-pyrrolo[2,3-b]pyridin-2-yl}-N-[(4R)-2,2-dimethyltetrahydro-2H-pyran-4-yl]prop-2-enamide

(1) 2-formyl-4,6-dimethyl-1-[(1R)-1,2,3,4-tetrahydronaphthalen-1-yl]-1H-pyrrolo[2,3-b]pyridine-3-carbonitrile To a solution of diisopropylamine (3.72 ml, 28.4 mmol) in tetrahydrofuran (36 ml) was added a 1.6 N solution of butyllithium in hexane (17.7 ml, 28.4 mmol) at −78° C., and the mixture was stirred at −78° C. for 15 minutes. To the resultant solution was added dropwise 4,6-dimethyl-1-[(1R)-1,2,3,4-tetrahydronaphthalen-1-yl]-1H-pyrrolo[2,3-b]pyridine-3-carbonitrile (5.70 g, 18.9 mmol) in THF (60 ml) at −78° C., and the mixture was stirred at −78° C. for 30 minutes. Dimethylformamide (5.37 ml, 56.7 mmol) was added thereto, and the mixture was stirred at room temperature 1.5 hours, poured into iced water, and extracted with ethyl acetate. The extract was washed with water and dried over anhydrous magnesium sulfate. The solvent was distilled off under reduced pressure to give the objective product as oily matter.

Yield (amount) 6.00 g, yield (rate) 96.3% $^1$H-NMR (CDCl$_3$) δ: 1.98-3.18 (12H, m), 6.33 (1H, d, J=7.6 Hz), 6.79-7.23 (5H, m), 9.89 (1H, s).

IR(KBr) cm$^{-1}$; 2222, 1688, 1586, 1497, 1447, 731.

(2) Ethyl (2E)-3-{3-cyano-4,6-dimethyl-1-[(1R)-1,2,3,4-tetrahydronaphthalen-1-yl]-1H-pyrrolo[2,3-b]pyridin-2-yl}prop-2-enoate To 2-formyl-4,6-dimethyl-1-[(1R)-1,2,3,4-tetrahydronaphthalen-1-yl]-1H-pyrrolo[2,3-b]pyridine-3-carbonitrile (5.95 g, 18.1 mmol) and triethyl phosphonoacetate (4.12 g, 18.4 mmol) in DMF (60 ml) was added sodium hydride (60%, 736 mg, 18.4 mmol) under ice-cooling, the mixture was stirred at room temperature for 1 hour and poured into iced water, and the mixture was extracted with ethyl acetate. The extract was washed with water and dried over anhydrous magnesium sulfate. The solvent was distilled off under reduced pressure and the residue was purified by silica gel column chromatography (hexane:ethyl acetate=9:1) to give the objective product as powder.

Yield (amount) 4.55 g, yield (rate) 62.7% $^1$H-NMR (CDCl$_3$) δ: 1.26 (3H, t, J=7.0 Hz), 2.05-2.35 (4H, m), 2.60 (3H, s), 2.77 (3H, s), 2.91-3.09 (2H, m), 4.15 (2H, q, J=7.0 Hz), 6.54 (1H, d, J=7.8 Hz), 6.68-7.28 (7H, m).

IR(KBr) cm$^{-1}$; 2216, 1717, 1634, 1588, 1427, 1312, 1260, 1181, 1036, 978, 748, 735.

(3) (2E)-3-{3-cyano-4,6-dimethyl-1-[(1R)-1,2,3,4-tetrahydronaphthalen-1-yl]-1H-pyrrolo[2,3-b]pyridin-2-yl}prop-2-enoic acid To a solution of ethyl (2E)-3-{3-cyano-4,6-dimethyl-1-[(1R)-1,2,3,4-tetrahydronaphthalen-1-yl]-1H-pyrrolo[2,3-b]pyridin-2-yl}prop-2-enoate (4.25 g, 10.6 mmol) in ethanol (40 ml) and THF (30 ml) was added a 1 N aqueous sodium hydroxide solution (21 ml), and the mixture was stirred at room temperature for 1 hour. The reaction solution was poured into water, neutralized with 1 N hydrochloric acid and extracted with ethyl acetate. The extract was dried over anhydrous magnesium sulfate and the solvent was distilled off under reduced pressure to give the objective product as a solid material. The resultant material was recrystallized from ethyl acetate and hexane.

Yield (amount) 2.84 g, yield (rate) 72.0% $^1$H-NMR (CDCl$_3$) δ: 2.05-2.42 (4H, m), 2.60 (3H, s), 2.77 (3H, s), 2.99-3.09 (2H, m), 6.53 (1H, d, J=8.0 Hz), 6.74-7.37 (7H, m).

IR(KBr) cm$^{-1}$; 2942, 2216, 1694, 1628, 1590, 1435, 1319, 1264, 1217, 976, 910, 733.

Optical purity 99.8%ee

(4) (2E)-3-{3-cyano-4,6-dimethyl-1-[(1R)-1,2,3,4-tetrahydronaphthalen-1-yl]-1H-pyrrolo[2,3-b]pyridin-2-yl}-N-[(4S)-2,2-dimethyltetrahydro-2H-pyran-4-yl]prop-2-enamide

(2E)-3-{3-cyano-4,6-dimethyl-1-[(1R)-1,2,3,4-tetrahydronaphthalen-1-yl]-1H-pyrrolo[2,3-b]pyridin-2-yl}-N-[(4R)-2,2-dimethyltetrahydro-2H-pyran-4-yl]prop-2-enamide To a solution of (2E)-3-{3-cyano-4,6-dimethyl-1-[(1R)-1,2,3,4-tetrahydronaphthalen-1-yl]-1H-pyrrolo[2,3-b]pyridin-2-yl}prop-2-enoic acid (861 mg, 2.32 mmol) in THF (8 ml) were added DMF (0.1 ml) and oxalylchloride (0.243 ml, 2.79 mmol), the mixture was stirred at room temperature for 1 hour and the solvent was distilled off under reduced pressure. The residue was added under ice-cooling to a solution of 2,2-dimethyltetrahydro-2H-pyran-4-ylamine (600 mg, 4.64 mmol), triethylamine (1.08 ml, 7.71 mmol) and THF (6 ml), the mixture was stirred under ice-cooling for 2 hours, the reaction solution was poured into water and extracted with ethyl acetate. The extract was washed with water and dried over anhydrous magnesium sulfate, and the solvent was distilled off under reduced pressure. The residue was purified by silica gel column chromatography (hexane:ethyl acetate=2:1 to 1:1) to separate two kinds of diastereomers.

Firstly eluted diastereomer: (2E)-3-{3-cyano-4,6-dimethyl-1-[(1R)-1,2,3,4-tetrahydronaphthalen-1-yl]-1H-pyrrolo[2,3-b]pyridin-2-yl}-N-[(4S)-2,2-dimethyltetrahydro-2H-pyran-4-yl]prop-2-enamide yield 247 mg, yield (rate) 22.1% $^1$H-NMR (CDCl$_3$) δ: 1.24-1.40 (8H, m), 1.80-2.30 (6H, m), 2.59 (3H, s), 2.76 (3H, s), 2.90-3.23 (2H, m), 3.65-3.80 (2H, m), 4.19-4.24 (1H, m), 5.51 (1H, d, J=8.0 Hz), 6.49 (1H, d, J=7.5 Hz), 6.68-7.26 (7H, m).

IR(KBr) cm$^{-1}$; 3268, 2215, 1661, 1622, 1588, 1553, 1507, 1427, 1331, 1262, 1198, 735, 748.

Later eluted diastereomer: (2E)-3-{3-cyano-4,6-dimethyl-1-[(1R)-1,2,3,4-tetrahydronaphthalen-1-yl]-1H-pyrrolo[2,3-b]pyridin-2-yl}-N-[(4R)-2,2-dimethyltetrahydro-2H-pyran-4-yl]prop-2-enamide Yield (amount) 222 mg, yield (rate) 19.8% $^1$H-NMR (CDCl$_3$) δ: 1.20-1.36 (8H, m), 1.76-2.29 (6H, m), 2.59 (3H, s), 2.76 (3H, s), 2.90-3.16 (2H, m), 3.65-3.80 (2H, m), 4.19-4.23 (1H, m), 5.48 (1H, d, J=7.8 Hz), 6.50 (1H, d, J=8.1 Hz), 6.71-7.26 (7H, m).

IR(KBr) cm$^{-1}$; 3268, 2215, 1661, 1620, 1588, 1549, 1507, 1449, 1427, 1368, 1331, 1262, 1198, 750, 733.

Reference Example 19

4,6-Dimethyl-1-[(1S)-1,2,3,4-tetrahydronaphthalen-1-yl]-1H-pyrrolo[2,3-b]pyridine-3-carbonitrile To a solution of formyl succinonitrile potassium salt (10.5 g, 72.0 mmol) and (1S)-1,2,3,4-tetrahydro-1-naphthylamine (11.6 g, 79.2 mmol) in water (30 ml) was added acetic acid (30 ml) at room temperature. The mixture was stirred at 100° C. for 30 minutes and poured into iced water. The reaction mixture was made basic with potassium carbonate and then extracted with ethyl acetate. The extract was washed with water, dried over anhydrous magnesium sulfate, and the solvent was distilled off under reduced pressure to give an oily matter.

To a solution of the oily matter in tetrahydrofuran (75 ml) and ethanol (75 ml) was slowly added potassium ethoxide (10.5 g, 125 mmol), the mixture was stirred at room temperature for 1 hour and poured into iced water. The extract, which was obtained by extracting the resultant mixture with ethyl acetate, was washed with water, dried over anhydrous magnesium sulfate, and the solvent was distilled off under reduced pressure to give an oily matter. To a solution of the oily matter in ethanol (75 ml) was sequentially added acetylacetone (5.86 g, 58.6 mmol) and concentrated hydrochloric acid (2.0 ml). The mixture was heated under reflux for 3 hours, poured into saturated sodium bicarbonate solution and extracted with ethyl acetate. The extract was washed with water and dried over anhydrous magnesium sulfate, and the solvent was distilled off under reduced pressure. The residue was recrystallized from ethyl acetate.

Yield (amount) 3.78 g, yield (rate) 21.5% $^1$H-NMR (CDCl$_3$) δ: 1.79-1.94 (2H, m), 2.16-2.55 (2H, m), 2.63 (3H, s), 2.72 (3H, s), 2.88-2.98 (2H, m), 6.24 (1H, t, J=5.8 Hz), 6.81 (1H, d, J=7.2 Hz), 6.92 (1H, s), 7.10-7.30 (4H, m).

IR(KBr) cm$^{-1}$; 2218, 1588, 1524, 1447, 1391, 1188, 745.

Example 74

(2E)-3-{3-cyano-4,6-dimethyl-1-[(1S)-1,2,3,4-tetrahydronaphthalen-1-yl]-1H-pyrrolo[2,3-b]pyridin-2-yl}-N-[(4R)-2,2-dimethyltetrahydro-2H-pyran-4-yl]prop-2-enamide

Example 75

(2E)-3-{3-cyano-4,6-dimethyl-1-[(1S)-1,2,3,4-tetrahydronaphthalen-1-yl]-1H-pyrrolo[2,3-b]pyridin-2-yl}-N-[(4S)-2,2-dimethyltetrahydro-2H-pyran-4-yl]prop-2-enamide

(1) 2-formyl-4,6-dimethyl-1-[(1S)-1,2,3,4-tetrahydronaphthalen-1-yl]-1H-pyrrolo[2,3-b]pyridine-3-carbonitrile To a solution of diisopropylamine (2.36 ml, 18.0 mmol) in tetrahydrofuran (22 ml) was added a 1.6 N solution of butyllithium in hexane (11.3 ml, 18.0 mmol) at −78° C., and the mixture was stirred at −78° C. for 15 minutes. To the resultant solution was added dropwise a solution of 4,6-dimethyl-1-[(1S)-1,2,3,4-tetrahydronaphthalen-1-yl]-1H-pyrrolo[2,3-b]pyridine-3-carbonitrile (3.61 g, 12.0 mmol) in THF (60 ml) at −78° C., and the mixture was stirred at 78° C. for 30 minutes. Dimethylformamide (3.41 ml, 36.0 mmol) was added thereto, and the mixture was stirred at room temperature for 1.5 hours, poured into iced water and extracted with ethyl acetate. The extract was washed with water and dried over anhydrous magnesium sulfate. The solvent was distilled off under reduced pressure to give the objective product as oily matter.

Yield (amount) 2.00 g, yield (rate) 60.7% $^1$H-NMR (CDCl$_3$) δ: 1.98-3.18 (12H, m), 6.33 (1H, d, J=7.6 Hz), 6.79-7.23 (5H, m), 9.89 (1H, s)

IR(KBr) cm$^{-1}$; 2222, 1688, 1586, 1497, 1447, 731.

(2) Ethyl (2E)-3-{3-cyano-4,6-dimethyl-1-[(1S)-1,2,3,4-tetrahydronaphthalen-1-yl]-1H-pyrrolo[2,3-b]pyridin-2-yl}prop-2-enoate To 2-formyl-4,6-dimethyl-1-[(1S)-1,2,3,4-tetrahydronaphthalen-1-yl]-1H-pyrrolo[2,3-b]pyridine-3-carbonitrile (2.00 g, 6.07 mmol) and triethyl phosphonoacetate(1.38 g, 6.17 mmol) in DMF (20 ml) was added under ice-cooling sodium hydride (60%, 247 mg, 6.17 mmol), the mixture was stirred at room temperature for 1 hour, poured into iced water and extracted with ethyl acetate. The extract was washed with water, dried over anhydrous magnesium sulfate. The solvent was distilled off under reduced pressure and the residue was purified by silica gel column chromatography (hexane:ethyl acetate=9:1) to give the objective product as powder.

Yield (amount) 1.44 g, yield (rate) 59.5% $^1$H-NMR (CDCl$_3$) δ: 1.26 (3H, t, J=7.0 Hz), 2.05-2.35 (4H, m), 2.60 (3H, s), 2.77 (3H, s), 2.91-3.09 (2H, m), 4.15 (2H, q, J=7.0 Hz), 6.54 (1H, d, J=7.8 Hz), 6.68-7.28 (7H, m).

IR(KBr) cm$^{-1}$; 2216, 1717, 1634, 1588, 1427, 1312, 1260, 1181, 1036, 978, 748, 735.

(3) (2E)-3-{3-cyano-4,6-dimethyl-1-[(1S)-1,2,3,4-tetrahydronaphthalen-1-yl]-1H-pyrrolo[2,3-b]pyridin-2-yl}prop-2-enoic acid To a solution of ethyl (2E)-3-{3-cyano-4,6-dimethyl-1-[(1S)-1,2,3,4-tetrahydronaphthalen-1-yl]-1H-pyrrolo[2,3-b]pyridin-2-yl}prop-2-enoate (1.40 g, 3.50 mmol) in ethanol (10 ml) and THF (10 ml) was added a 1 N aqueous sodium hydroxide solution (7 ml), and the mixture was stirred at room temperature for 2 hours. The reaction solution was poured into water, neutralized with 1 N hydrochloric acid and extracted with ethyl acetate. The extract was dried over anhydrous magnesium sulfate, and the solvent was distilled off under reduced pressure to give the objective product as a solid material. The resultant material was recrystallized from ethyl acetate and hexane.

Yield (amount) 1.17 g, yield (rate) 90.0% $^1$H-NMR (CDCl$_3$) δ: 2.05-2.42 (4H, m), 2.60 (3H, s), 2.77 (3H, s), 2.99-3.09 (2H, m), 6.53 (1H, d, J=8.0 Hz), 6.74-7.37 (7H, m).

IR(KBr) cm$^{-1}$; 2942, 2216, 1694, 1628, 1590, 1435, 1319, 1264, 1217, 976, 910, 733.

Optical purity 99.8%ee

(4) (2E)-3-{3-cyano-4,6-dimethyl-1-[(1S)-1,2,3,4-tetrahydronaphthalen-1-yl]-1H-pyrrolo[2,3-b]pyridin-2-yl}-N-[(4R)-2,2-dimethyltetrahydro-2H-pyran-4-yl]prop-2-enamide (2E)-3-{3-cyano-4,6-dimethyl-1-[(1S)-1,2,3,4-tetrahydronaphthalen-1-yl]-1H-pyrrolo[2,3-b]pyridin-2-yl}-N-[(4S)-2,2-dimethyltetrahydro-2H-pyran-4-yl]prop-2-enamide To a solution of (2E)-3-{3-cyano-4,6-dimethyl-1-[(1S)-1,2,3,4-tetrahydronaphthalen-1-yl]-1H-pyrrolo[2,3-b]pyridin-2-yl}prop-2-enoic acid (861 mg, 2.32 mmol) in THF (8 ml) were added DMF (0.10 ml) and oxalylchloride (0.243 ml, 2.79 mmol), the mixture was stirred at room temperature for 1 hour and the solvent was distilled off under reduced pressure. The residue was added under ice-cooling to a solution of 2,2-dimethyltetrahydro-2H-pyran-4-ylamine (600 mg, 4.64 mmol), triethylamine (1.08 ml, 7.71 mmol) and THF (6 ml), the mixture was stirred under ice-cooling for 2 hours, the reaction solution was poured into water and extracted with ethyl acetate. The extract was washed with water and dried over anhydrous magnesium sulfate, and the solvent was distilled off under reduced pressure. The residue was purified by silica gel column chromatography (hexane:ethyl acetate=2:1 to 1:1) to separate two kinds of diastereomers.

Firstly eluted diastereomer: (2E)-3-{3-cyano-4,6-dimethyl-1-[(1S)-1,2,3,4-tetrahydronaphthalen-1-yl]-1H-pyrrolo[2,3-b]pyridin-2-yl}-N-[(4R)-2,2-dimethyltetrahydro-2H-pyran-4-yl]prop-2-enamide Yield (amount) 195 mg, yield (rate) 17.4% $^1$H-NMR (CDCl$_3$) δ: 1.24-1.40 (8H, m), 1.80-2.30 (6H, m), 2.59 (3H, s), 2.76 (3H, s), 2.90-3.23 (2H, m), 3.65-3.80 (2H, m), 4.19-4.24 (1H, m), 5.51 (1H, d, J=8.0 Hz), 6.49 (1H, d, J=7.5 Hz), 6.68-7.26 (7H, m).

IR(KBr) cm$^{-1}$; 3268, 2215, 1661, 1622, 1588, 1553, 1507, 1427, 1331, 1262, 1198, 735, 748.

Later eluted diastereomer: (2E)-3-{3-cyano-4,6-dimethyl-1-[(1S)-1,2,3,4-tetrahydronaphthalen-1-yl]-1H-pyrrolo[2,3-b]pyridin-2-yl}-N-[(4S)-2,2-dimethyltetrahydro-2H-pyran-4-yl]prop-2-enamide Yield (amount) 145 mg, yield (rate) 12.9% $^1$H-NMR (CDCl$_3$) δ: 1.20-1.36 (8H, m), 1.76-2.29 (6H, m), 2.59 (3H, s), 2.76 (3H, s), 2.90-3.16 (2H, m), 3.65-3.80 (2H, m), 4.19-4.23 (1H, m), 5.48 (1H, d, J=7.8 Hz), 6.50 (1H, d, J=8.1 Hz), 6.71-7.26 (7H, m).

IR(KBr) cm$^{-1}$; 3268, 2215, 1661, 1620, 1588, 1549, 1507, 1449, 1427, 1368, 1331, 1262, 1198, 750, 733.

Reference Example 20

1-[(4-Fluorophenyl)(phenyl)methyl]-4,6-dimethyl-1H-pyrrolo[2,3-b]pyridine-3-carbonitrile

(1) (4-Fluorophenyl)(phenyl)methylformamide

A mixed solution of 4-fluorobenzophenon (15.0 g, 75.0 mmol) and ammonium formate (38.5 g, 610 mmol) was stirred at 170° C. for 10 hours, the reaction solution was poured into water and extracted with ethyl acetate. The extract was washed with water, dried over anhydrous magnesium sulfate and the solvent was distilled off under reduced pressure to give the objective product as oily matter.

Yield (amount) 13.2 g, yield (rate) 76.7% $^1$H-NMR (CDCl$_3$) δ: 6.22-6.33 (2H, m), 6.96-7.40 (9H, m), 8.30 (1H, s).

IR(KBr) cm$^{-1}$; 3264, 1661, 1605, 1508, 1383, 1225, 1159, 829, 700.

(2) 1-(4-Fluorophenyl)-1-phenylmethaneamine

A mixed solution of (4-fluorophenyl)(phenyl)methylformamide (13.1 g, 57.1 mmol), concentrated hydrochloric acid (80 ml) and methanol (160 ml) was stirred at 90° C. for 3 hours, cooled to room temperature, and then a 6 N aqueous sodium hydroxide solution (200 ml) was added thereto, which was extracted with ethyl acetate. The extract was washed with water, dried over anhydrous magnesium sulfate, and the solvent was distilled off under reduced pressure to give the objective product as oily matter.

Yield (amount) 11.4 g, yield (rate) 99.1% $^1$H-NMR (CDCl$_3$) δ: 5.20 (1H, s), 6.94-7.37 (9H, m).

IR(KBr) cm$^{-1}$; 3061, 1603, 1507, 1453, 1223, 1157, 843, 783, 700.

(3) 2-({[(4-Fluorophenyl)(phenyl)methyl]amino}methylene)butanedinitrile

To a solution of formyl succinonitrile potassium salt (7.26 g, 49.7 mmol) and 1-(4-fluorophenyl)-1-phenylmethaneamine (11.0 g, 54.7 mmol) in water-(20 ml) was added acetic acid (20 ml) at room temperature, the mixture was stirred at 100° C. for 30 minutes, and the solvent was distilled off under reduced pressure. The residue was poured into iced water, made basic by adding potassium carbonate and then extracted with ethyl acetate. The extract was washed with water, dried over anhydrous magnesium sulfate. The solvent was distilled off under reduced pressure to give the objective product as a solid material.

Yield (amount) 14.0 g, yield (rate) 99.6% $^1$H-NMR (CDCl$_3$) δ: 3.12-3.17 (2H, m), 5.34-5.39 (1H, m), 5.55-5.58 (1H, m), 6.73-7.44 (10H, m).

IR(KBr) cm$^{-1}$; 3316, 2195, 1645, 1603, 1508, 1225, 1159, 833, 700.

(4) 5-Amino-1-[(4-fluorophenyl)(phenyl)methyl]-1H-pyrrole-3-carbonitrile

To a solution of 2-({[(4-fluorophenyl)(phenyl)methyl]amino}methylene)butanedinitrile (13.9 g, 47.7 mmol) in tetrahydrofuran (50 ml) and ethanol (50 ml) was slowly added potassium ethoxide (7.05 g, 83.8 mmol), the mixture was stirred at room temperature for 1 hour and poured into iced water. The product was extracted with ethyl acetate, the extract was washed with water, dried over anhydrous magnesium sulfate and the solvent was distilled off under reduced pressure to give the objective product as oily matter.

Yield (amount) 13.8 g, yield (rate) 99.3% $^1$H-NMR (CDCl$_3$) δ: 3.00 (2H, bs), 5.80 (1H, d, J=1.8 Hz), 6.45 (1H, d, J=1.8 Hz), 6.55 (1H, s), 6.94-7.42 (9H, m).

IR(KBr) cm$^{-1}$; 3385, 2220, 1605, 1508, 1227, 1159, 819, 700.

(5) 1-[(4-Fluorophenyl)(phenyl)methyl]-4,6-dimethyl-1H-pyrrolo[2,3-b]pyridine-3-carbonitrile To a solution of 5-amino-1-[(4-fluorophenyl)(phenyl)methyl]-1H-pyrrole-3-carbonitrile (13.7 g, 47.0 mmol) in ethanol (200 ml) was sequentially added acetylacetone (5.66 g, 56.6 mmol) and concentrated hydrochloric acid (2.0 ml). The mixture was heated under reflux for 3 hours, poured into saturated sodium bicarbonate solution and extracted with ethyl acetate. The extract was washed with water and dried over anhydrous magnesium sulfate, and the solvent was distilled off under reduced pressure. The residue was recrystallized from ethyl acetate and hexane.

Yield (amount) 10.0 g, yield (rate) 59.9% $^1$H-NMR (CDCl$_3$) δ: 2.55 (3H, s), 2.72 (3H, s), 6.89 (1H, s), 7.03-7.46 (11H, m).

IR(KBr) cm$^{-1}$; 2220, 1588, 1524, 1508, 1449, 1408, 1393, 1227, 1196, 1161, 739, 700.

Example 76

(2E)-3-{3-cyano-1-[(4-fluorophenyl)(phenyl)methyl]-4,6-dimethyl-1H-pyrrolo[2,3-b]pyridin-2-yl}-N-(2,2-dimethyltetrahydro-2H-pyran-4-yl)prop-2-enamide

(1) 1-[(4-Fluorophenyl)(phenyl)methyl]-2-formyl-4,6-dimethyl-1H-pyrrolo[2,3-b]pyridine-3-carbonitrile To a solution of diisopropylamine (4.46 ml, 34.0 mmol) in tetrahydrofuran (50 ml) was added a 1.6 N solution of butyllithium in hexane (21.3 ml, 34.0 mmol) at −78° C., and the mixture was stirred at −78° C. for 15 minutes. To the resultant solution was added dropwise 1-[(4-fluorophenyl)(phenyl)methyl]-4,6-dimethyl-1H-pyrrolo[2,3-b]pyridine-3-carbonitrile (9.35 g, 26.3 mmol) at −78° C., and the mixture was stirred at −78° C. for 30 minutes. Dimethylformamide (5.26 ml, 68.0 mmol) was added thereto, the resulting mixture was stirred at room temperature for 1.5 hours, poured into iced water and extracted with ethyl acetate. The extract was washed with water and dried over anhydrous magnesium sulfate. The solvent was distilled off under reduced pressure to give the objective product as a solid material.

Yield (amount) 9.64 g, yield (rate) 95.4% $^1$H-NMR (CDCl$_3$) δ: 2.51 (3H, s), 2.77 (3H, s), 6.95-7.34 (10H, m), 8.15 (1H, s), 10.03 (1H, s).

IR(KBr) cm$^{-1}$; 2224, 1682, 1590, 1447, 1424, 1229, 1161, 829, 733, 700.

(2) Ethyl (2E)-3-{3-cyano-1-[(4-fluorophenyl)(phenyl)methyl]-4,6-dimethyl-1H-pyrrolo[2,3-b]pyridin-2-yl}prop-2-enoate To 1-[(4-fluorophenyl)(phenyl)methyl]-2-formyl-4,6-dimethyl-1H-pyrrolo[2,3-b]pyridine-3-carbonitrile (9.50 g, 24.8 mmol) and triethyl phosphonoacetate(6.35 g, 28.3 mmol) in DMF (100 ml) was added under ice-cooling sodium hydride (60%, 1.13 g, 28.3 mmol). The mixture was stirred at room temperature for 1 hour, poured into iced water and extracted with ethyl acetate. The extract was washed with water and dried over anhydrous magnesium sulfate. The solvent was distilled off under reduced pressure and the residue was recrystallized from ethyl acetate and hexane.

Yield (amount) 7.500 g, yield (rate) 66.9% $^1$H-NMR (CDCl$_3$) δ: 1.25 (3H, t, J=7.2 Hz), 2.57 (3H, s), 2.76 (3H, s), 4.14 (2H, q, J=7.2 Hz), 6.78 (1H, d, J=16.2 Hz), 6.92-7.41 (11H, m), 8.00 (1H, s).

IR(KBr) cm$^{-1}$; 2216, 1715, 1634, 1591, 1510, 1311, 1264, 1233, 1182, 1030, 735, 700.

(3) (2E)-3-{3-cyano-1-[(4-fluorophenyl)(phenyl)methyl]-4,6-dimethyl-1H-pyrrolo[2,3-b]pyridin-2-yl}prop-2-enoic acid To a solution of ethyl (2E)-3-{3-cyano-1-[(4-fluorophenyl)(phenyl)methyl]-4,6-dimethyl-1H-pyrrolo[2,3-b]pyridin-2-yl}prop-2-enoic acid (7.40 g, 17.0 mmol) in ethanol (70 ml) and THF (80 ml) was added a 1 N aqueous sodium hydroxide solution (34ml), and the mixture was stirred at room temperature for 2 hours. The reaction solution was poured into water, neutralized with 1 N hydrochloric acid and extracted with ethyl acetate. The extract was dried over anhydrous magnesium sulfate and the solvent was distilled off under reduced pressure to give the objective product as a solid material. The product was recrystallized from ethyl acetate and hexane.

Yield (amount) 4.26 g, yield (rate) 58.9% $^1$H-NMR (CDCl$_3$) δ: 2.57 (3H, s), 2.76 (3H, s), 6.76 (1H, d, J=16.2 Hz), 6.94-7.50 (11H, m), 8.01 (1H, s).

IR(KBr) cm$^{-1}$; 3031, 2218, 1694, 1628, 1591, 1510, 1435, 1233, 1161, 735.

(4) (2E)-3-{3-cyano-1-[(4-fluorophenyl)(phenyl)methyl]-4,6-dimethyl-1H-pyrrolo[2,3-b]pyridin-2-yl}-N-(2,2-dimethyltetrahydro-2H-pyran-4-yl)prop-2-enamide To a solution of (2E)-3-{3-cyano-1-[(4-fluorophenyl)(phenyl)methyl]-4,6-dimethyl-1H-pyrrolo[2,3-b]pyridin-2-yl}prop-2-enoic acid (1.00 g, 2.35 mmol) in THF (10 ml) were added DMF (0.10 ml) and oxalylchloride (0.246 ml, 2.82 mmol), which was stirred at room temperature for 1 hour and the solvent was distilled off under reduced pressure. The residue was added under ice-cooling to a solution of 2,2-dimethyltetrahydro-2H-pyran-4-ylamine (455 mg, 3.53 mmol), triethylamine (1.09 ml, 7.81 mmol) and THF (10 ml), the mixture was stirred under ice-cooling for 2 hours and at room temperature for 12 hours. The reaction solution was poured into water and extracted with ethyl acetate. The extract was washed with water and dried over anhydrous magnesium sulfate, and the solvent was distilled off under reduced pressure. The residue was recrystallized from ethyl acetate and hexane to yield the objective product as a solid material.

Yield (amount) 1.04 g, yield (rate) 82.5% $^1$H-NMR (CDCl$_3$) δ: 1.17-1.42 (8H, m), 1.81-1.91 (2H, m), 2.56 (3H, s), 2.75 (3H, s), 3.62-3.74 (2H, m), 4.14-4.22 (1H, m), 5.48 (1H, d, J=7.6 Hz), 6.73-7.46 (12H, m), 7.99 (1H, s).

IR(KBr) cm$^{-1}$; 3285, 2215, 1661, 1622, 1591, 1547, 1510, 1333, 1231, 1195, 735.

Reference Example 21

1-[Bis(4-fluorophenyl)methyl]-4,6-dimethyl-1H-pyrrolo[2,3-b]pyridine-3-carbonitrile

(1) Bis(4-fluorophenyl)methylformamide

A mixture of 4,4'-difluorobenzophenone (15.0 g, 68.7 mmol) and ammonium formate (35.3 g, 559 mmol) was stirred at 170° C. for 10 hours. The reaction solution was poured into water and extracted with ethyl acetate. The extract was washed with water, dried over anhydrous magnesium sulfate, and the solvent was distilled off under reduced pressure to give the objective product as a solid material.

Yield (amount) 14.0 g, yield (rate) 82.4% $^1$H-NMR (CDCl$_3$) δ: 6.19-6.29 (2H, m), 6.98-7.20 (8H, m), 8.28 (1H, s).

IR(KBr) cm$^{-1}$; 3268, 1661, 1605, 1508, 1227, 1159, 1015, 833, 554.

(2) 1,1-Bis(4-fluorophenyl)methaneamine

A mixed solution of bis(4-fluorophenyl)methylformamide (13.9 g, 56.2 mmol), concentrated hydrochloric acid (80 ml) and methanol (160 ml) was stirred at 90° C. for 1.5 hours and cooled to room temperature, then a 6 N aqueous sodium hydroxide solution (170 ml) was added thereto, and the mixture was extracted with ethyl acetate. The extract was washed with water and dried over anhydrous magnesium sulfate, and the solvent was distilled off under reduced pressure to give the objective product as a solid material. Yield (amount) 11.5 g, yield (rate) 93.5%

$^1$H-NMR (CDCl$_3$) δ: 5.19 (1H, s), 6.95-7.02 (4H, m), 7.24-7.34 (4H, m).

IR(KBr) cm$^{-1}$; 3050, 1601, 1507, 1223, 1155, 833, 762.

(3) (2E)-2-({(bis(4-fluorophenyl)methyl]amino}methylene)butanedinitrile

To a solution of formyl succinonitrile potassium salt (6.67 g, 45.6 mmol) and 1,1-bis(4-fluorophenyl) methaneamine (11.0 g, 50.2 mmol) in water (19 ml) was added acetic acid (19 ml) at room temperature, and the mixture was stirred 100° C. for 30 minutes. The solvent was distilled off under reduced pressure. The residue was poured into iced water, made basic with potassium carbonate and then extracted with ethyl acetate. The extract was washed with water and dried over anhydrous magnesium sulfate, and the solvent was distilled off under reduced pressure to give the objective product as oily matter. Yield (amount) 14.0 g, yield (rate) 99.3%

$^1$H-NMR (CDCl$_3$) δ: 3.25 (2H, s), 5.41-5.48 (1H, m), 5.66 (0.5H, s), 5.68 (0.5H, s), 6.84 (0.5H, m), 6.91 (0.5H, s), 7.15-7.37 (8H, m).

IR(KBr) cm$^{-1}$; 3312, 2197, 1645, 1603, 1508, 1227, 1159, 837.

(4) 5-Amino-1-[bis(4-fluorophenyl)methyl]-1H-pyrrole-3-carbonitrile

To a solution of (2E)-2-({[bis(4-fluorophenyl)methyl]amino}methylene)butanedinitrile (13.9 g, 45.1 mmol) in tetrahydrofuran (48 ml) and ethanol (48 ml) was slowly added potassium ethoxide (6.67 g, 79.2 mmol), which was stirred at room temperature for 1 hour and poured into iced water. The product was extracted with ethyl acetate, the extract was washed with water, dried over anhydrous magnesium sulfate, and the solvent was distilled off under reduced pressure to give the objective product as oily matter.

Yield (amount) 12.9 g, yield (rate) 92.8% $^1$H-NMR (CDCl$_3$) δ: 2.98 (2H, bs), 5.81 (1H, d, J=1.8 Hz), 6.44 (1H, d, J=1.8 Hz), 6.55 (1H, s), 6.97-7.13 (8H, m).

IR(KBr) cm$^{-1}$; 3329, 2220, 1605, 1508, 1229, 1159, 828, 795, 785.

(5) 1-[Bis(4-fluorophenyl)methyl]-4,6-dimethyl-1H-pyrrolo[2,3-b]pyridine-3-carbonitrile To a solution of 5-amino-1-[bis(4-fluorophenyl)methyl]-1H-pyrrole-3-carbonitrile (13.9 g, 45.1 mmol) in ethanol (200 ml) was sequentially added acetylacetone (5.02 g, 50.2 mmol) and concentrated hydrochloric acid (2.0 ml). The mixture was heated under reflux for 3 hours, poured into saturated sodium bicarbonate solution and extracted with ethyl acetate. The extract was washed with water, dried over anhydrous magnesium sulfate, and the solvent was distilled off under reduced pressure to give the objective product as a solid material.

Yield (amount) 12.6 g, yield (rate) 80.8% $^1$H-NMR (CDCl$_3$) δ: 2.54 (3H, s), 2.72 (3H, s), 6.90 (1H, s), 7.04-7.08 (8H, m), 7.42 (2H, d, J=4.6 Hz).

IR(KBr) cm$^{-1}$; 2220, 1605, 1588, 1508, 1406, 1387, 1231, 1196, 1159, 841, 772, 733.

Example 77

(2E)-3-{1-[bis(4-fluorophenyl)methyl]-3-cyano-4,6-dimethyl-1H-pyrrolo[2,3-b]pyridin-2-yl}-N-(2,2-dimethyltetrahydro-2H-pyran-4-yl)prop-2-enamide (1) 1-[Bis(4-fluorophenyl)methyl]-2-formyl-4,6-dimethyl-1H-pyrrolo[2,3-b]pyridine-3-carbonitrile To a solution of diisopropylamine (5.27 ml, 40.2 mmol) in tetrahydrofuran (50 ml) was added a 1.6 N solution of butyllithium in hexane (25.1 ml, 40.2 mmol) at −78° C., which was stirred at −78° C. for 15 minutes. To the resultant solution was added dropwise 1-[bis(4-fluorophenyl)methyl]-4,6-dimethyl-1H-pyrrolo[2,3-b]pyridine-3-carbonitrile (11.6 g, 31.1 mmol) at −78° C., and the mixture was stirred at −78° C. for 30 minutes. Dimethylformamide (6.23 ml, 80.4 mmol) was added thereto, and the mixture was stirred at room temperature for 1.5 hours, poured into iced water and extracted with ethyl acetate. The extract was washed with water and dried over anhydrous magnesium sulfate. The solvent was distilled off under reduced pressure to give the objective product as a solid material.

Yield (amount) 11.7 g, yield (rate) 93.6% $^1$H-NMR (CDCl$_3$) δ: 2.49 (3H, s), 2.77 (3H, s), 6.94-7.31 (9H, m), 8.12 (1H, s), 10.01 (1H, s).

IR(KBr) cm$^{-1}$; 2224, 1682, 1605, 1508, 1445, 1422, 1229, 1161, 828, 731.

(2) Ethyl (2E)-3-{1-[bis(4-fluorophenyl)methyl]-3-cyano-4,6-dimethyl-1H-pyrrolo[2,3-b]pyridin-2-yl}prop-2-enoate To 1-[bis(4-fluorophenyl)methyl]-2-formyl-4,6-dimethyl-1H-pyrrolo[2,3-b]pyridine-3-carbonitrile (10.7 g, 26.7 mmol) and triethyl phosphonoacetate(6.85 g, 30.5 mmol) in DMF (100 ml) was added under ice-cooling sodium hydride (60%, 1.22 g, 30.5 mmol). The mixture was stirred at room temperature for 1 hour and poured into iced water and extracted with ethyl acetate. The extract was washed with water and dried over anhydrous magnesium sulfate. The solvent was distilled off under reduced pressure and the residue was purified by silica gel column chromatography (hexane:ethyl acetate=9:1) to give the objective product as a solid material. The resultant material was recrystallized from ethyl acetate and hexane.

Yield (amount) 3.20 g, yield (rate) 25.4% $^1$H-NMR (CDCl$_3$) δ: 1.26 (3H, t, J=7.4 Hz), 2.56 (3H, s), 2.76 (3H, s), 4.16 (2H, q, J=7.4 Hz), 6.75-7.40 (11H, m), 7.94 (1H, s).

IR(KBr) cm$^{-1}$; 2218, 1634, 1605, 1591, 1510, 1431, 1314, 1264, 1232, 1182, 1161, 1034, 866, 837, 801, 735.

(3) (2E)-3-{1-[bis(4-fluorophenyl)methyl]-3-cyano-4,6-dimethyl-1H-pyrrolo[2,3-b]pyridin-2-yl}prop-2-enoic acid To a solution of (2E)-3-{1-[bis(4-fluorophenyl)methyl]-3-cyano-4,6-dimethyl-1H-pyrrolo[2,3-b]pyridin-2-yl}prop-2-enoic acid ethyl (3.00 g, 6.36 mmol) in ethanol (28 ml) and THF (20 ml) was added a 1 N aqueous sodium hydroxide solution (13 ml) and the mixture was stirred at room temperature for 1 hour. The reaction solution was poured into water, neutralized with 1 N hydrochloric acid and extracted with ethyl acetate. The extract was dried over anhydrous magnesium sulfate and the solvent was distilled off under reduced pressure to give the objective product as a solid material. The resultant material was recrystallized from ethyl acetate and hexane. Yield (amount) 2.69 g, yield (rate) 95.4%

$^1$H-NMR (CDCl$_3$) δ: 2.57 (3H, s), 2.77 (3H, s), 6.79 (1H, d, J=16.0 Hz), 6.95-7.26 (8H, m), 7.45 (1H, d, J=16.0 Hz), 7.96 (1H, s).

IR(KBr) cm$^{-1}$; 2926, 2215, 1694, 1628, 1605, 1591, 1508, 1439, 1414, 1277, 1229, 1161, 974, 908, 866, 798, 737.

(4) (2E)-3-{1-[bis(4-fluorophenyl)methyl]-3-cyano-4,6-dimethyl-1H-pyrrolo[2,3-b]pyridin-2-yl}-N-(2,2-dimethyltetrahydro-2H-pyran-4-yl)prop-2-enamide To a solution of (2E)-3-{1-[bis(4-fluorophenyl)methyl]-3-cyano-4,6-dimethyl-1H-pyrrolo[2,3-b]pyridin-2-yl}prop-2-enoic acid (300 mg, 0.677 mmol) in THF (3 ml) were added DMF (0.03ml) and oxalylchloride (0.071 ml, 0.813 mmol), the mixture was stirred at room temperature for 1 hour and the solvent was distilled off under reduced pressure. The residue was added under ice-cooling to a solution of 2,2-dimethyltetrahydro-2H-pyran-4-ylamine (175 mg, 1.35 mmol), triethylamine (0.313 ml, 2.25 mmol) and THF (2 ml), and the mixture was stirred under ice-cooling for 2 hours. The reaction solution was poured into water and extracted with ethyl acetate. The extract was washed with water and dried over anhydrous magnesium sulfate, and the solvent was distilled off under reduced pressure. The residue was purified by silica gel column chromatography (hexane:ethyl acetate=2:1) to give the objective product as a solid material.

Yield (amount) 177 mg, yield (rate) 47.1% $^1$H-NMR (CDCl$_3$) δ: 1.18-1.40 (8H, m), 1.80-1.90 (2H, m), 2.56 (3H, s), 2.75 (3H, s), 3.69-3.77 (2H, m), 4.16-4.21 (1H, m), 5.49 (1H, d, J=7.6 Hz), 6.78 (1H, d, J=15.8 Hz), 6.92-7.26 (9H, m), 7.44 (1H, d, J=15.8 Hz), 7.94 (1H, s).

IR(KBr) cm$^{-1}$; 3289, 2216, 1661, 1607, 1510, 1333, 1231, 1159, 733.

Example 78

1-[Bis(4-fluorophenyl)methyl]-4,6-dimethyl-2-[(1E)-3-morpholin-4-yl-3-oxoprop-1-enyl]-1H-pyrrolo[2,3-b]pyridine-3-carbonitrile (2E)-3-{1-[bis(4-fluorophenyl)methyl]-3-cyano-4,6-dimethyl-1H-pyrrolo[2,3-b]pyridin-2-yl}-N-(2,2-dimethyltetrahydro-2H-pyran-4-yl)prop-2-enamide To a solution of (2E)-3-{1-[bis(4-fluorophenyl)methyl]-3-cyano-4,6-dimethyl-1H-pyrrolo[2,3-b]pyridin-2-yl}prop-2-enoic acid (250 mg, 0.570 mmol) in THF (2.5 ml) were added DMF (0.025 ml) and oxalylchloride (0.060 ml, 0.680 mmol), the mixture was stirred at room temperature for 1 hour and the solvent was distilled off under reduced pressure. The residue was added under ice-cooling to a solution of morpholine (0.0985 ml, 1.13 mmol), triethylamine (0.314 ml, 2.26 mmol) and THF (2.5 ml), and the mixture was stirred under ice-cooling for 2 hours and at room temperature for 12 hours. The reaction solution was poured into water and extracted with ethyl acetate. The extract was washed with water and dried over anhydrous magnesium sulfate, and the solvent distilled off under reduced pressure. The residue was recrystallized from hexane and ethyl acetate to give the objective product as a solid material.

Yield (amount) 207 mg, yield (rate) 71.1% $^1$H-NMR (CDCl$_3$) δ: 2.56 (3H, s), 2.75 (3H, s), 3.54-3.75 (8H, m), 6.93-7.48 (11H, m), 7.92 (1H, s).

IR(KBr) cm$^{-1}$; 2215, 1651, 1607, 1510, 1441, 1229, 1117, 839, 797, 729.

Example 79

(2E)-3-{1-[bis(4-fluorophenyl)methyl]-3-cyano-4,6-dimethyl-1H-pyrrolo[2,3-b]pyridin-2-yl}-N-(tetrahydro-2H-pyran-4-yl)prop-2-enamide To a solution of (2E)-3-{1-[bis(4-fluorophenyl)methyl]-3-cyano-4,6-dimethyl-1H-pyrrolo[2,3-b]pyridin-2-yl}prop-2-enoic acid (250 mg, 0.570 mmol) in THF (2.5 ml) were added DMF (0.025 ml) and oxalylchloride (0.060 ml, 0.680 mmol), the mixture was stirred at room temperature for 1 hour and the solvent distilled off under reduced pressure. The residue was added under ice-cooling to a solution of tetrahydro-2H-pyran-4-ylamine hydrochloride (136 mg, 1.13 mmol), triethylamine (0.472 ml, 3.39 mmol) and THF (3 ml), and the mixture was stirred under ice-cooling for 2 hours and at room temperature for 12 hours. The reaction solution was poured into water and extracted with ethyl acetate. The extract was washed with water and dried over anhydrous magnesium sulfate, and the solvent was distilled off under reduced pressure. The residue was purified by silica gel column chromatography (hexane:ethyl acetate=2:1) to give the objective product as a solid material. The resultant material was recrystallized from hexane and ethyl acetate. Yield (amount) 200 mg, yield (rate) 66.7%

$^1$H-NMR (CDCl$_3$) δ: 1.43-1.58 (2H, m), 1.87-1.92 (2H, m), 2.56 (3H, s), 2.75 (3H, s), 3.42-3.50 (2H, m), 3.94-4.05 (3H, m), 5.56 (1H, d, J=7.8 Hz), 6.78 (1H, d, J=15.3 Hz), 6.91-7.21 (9H, m), 7.43 (1H, d, J=15.3 Hz), 7.92 (1H, s).

IR(KBr) cm$^{-1}$; 3277, 2924, 2216, 1661, 1607, 1549, 1510, 1231, 1161, 1013, 837, 801, 733.

Example 80

1-[Bis(4-fluorophenyl)methyl]-2-{(1E)-3-[2,6-dimethylmorpholin-4-yl]-3-oxoprop-1-enyl}-4,6-dimethyl-1H-pyrrolo[2,3-b]pyridine-3-carbonitrile To a solution of (2E)-3-{1-[bis(4-fluorophenyl)methyl]-3-cyano-4,6-dimethyl-1H-pyrrolo[2,3-b]pyridin-2-yl}prop-2-enoic acid (200 mg, 0.451 mmol) in THF (2 ml) were added DMF (0.020 ml) and oxalylchloride (0.0471 ml, 0.540 mmol), the mixture was stirred at room temperature for 1 hour and the solvent was distilled off under reduced pressure. The residue was added under ice-cooling to a solution of cis-2,6-dimethylmorpholine (104 mg, 0.900 mmol), triethylamine (0.251 ml, 1.80 mmol) and THF (2 ml), and the mixture was stirred under ice-cooling for 2 hours and at room temperature for 12 hours. The reaction solution was poured into water and extracted with ethyl acetate. The extract was washed with water and dried over anhydrous magnesium sulfate, and the solvent was distilled off under reduced pressure. The residue was recrystallized from hexane and ethyl acetate.

Yield (amount) 180 mg, yield (rate) 74.1% $^1$H-NMR (CDCl$_3$) δ: 1.19-1.22 (6H, m), 2.35-2.43 (1H, m), 2.56 (3H, s), 2.75 (3H, s), 2.81-2.89 (1H, m), 3.48-3.58 (2H, m), 3.79 (1H, d, J=13.5 Hz), 4.43 (1H, d, J=13.5 Hz), 6.92 (1H, s), 6.99-7.40 (10H, m), 7.90 (1H, s).

IR(KBr) cm$^{-1}$; 2213, 1651, 1607, 1591, 1510, 1449, 1231, 1173, 1161, 1101, 1084, 835, 799, 731.

Example 81

(2E)-3-{1-[bis(4-fluorophenyl)methyl]-3-cyano-4,6-dimethyl-1H-pyrrolo[2,3-b]pyridin-2-yl}-N-(3,3-dimethylbutyl)prop-2-enamide To a solution of (2E)-3-{1-[bis(4-fluorophenyl)methyl]-3-cyano-4,6-dimethyl-1H-pyrrolo[2,3-b]pyridin-2-yl}prop-2-enoic acid (200 mg, 0.451 mmol) in THF (2 ml) were added DMF (0.020 ml) and oxalylchloride (0.0471 ml, 0.540 mmol), the mixture was stirred at room temperature for 1 hour and the solvent was distilled off under reduced pressure. The residue was added under ice-cooling to a solution of dimethylbutylamine (121 mg, 0.900 mmol), triethylamine (0.251 ml, 1.80 mmol) and THF (2 ml), and the mixture was stirred under ice-cooling for 2 hours and at room temperature for 12 hours. The reaction solution was poured into water and extracted with ethyl acetate. The extract was washed with water and dried over anhydrous magnesium sulfate, and the solvent was distilled off under reduced pressure. The residue was recrystallized from hexane and ethyl acetate. Yield (amount) 190 mg, yield (rate) 74.1%

$^1$H-NMR (CDCl$_3$) δ: 0.93 (9H, s), 1,40-1.46 (2H, m), 2.55 (3H, s), 2.74 (3H, s), 3.28-3.36 (2H, m), 5.57 (1H, t, J=7.4 Hz), 6.76 (1H, d, J=15.5 Hz), 6.91 (1H, s), 6.97-7.22 (8H, m), 7.42 (1H, d, J=15.5 Hz), 7.91 (1H, s).

IR(KBr) cm$^{-1}$; 3279, 2216, 1661, 1607, 1559, 1510, 1333, 1319, 1231, 1161, 837, 802, 735.

Example 82

(2E)-3-{1-[bis(4-fluorophenyl)methyl]-3-cyano-4,6-dimethyl-1H-pyrrolo[2,3-b]pyridin-2-yl}-N-(tert-butyl)prop-2-enamide To a solution of (2E)-3-{1-[bis(4-fluorophenyl)methyl]-3-cyano-4,6-dimethyl-1H-pyrrolo[2,3-b]pyridin-2-yl}prop-2-enoic acid (200 mg, 0.451 mmol) in THF (2 ml) were added DMF (0.020 ml) and oxalylchloride (0.0471 ml, 0.540 mmol), the mixture was stirred at room temperature for 1 hour and the solvent was distilled off under reduced pressure. The residue was added under ice-cooling to a solution of tert-butylamine (0.0945 ml, 0.900 mmol), triethylamine (0.251 ml, 1.80 mmol) and THF (2 ml), and the mixture was stirred under ice-cooling for 2 hours and at room temperature for 12 hours. The reaction solution was poured into water and extracted with ethyl acetate. The extract was washed with water and dried over anhydrous magnesium sulfate, and the solvent was distilled off under reduced pressure. The residue was recrystallized from hexane and ethyl acetate.

Yield (amount) 158 mg, yield (rate) 70.5%. $^1$H-NMR (CDCl$_3$) δ: 1.37 (9H, s), 2.54 (3H, s), 2.74 (3H, s), 5.43 (1H, s), 6.62 (1H, d, J=15.6 Hz), 6.90 (1H, s), 6.97-7.20 (8H, m), 7.36 (1H, d, J=15.6 Hz), 7.84 (1H, s).

IR(KBr) cm$^{-1}$; 3303, 2216, 1665, 1623, 1591, 1510, 1229, 1159, 735.

Example 83

Methyl N-((2E)-3-{3-cyano-4,6-dimethyl-1-[(1S)-1,2,3,4-tetrahydronaphthalen-1-yl]-1H-pyrrolo[2,3-b]pyridin-2-yl}prop-2-enoyl)-D-alaninate To a solution of (2E)-3-{3-cyano-4,6-dimethyl-1-[(1S)-1,2,3,4-tetrahydronaphthalen-1-yl]-1H-pyrrolo[2,3-b]pyridin-2-yl}prop-2-enoic acid (300 mg, 0.808 mmol) in THF (3 ml) were added DMF (0.03 ml) and oxalylchloride (0.0846 ml, 0.970 mmol), the mixture was stirred at room temperature for 1 hour and the solvent was distilled off under reduced pressure. The residue was added under ice-cooling to a solution of D-alanine methyl ester hydrochloride (226 mg, 1.62 mmol), triethylamine (0.676 ml, 4.86 mmol) and THF (3 ml), and the mixture was stirred under ice-cooling for 1 hour and at room temperature for 12 hours. The reaction solution was poured into water and extracted with ethyl acetate. The extract was washed with water and dried over anhydrous magnesium sulfate, and the solvent was distilled off under reduced pressure. The residue was recrystallized from hexane and ethyl acetate.

Yield (amount) 75.0 mg, yield (rate) 20.4% $^1$H-NMR (CDCl$_3$) δ; 1.41 (3H, d, J=6.8 Hz), 2. 01-2. 30 (4H, m), 2.59 (3H, s), 2.76 (3H, s), 2.87-3.14 (2H, m), 3.76 (3H, s), 4.63-4.70 (1H, m), 6.26 (1H, d, J=6.6Hz), 6.50 (1H, d, J=7.6 Hz), 6.97-7.28 (7H, m).

IR(KBr) cm$^{-1}$; 3300, 2215, 174.4, 1674, 1624, 1590, 1539, 1507, 1451, 1435, 1327, 1206, 1155, 978, 912, 733.

Example 84

(2E)-3-{3-cyano-4,6-dimethyl-1-[(1S)-1,2,3,4-tetrahydronaphthalen-1-yl]-1H-pyrrolo[2,3-b]pyridin-2-yl}-N-pyridin-4-ylprop-2-enamide To a solution of (2E)-3-{3-cyano-4,6-dimethyl-1-[(1S)-1,2,3,4-tetrahydronaphthalen-1-yl]-1H-pyrrolo[2,3-b]pyridin-2-yl]prop-2-enoic acid (300 mg, 0.808 mmol) in THF (3 ml) were added DMF (0.03 ml) and oxalylchloride (0.0846 ml, 0.970 mmol), the mixture was stirred at room temperature for 1 hour and the solvent was distilled off under reduced pressure. The residue was added under ice-cooling to a solution of 4-aminopyridine (152 mg, 1.62 mmol), triethylamine (0.451 ml, 3.24 mmol) and THF (3 ml), and the mixture was stirred under ice-cooling for 1 hour and at room temperature for 12 hours. The reaction solution was poured into water and extracted with ethyl acetate. The extract was washed with water and dried over anhydrous magnesium sulfate, and the solvent was distilled off under reduced pressure. The residue was purified by silica gel column chromatography (hexane:ethyl acetate=1:1) to give the objective product as a solid material. Yield (amount) 181 mg, yield (rate) 50.1%

$^1$H-NMR (CDCl$_3$) δ: 2.05-2.40 (4H, m), 2.60 (3H, s), 2.76 (3H, s), 2.92-3.24 (2H, m), 6.51 (1H, d, J=7.4Hz), 6.74-7.55 (9H, m) , 8.25 (1H, bs), 8.49 (2H, d, J=6.2 Hz)

IR(KBr) cm$^{-1}$; 3274, 2215, 1696, 1626, 1593, 1528, 1508, 1427, 1337, 1175, 748, 731.

Example 85

(2E)-3-{3-cyano-4,6-dimethyl-1-[(1S)-1,2,3,4-tetrahydronaphthalen-1-yl]-1H-pyrrolo[2,3-b]pyridin-2-yl}-N-pyridin-3-ylprop-2-enamide To a solution of (2E)-3-{3-cyano-4,6-dimethyl-1-[(1S)-1,2,3,4-tetrahydronaphthalen-1-yl]-1H-pyrrolo[2,3-b]pyridin-2-yl}prop-2-enoic acid (300 mg, 0.808 mmol) in THF (3 ml) were added DMF (0.03 ml) and oxalylchloride (0.0846 ml, 0.970 mmol), the mixture was stirred at room temperature for 1 hour and the solvent was distilled off under reduced pressure. The residue was added under ice-cooling to a solution of 3-aminopyridine (152 mg, 1.62 mmol), triethylamine (0.451 ml, 3.24 mmol) and THF (3 ml), and the mixture was stirred under ice-cooling for 1 hour and at room temperature for 12 hours. The reaction solution was poured into water and extracted with ethyl acetate. The extract was washed with water and dried over anhydrous magnesium sulfate, and the solvent was distilled off under reduced pressure. The residue was purified by silica gel column chromatography (hexane:ethyl acetate=1:1) to give the objective product as a solid material.

Yield (amount) 201 mg, yield (rate) 55.7% $^1$H-NMR (CDCl$_3$) δ: 1.99-2.41 (4H, m), 2.59 (3H, s), 2.76 (3H, s), 2.90-3.18 (2H, m), 6.51 (1H, d, J=7.8Hz), 6.69-7.42 (8H, m), 8.21-8.35 (3H, m), 8.64 (12H, d, J=2.2 Hz).

IR(KBr) cm$^{-1}$; 3304, 2215, 1684, 1624, 1590, 1551, 1483, 1427, 1337, 1319, 1283, 1194, 1177, 748, 733.

Example 86

(2E)-3-{3-cyano-4,6-dimethyl-1-[(1S)-1,2,3,4-tetrahydronaphthalen-1-yl]-1H-pyrrolo[2,3-b]pyridin-2-yl}-N-(2-methoxy-1-methylethyl)prop-2-enamide To a solution of (2E)-3-{3-cyano-4,6-dimethyl-1-[(1S)-1,2,3,4-tetrahydronaphthalen-1-yl]-1H-pyrrolo[2,3-b]pyridin-2-yl}prop-2-enoic acid (300 mg, 0.808 mmol) in THF (3 ml) were added DMF (0.03 ml) and oxalylchloride (0.0846 ml, 0.970 mmol), the mixture was stirred at room temperature for 1 hour and the solvent was distilled off under reduced pressure. The residue was added under ice-cooling to a solution of 2-amino-1-methoxypropane (0.171 ml, 1.62 mmol), triethylamine (0.451 ml, 3.24 mmol) and THF (3 ml), and the mixture was stirred under ice-cooling for 1 hour and at room temperature for 12 hours. The reaction solution was poured into water and extracted with ethyl acetate. The extract was washed with water and dried over anhydrous magnesium sulfate, and the solvent was distilled off under reduced pressure. The residue was purified by silica gel column chromatography (hexane:ethyl acetate=1:1) to give the objective product as a solid material.

Yield (amount) 71.0 mg, yield (rate) 19.9% $^1$H-NMR (CDCl$_3$) δ: 1.17 (3H, d, J=6.8 Hz), 2.01-2.27 (4H, m), 2.58 (3H, s), 2.76 (3H, s), 2.88-3.16 (2H, m), 3.35-3.44 (5H, m), 4.14-4.25 (1H, m), 5.92 (1H, d, J=8.4 Hz), 6.49 (1H, d, J=7.4 Hz), 6.65-7.28 (7H, m).

IR(KBr) cm$^{-1}$; 3283, 2215, 1663, 1622, 1590, 1541, 1508, 1451, 1327, 1264, 1217, 1107, 974, 912, 748, 733.

Example 87

(2E)-3-{3-cyano-4,6-dimethyl-1-[(1S)-1,2,3,4-tetrahydronaphthalen-1-yl]-1H-pyrrolo[2,3-b]pyridin-2-yl}-N-cyclohexylprop-2-enamide To a solution of (2E)-3-{3-cyano-4,6-dimethyl-1-[(1S)-1,2,3,4-tetrahydronaphthalen-1-yl]-1H-pyrrolo[2,3-b]pyridin-2-yl}prop-2-enoic acid (300 mg, 0.808 mmol) in THF (3 ml) were added DMF (0.03 ml) and oxalylchloride (0.0846 ml, 0.970 mmol), the mixture was stirred at room temperature for 1 hour and the solvent was distilled off under reduced pressure. The residue was added under ice-cooling to a solution of cyclohexylamine (0.185 ml, 1.62 mmol), triethylamine (0.451 ml, 3.24 mmol) and THF (3 ml), and the mixture was stirred under ice-cooling for 1 hour and at room temperature for 12 hours. The reaction solution was poured into water and extracted with ethyl acetate. The extract was washed with water and dried over anhydrous magnesium sulfate, and the solvent was distilled off under reduced pressure. The residue was purified by silica gel column chromatography (hexane: ethyl acetate=3:1) to give the objective product as a solid material.

Yield (amount) 190 mg, yield (rate) 51.8% $^1$H-NMR (CDCl$_3$) δ: 1.03-2.32 (14H, m), 2.59 (3H, s), 2.76 (3H, s), 2.87-3.24 (2H, m), 3.71-3.91 1H, m), 5.56 (1H, d, J=8.8 Hz), 6.49 (1H, d, J=7.6 Hz), 6.65-7.28 (7H, m).

IR(KBr) cm$^{-1}$; 3270, 2.932, 2215, 1661, 1622, 1590, 1543, 1508, 1451, 1427, 1327, 1217, 1204, 910, 733.

Example 88

(2E)-3-{3-cyano-4,6-dimethyl-1-[(1S)-1,2,3,4-tetrahydronaphthalen-1-yl]-1H-pyrrolo[2,3-b]pyridin-2-yl}-N-phenylprop-2-enamide To a solution of (2E)-3-{3-cyano-4,6-dimethyl-1-[(1S)-1,2,3,4-tetrahydronaphthalen-1-yl]-1H-pyrrolo[2,3-b]pyridin-2-yl}prop-2-enoic acid (300 mg, 0.808 mmol) in THF (3 ml) were added DMF (0.03 ml)and oxalylchloride (0.0846 ml, 0.970 mmol), the mixture was stirred at room temperature for 1 hour and the solvent was distilled off under reduced pressure. The residue was added under ice-cooling to a solution of aniline (0.157 ml, 1.62 mmol), pyridine (0.262 ml, 3.24 mmol) and THF (3 ml), and the mixture was stirred under ice-cooling for 1 hour and at room temperature for 12 hours. The reaction solution was poured into water and extracted with ethyl acetate. The extract was washed with water and dried over anhydrous magnesium sulfate, and the solvent was distilled off under reduced pressure. The residue was purified by silica gel column chromatography (hexane:ethyl acetate=3:1) to give the objective product as a solid material.

Yield (amount) 240 mg, yield (rate) 66.3% $^1$H-NMR (CDCl$_3$) δ: 2.05-2.33 (4H, m), 2.60 (3H, s), 2.77 (3H, s), 2.89-3.24 (2H, m), 3.65 (1H, bs), 6.50 (1H, d, J=7.6 Hz), 6.675-7.63 (12H, m).

IR(KBr) cm$^{-1}$; 3306, 2944, 2213, 1669, 1624, 1601, 1549, 1499, 1443, 1337, 1258, 1177, 908, 748, 733, 693.

Example 89

(2E)-N-(2-chloropyridin-4-yl)-3-{3-cyano-4,6-dimethyl-1-[(1S)-1,2,3,4-tetrahydronaphthalen-1-yl]-1H-pyrrolo[2,3-b]pyridin-2-yl}prop-2-enamide To a solution of (2E)-3-{3-cyano-4,6-dimethyl-1-[(1S)-1,2,3,4-tetrahydronaphthalen-1-yl]-1H-pyrrolo[2,3-b]pyridin-2-yl}prop-2-enoic acid (300 mg, 0.808 mmol) in THF (3 ml) were added DMF (0.03 ml) and oxalylchloride (0.0846 ml, 0.970 mmol), the mixture was stirred at room temperature for 1 hour and the solvent was distilled off under reduced pressure. The residue was added under ice-cooling to a solution of 4-amino-2-chloropyridine (209 mg, 1.62 mmol), triethylamine (0.451 ml, 3.24 mmol) and THF (3 ml), and the mixture was stirred under ice-cooling for 1 hour and at room temperature for 12 hours. The reaction solution was poured into water and extracted with ethyl acetate. The extract was washed with water and dried over anhydrous magnesium sulfate, and the solvent was distilled off under reduced pressure. The residue was purified by silica gel column chromatography (hexane ethyl acetate=2:1) to give the objective product as a solid material.

Yield (amount) 36.0 mg, yield (rate) 9.3% $^1$H-NMR (CDCl$_3$) δ: 2.05-2.36 (4H, m), 2.61 (3H, s), 2.75 (3H, s), 2.92-3.20 (2H, m), 6.52 (1H, d, J=7.8Hz), 6.77-7.36 (8H, m), 7.74 (1H, d, J=1.8 Hz), 8.13 (1H, s), 8.25 (1H, d, J=5.4 Hz).

IR(KBr) cm$^{-1}$; 3300, 2215, 1698, 1626, 1586, 1506, 1429, 1381, 1323, 1265, 1173, 1127, 731.

Example 90

(2E)-3-{3-cyano-4,6-dimethyl-1-[(1S)-1,2,3,4-tetrahydronaphthalen-1-yl]-1H-pyrrolo[2,3-b]pyridin-2-yl}-N-(pyridin-4-ylmethyl)prop-2-enamide To a solution of (2E)-3-{3-cyano-4,6-dimethyl-1-[(1S)-1,2,3,4-tetrahydronaphthalen-1-yl]-1H-pyrrolo[2,3-b]pyridin-2-yl}prop-2-enoic acid (300 mg, 0.808 mmol) in THF (3 ml) were added DMF (0.03 ml) and oxalylchloride (0.0846 ml, 0.970 mmol), the mixture was stirred at room temperature for 1 hour and the solvent was distilled off under reduced pressure. The residue was added under ice-cooling to a solution of 4-aminomethylpyridine (175 mg, 1.62 mmol), triethylamine (0.451 ml, 3.24 mmol) and THF (3 ml), and the mixture was stirred under ice-cooling for 1 hour and at room temperature for 12 hours. The reaction solution was poured into water and extracted with ethyl acetate. The extract was washed with water and dried over anhydrous magnesium sulfate, and the solvent was distilled off under reduced pressure. The residue was purified by silica gel column chromatography (ethyl acetate) to give the objective product as a solid material.

Yield (amount) 287 mg, yield (rate) 77.2% $^1$H-NMR (CDCl$_3$) δ: 1.96-2.31 (4H, m), 2.59 (3H, s), 2.74 (3H, s), 2.87-3.16 (2H, m), 4.51 (2H, d, J=5.8 Hz), 6.28 (1H, t, J=5.8 Hz), 6.50 (1H, d, J=7.8Hz), 6.67-7.28 (9H, m), 8.54 (2H, d, J=4.2 Hz)

IR(KBr) cm$^{-1}$; 3270, 2215, 1663, 1622, 1590, 1564, 1553, 1507, 1427, 1327, 1264, 1221, 910, 731.

Example 91

(2E)-3-{3-cyano-4,6-dimethyl-1-[(1S)-1,2,3,4-tetrahydronaphthalen-1-yl]-1H-pyrrolo[2,3-b]pyridin-2-yl}-N-(1-ethylpropyl)prop-2-enamide TO a solution of (2E)-3-{3-cyano-4,6-dimethyl-1-[(1S)-1,2,3,4-tetrahydronaphthalen-1-yl]-1H-pyrrolo[2,3-b]pyridin-2-yl}prop-2-enoic acid (300 mg, 0.808 mmol) in THF (3 ml) were added DMF (0.03 ml) and oxalylchloride (0.0846 ml, 0.970 mmol), the mixture was stirred at room temperature for 1 hour and the solvent was distilled off under reduced pressure. The residue was added under ice-cooling to a solution of 3-aminopentane (141 mg, 1.62 mmol), triethylamine (0.451 ml, 3.24 mmol) and THF (3 ml), and the mixture was stirred under ice-cooling for 1 hour and at room temperature for 12 hours. The reaction solution was poured into water and extracted with ethyl acetate. The extract was washed with water and dried over anhydrous magnesium sulfate, and the solvent was distilled off under reduced pressure. The residue was purified by silica gel column chromatography (hexane: ethyl acetate=3:1) to give the objective product as oily matter.

Yield (amount) 224 mg, yield (rate) 62.9% $^1$H-NMR (CDCl$_3$) δ: 0.85 (6H, t, J=7.6 Hz), 1.27-1.58 (4H, m), 2.05-2.33 (4H, m), 2.58 (3H, s), 2.76 (3H, s), 2.87-3.18 (2H, m), 3.78-3.89 (1H, m), 5.35 (1H, d, J=8.4 Hz), 6.48 (1H, d, J=7.6Hz), 6.65-7.28 (7H, m).

IR(KBr) cm$^{-1}$; 3287, 2215, 1661, 1622, 1590, 1545, 1507, 1427, 1327, 1262, 1219, 976, 909, 733.

Example 92

(2E)-3-{3-cyano-4,6-dimethyl-1-[(1S)-1,2,3,4-tetrahydronaphthalen-1-yl]-1H-pyrrolo[2,3-b]pyridin-2-yl}-N-(3,4-dimethoxyphenyl)prop-2-enamide To a solution of (2E)-3-{3-cyano-4,6-dimethyl-1-[(1S)-1,2,3,4-tetrahydronaphthalen-1-yl]-1H-pyrrolo[2,3-b]pyridin-2-yl}prop-2-enoic acid (300 mg, 0.808 mmol) in THF (3 ml)

were added DMF (0.03 ml) and oxalylchloride (0.0846 ml, 0.970 mmol), the mixture was stirred at room temperature for 1 hour and the solvent was distilled off under reduced pressure. The residue was added under ice-cooling to a solution of 3,4-dimethoxy aniline (248 mg, 1.62 mmol), pyridine (0.262 ml, 3.24 mmol) and THF (3 ml), and the mixture was stirred under ice-cooling for 1 hour and at room temperature for 12 hours. The reaction solution was poured into water and extracted with ethyl acetate. The extract was washed with water and dried over anhydrous magnesium sulfate, and the solvent was distilled off under reduced pressure. The residue was purified by silica gel column chromatography (hexane: ethyl acetate=2:1) to give the objective product as a solid material.

Yield (amount) 234 mg, yield (rate) 57.4% $^1$H-NMR (CDCl$_3$) δ: 2.05-2.35 (4H, m), 2.59 (3H, s), 2.77 (3H, s), 2.88-3.26 (2H, m), 3.86 (3H, s), 3.89 (3H, s), 6.49 (1H, d, J=7.6Hz), 6.67-7.44 (11H, m).

IR(KBr) cm$^{-1}$; 3293, 2215, 1663, 1613, 1591, 1551, 1514, 1427, 1319, 1260, 1235, 1217, 1028, 912, 733.

Example 93

3-{3-Cyano-4,6-dimethyl-1-[(1S)-1,2,3,4-tetrahydronaphthalen-1-yl]-1H-pyrrolo[2,3-b]pyridin-2-yl}-N-(3,4-dimethoxyphenyl)propanamide A mixed solution of (2E)-3-{3-cyano-4,6-dimethyl-1-[(1S)-1,2,3,4-tetrahydronaphthalen-1-yl]-1H-pyrrolo[2,3-b]pyridin-2-yl}-N-(3,4-dimethoxyphenyl)prop-2-enamide (170 mg, 0.336 mmol), 10% palladium carbon (20 mg), THF (3 ml) and methanol (3 ml) was stirred under hydrogen atmosphere for 4 hours. Insolubles were filtrated off and the filtrate was concentrated to give the objective product as a solid material.

Yield (amount) 150 mg, yield (rate) 87.7% $^1$H-NMR (CDCl$_3$) δ: 2.05-2.34 (6H, m), 2.55 (3H, s), 2.71 (3H, s), 2.87-3.23 (4H, m), 3.85 (3H, s), 3.87 (3H, s), 6.48 (1H, d, J=8.2 Hz), 6.60-7.22 (9H, m)

IR(KBr) cm$^{-1}$; 3333, 2213, 1669, 1609, 1593, 1514, 1451, 1404, 1260, 1235, 1028, 912, 733.

Example 94

(2E)-3-{3-cyano-4,6-dimethyl-1-[(1S)-1,2,3,4-tetrahydronaphthalen-1-yl]-1H-pyrrolo[2,3-b]pyridin-2-yl}-N-(4-methoxyphenyl)prop-2-enamide To a solution of (2E)-3-{3-cyano-4,6-dimethyl-1-[(1S)-1,2,3,4-tetrahydronaphthalen-1-yl]-1H-pyrrolo[2,3-b]pyridin-2-yl}prop-2-enoic acid (300 mg, 0.808 mmol) in THF (3 ml) were added DMF (0.03 ml) and oxalylchloride (0.0846 ml, 0.970 mmol), the mixture was stirred at room temperature for 1 hour and the solvent was distilled off under reduced pressure. The residue was added under ice-cooling to a solution of p-anisidine (199 mg, 1.62 mmol), pyridine (0.262 ml, 3.24 mmol) and THF (3 ml), and the mixture was stirred under ice-cooling for 2 hours and at room temperature for 12 hours. The reaction solution was poured into water and extracted with ethyl acetate. The extract was washed with water and dried over anhydrous magnesium sulfate, and the solvent was distilled off under reduced pressure. The residue was purified by silica gel column chromatography (hexane:ethyl acetate=5:1) to give the objective product as a solid material. The resultant material was recrystallized from hexane and ethyl acetate.

Yield (amount) 318 mg, yield (rate) 82.6% $^1$H-NMR (CDCl$_3$) δ: 1.98-2.31 (4H, m), 2.59 (3H, s), 2.76 (3H, s), 2.90-3.23 (2H, m), 3.78 (3H, s), 6.49 (1H, d, J=7.8 Hz), 6.66-7.60 (12H, m).

IR(KBr) cm$^{-1}$; 3308, 2213, 1665, 1624, 1605, 1590, 1549, 1510, 1427, 1319, 1246, 1173, 1036, 829, 748, 731.

Example 95

(2E)-3-{3-cyano-4,6-dimethyl-1-[(1S)-1,2,3,4-tetrahydronaphthalen-1-yl]-1H-pyrrolo[2,3-b]pyridin-2-yl}-N-(4-fluorophenyl)prop-2-enamide To a solution of (2E)-3-{3-cyano-4,6-dimethyl-1-[(1S)-1,2,3,4-tetrahydronaphthalen-1-yl]-1H-pyrrolo[2,3-b]pyridin-2-yl}prop-2-enoic acid (300 mg, 0.808 mmol) in THF (3 ml) were added DMF (0.03 ml) and oxalylchloride (0.0846 ml, 0.970 mmol), the mixture was stirred at room temperature for 1 hour and the solvent was distilled off under reduced pressure. The residue was added under ice-cooling to a solution of 4-fluoroaniline (0.153 ml, 1.62 mmol), pyridine (0.262 ml, 3.24 mmol) and THF (3 ml), and the mixture was stirred under ice-cooling for 2 hours and at room temperature for 12 hours. The reaction solution was poured into water and extracted with ethyl acetate. The extract was washed with water and dried over anhydrous magnesium sulfate, and the solvent was distilled off under reduced pressure. The residue was purified by silica gel column chromatography (hexane: ethyl acetate=5:1) to give the objective product as a solid material. The resultant material was recrystallized from hexane and ethyl acetate.

Yield (amount) 238 mg, yield (rate) 63.5% $^1$H-NMR (CDCl$_3$) δ: 1.98-2.32 (4H, m), 2.59 (3H, s), 2.76 (3H, s), 2.90-3.18 (2H, m), 6.50 (1H, d, J=7.8 Hz), 6.69-7.64 (12H, m).

IR(KBr) cm$^{-1}$; 3308, 2215, 1667, 1626, 1588, 1508, 1427, 1406, 1339, 1319, 1215, 1179, 835, 748, 733.

Example 96

(2E)-3-{3-cyano-4,6-dimethyl-1-[(1S)-1,2,3,4-tetrahydronaphthalen-1-yl]-1H-pyrrolo[2,3-b]pyridin-2-yl}-N-(3-methoxyphenyl)prop-2-enamide To a solution of (2E)-3-{3-cyano-4,6-dimethyl-1-[(1S)-1,2,3,4-tetrahydronaphthalen-1-yl]-1H-pyrrolo[2,3-b]pyridin-2-yl}prop-2-enoic acid (300 mg, 0.808 mmol) in THF (3 ml) were added DMF (0.03 ml) and oxalylchloride (0.0846 ml, 0.970 mmol), the mixture was stirred at room temperature for 1 hour and the solvent was distilled off under reduced pressure. The residue was added under ice-cooling to a solution of m-anisidine (0.182 ml, 1.62 mmol), pyridine (0.262 ml, 3.24 mmol) and THF (3 ml), and the mixture was stirred under ice-cooling for 2 hours and at room temperature for 12 hours. The reaction solution was poured into water and extracted with ethyl acetate. The extract was washed with water and dried over anhydrous magnesium sulfate, and the solvent was distilled off under reduced pressure. The residue was purified by silica gel column chromatography (hexane:ethyl acetate=5:1) to give the objective product as a solid material.

Yield (amount) 214 mg, yield (rate) 55.6% $^1$H-NMR (CDCl$_3$) δ: 1.99-2.29 (4H, m), 2.58 (3H, s), 2.73 (3H, s), 2.86-3.26 (2H, m), 3.76 (3H, s), 6.49 (1H, d, J=7.8 Hz), 6.62-7.41 (11H, m), 8.05 (1H, s).

IR(KBr) cm$^{-1}$; 3312, 2215, 1669, 1613, 1553, 1493, 1454, 1431, 1321, 1287, 1260, 1215, 1182, 1155, 1125, 1042, 974, 910, 858, 777, 733, 687, 673.

Example 97

(2E)-N-benzyl-3-{3-cyano-4,6-dimethyl-1-[(1S)-1,2,3,4-tetrahydronaphthalen-1-yl]-1H-pyrrolo[2,3-b]pyridin-2-yl}prop-2-enamide To a solution of (2E)-3-{3-cyano-4,6-dimethyl-1-[(1S)-1,2,3,4-tetrahydronaphthalen-1-yl]-1H-pyrrolo[2,3-b]pyridin-2-yl}prop-2-enoic acid (300 mg, 0.808 mmol) in THF (3 ml) were added DMF (0.03 ml) and oxalylchloride (0.0846 ml, 0.97-0 mmol), the mixture was stirred at room temperature for 1 hour and the solvent was distilled off under reduced pressure. The residue was added under ice-cooling to a solution of benzylamine (0.176 ml, 1.62 mmol), triethylamine (0.451 ml, 3.24 mmol) and THF (3 ml), and the mixture was stirred under ice-cooling for 1 hour and at room temperature for 12 hours. The reaction solution was poured into water and extracted with ethyl acetate. The extract was washed with water and dried over anhydrous magnesium sulfate, and the solvent was distilled off under reduced pressure. The residue was purified by silica gel column chromatography (hexane:ethyl acetate=5:1) to give the objective product as powder.

Yield (amount) 95.0 mg, yield (rate) 25.5% $^1$H-NMR (CDCl$_3$) δ: 2.05-2.32 (4H, m), 2.58 (3H, s), 2.74 (3H, s), 2.90-3.18 (2H, m), 4.79 (1H, d, J=5.6 Hz), 5.87 (1H, bs), 6.50 (1H, d, J=7.8 Hz), 6.70-7.34 (12H, m).

IR(KBr) cm$^{-1}$; 3270, 2215, 1661, 1622, 1588, 1549, 1495, 1454, 1427, 1325, 1263, 1221, 912, 737.

Example 98

(2E)-3-{3-cyano-4,6-dimethyl-1-[(1S)-1,2,3,4-tetrahydronaphthalen-1-yl]-1H-pyrrolo[2,3-b.]pyridin-2-yl}-N-(3,4-dimethylphenyl)prop-2-enamide To a solution of (2E)-3-{3-cyano-4,6-dimethyl-1-[(1S)-1,2,3,4-tetrahydronaphthalen-1-yl]-1H-pyrrolo[2,3-b]pyridin-2-yl}prop-2-enoic acid (300 mg, 0.808 mmol) in THF (3 ml) were added DMF (0.03 ml) and oxalylchloride (0.0846 ml, 0.970 mmol), the mixture was stirred at room temperature for 1 hour and the solvent was distilled off under reduced pressure. The residue was added under ice-cooling to a solution of dimethylaniline (117 mg, 0.698 mmol), pyridine (0.262 ml, 3.24 mmol) and THF (3 ml), and the mixture was stirred under ice-cooling for 1 hour and at room temperature for 12 hours. The reaction solution was poured into water and extracted with ethyl acetate. The extract was washed with water and dried over anhydrous magnesium sulfate, and the solvent was distilled off under reduced pressure. The residue was purified by silica gel column chromatography (hexane:ethyl acetate=5:1) to give the objective product as a solid material.

Yield (amount) 123 mg, yield (rate) 34.7% $^1$H-NMR (CDCl$_3$) δ: 2.04-2.34 (10H, m), 2.58 (3H, s), 2.77 (3H, s), 2.88-3.25 (2H, m), 6.49 (1H, d, J=8.0 Hz), 6.66-7.40 (11H, m).

IR(KBr) cm$^{-1}$; 3318, 2215, 1665, 1618, 1593, 1541, 1505, 1449, 1427, 1400, 1325, 1258, 1215, 1196, 912, 731.

Example 99

(2E)-3-{3-cyano-4,6-dimethyl-1-[(1S)-1,2,3,4-tetrahydronaphthalen-1-yl]-1H-pyrrolo[2,3-b]pyridin-2-yl}-N-(4-methylphenyl)prop-2-enamide To a solution of (2E)-3-{3-cyano-4,6-dimethyl-1-[(1S)-1,2,3,4-tetrahydronaphthalen-1-yl]-1H-pyrrolo[2,3-b]pyridin-2-yl}prop-2-enoic acid (300 mg, 0.808 mmol) in THF (3 ml) were added DMF (0.03 ml) and oxalylchloride (0.0846 ml, 0.970 mmol), the mixture was stirred at room temperature for 1 hour and the solvent was distilled off under reduced pressure. The residue was added under ice-cooling to a solution of 4-toluidine (104 mg, 0.968 mmol), pyridine (0.262 ml, 3.24 mmol) and THF (3 ml), and the mixture was stirred under ice-cooling for 1 hour and at room temperature for 12 hours. The reaction solution was poured into water and extracted with ethyl acetate. The extract was washed with water and dried over anhydrous magnesium sulfate, and the solvent was distilled off under reduced pressure. The residue was purified by silica gel column chromatography (hexane:ethyl acetate=10:1) to give the objective product as a solid material.

Yield (amount) 140 mg, yield (rate) 46.8% $^1$H-NMR (CDCl$_3$) δ: 2.05-2.35 (7H, m), 2.59 (3H, s), 2.77 (3H, s), 2.89-3.20 (2H, m), 6.49 (1H, d, J=7.8 Hz), 6.68-7.46 (12H, m).

IR(KBr) cm$^{-1}$; 3306, 2215, 1669, 1624, 1605, 1591, 1541, 1427, 1404, 1337, 1258, 1246, 1258, 1177, 818, 747, 733.

Example 100

(2E)-N-(4-chlorophenyl)-3-{3-cyano-4,6-dimethyl-1-[(1S)-1,2,3,4-tetrahydronaphthalen-1-yl]-1H-pyrrolo[2,3-b]pyridin-2-yl}prop-2-enamide To a solution of (2E)-3-{3-cyano-4,6-dimethyl-1-[(1S)-1,2,3,4-tetrahydronaphthalen-1-yl]-1H-pyrrolo[2,3-b]pyridin-2-yl}prop-2-enoic acid (300 mg, 0.808 mmol) in THF (3 ml) were added DMF (0.03: ml) and oxalylchloride (0.0846 ml, 0.970 mmol), the mixture was stirred at room temperature for 1 hour and the solvent was distilled off under reduced pressure. The residue was added under ice-cooling to a solution of 4-chloroaniline (123 mg, 0.968 mmol), pyridine (0.262 ml, 3.24 mmol) and THF (3 ml), and the mixture was stirred under ice-cooling for 1 hour and at room temperature for 12 hours. The reaction solution was poured into water and extracted with ethyl acetate. The extract was washed with water and dried over anhydrous magnesium sulfate, and the solvent was distilled off under reduced pressure. The residue was purified by silica gel column chromatography (hexane:ethyl acetate=10:1) to give the objective product as a solid material.

Yield (amount) 117 mg, yield (rate) 30.2% $^1$H-NMR (CDCl$_3$) δ: 1.85-2.33 (4H, m), 2.60 (3H, s), 2.76 (3H, s), 2.91-3.28 (2H, m), 6.50 (1H, d, J=7.2 Hz), 6.69-7.65 (12H, m).

IR(KBr) cm$^{-1}$; 3310, 2215, 1669, 1624, 1595, 1541, 1493, 1429, 1400, 1337, 1258, 1244, 1174, 1092, 829, 733.

Example 101

(2E)-3-{3-cyano-4,6-dimethyl-1-[(1S)-1,2,3,4-tetrahydronaphthalen-1-yl]-1H-pyrrolo[2,3-b]pyridin-2-yl}-N-[4-(trifluoromethyl)phenyl]prop-2-enamide To a solution of (2E)-3-{3-cyano-4,6-dimethyl-1-[(1S)-1,2,3,4-tetrahydronaphthalen-1-yl]-1H-pyrrolo[2,3-b]pyridin-2-yl}prop-2-enoic acid (300 mg, 0.808 mmol) in THF (3 ml) were added DMF (0.03 ml) and oxalylchloride (0.0846 ml, 0.970 mmol), the mixture was stirred at room temperature for 1 hour and the solvent was distilled off under reduced pressure. The residue was added under ice-cooling to a solution of 4-trifluoromethylaniline (0.121 ml, 0.968 mmol), pyridine (0.262 ml, 3.24 mmol) and THF (3 ml), and the mixture was stirred under ice-cooling for 1 hour and at room temperature for 12 hours. The reaction solution was poured into water and extracted with ethyl acetate. The extract was washed with water and dried over anhydrous magnesium sulfate, and the solvent was distilled off under reduced pressure. The residue

Example 102

(2E)-3-{3-cyano-4,6-dimethyl-1-[(1S)-1,2,3,4-tetrahydronaphthalen-1-yl]-1H-pyrrolo[2,3-b]pyridin-2-yl}-N-(2-methoxyphenyl)prop-2-enamide To a solution of (2E)-3-{3-cyano-4,6-dimethyl-1-[(1S)-1,2,3,4-tetrahydronaphthalen-1-yl]-1H-pyrrolo[2,3-b]pyridin-2-yl}prop-2-enoic acid (300 mg, 0.808 mmol) in THF (3 ml) were added DMF (0.03 ml) and oxalylchloride (0.0846 ml, 0.970 mmol), the mixture was stirred at room temperature for 1 hour and the solvent was distilled off under reduced pressure. The residue was added under ice-cooling to a solution of 2-anisidine (0.109 ml, 0.968 mmol), pyridine (0.262 ml, 3.24 mmol) and THF (3 ml), and the mixture was stirred under ice-cooling for 2 hours and at room temperature for 12 hours. The reaction solution was poured into water and extracted with ethyl acetate. The extract was washed with water and dried over anhydrous magnesium sulfate, and the solvent was distilled off under reduced pressure. The residue was purified by silica gel column chromatography (hexane:ethyl acetate=20:1) to give the objective product as a solid material.

Yield (amount) 274 mg, yield (rate) 59.4% $^1$H-NMR (CDCl$_3$) δ: 1.96-2.35 (4H, m), 2.59 (3H, s), 2.78 (3H, s), 2.88-3.20 (2H, m), 3.90 (3H, s), 6.51 (1H, d, J=8.2 Hz), 6.67-7.42 (1OH, m), 7.91 (1H, s), 8.38 (1H, d, J=8.6 Hz).

IR(KBr) cm$^{-1}$; 3314, 2215, 1682, 1626, 1591, 1532, 1485, 1462, 1435, 1339, 1318, 1256, 1219, 1173, 1117, 1028, 748, 733.

Example 103

(2E)-3-{3-cyano-4,6-dimethyl-1-[(1S)-1,2,3,4-tetrahydronaphthalen-1-yl]-1H-pyrrolo[2,3-b]pyridin-2-yl}-N-(4-cyanophenyl)prop-2-enamide To a solution of (2E)-3-{3-cyano-4,6-dimethyl-1-[(1S)-1,2,3,4-tetrahydronaphthalen-1-yl]-1H-pyrrolo[2,3-b]pyridin-2-yl}prop-2-enoic acid (300 mg, 0.808 mmol).in THF (3 ml) were added DMF (0.03 ml) and oxalylchloride (0.0846 ml, 0.970 mmol), the mixture was stirred at room temperature for 1 hour and the solvent was distilled off under reduced pressure. The residue was added under ice-cooling to a solution of 4-aminobenzonitrile (119 mg, 0.968 mmol), pyridine (0.262 ml, 3.24 mmol) and THF (3 ml), and the mixture was stirred under ice-cooling for 2 hours and at room temperature for 12 hours. The reaction solution was poured into water and extracted with ethyl acetate. The extract was washed with water and dried over anhydrous magnesium sulfate, and the solvent was distilled off under reduced pressure. The residue was purified by silica gel column chromatography (hexane:ethyl acetate=3:1) to give the objective product as a solid material. The resultant material was recrystallized from ethyl acetate.

Yield (amount) 190 mg, yield (rate) 41.7% $^1$H-NMR (CDCl$_3$) δ: 1.97-2.32 (4H, m), 2.60 (3H, s), 2.75 (3H, s), 2.91-3.19 (2H, m), 6.51 (1H, d, J=8.8 Hz), 6.70-7.43 (7H, m), 7.58 (2H, d, J=8.8 Hz), 7.72 (2H, d, J=8.8 Hz), 8.14 (1H, s).

IR(KBr) cm$^{-1}$; 3312, 2222, 1694, 1624, 1595, 1532, 1510, 1427, 1408, 1337, 1258, 1177, 1127, 841, 748, 731.

was purified by silica gel column chromatography (hexane:ethyl acetate=10:1) to give the objective product as a solid material.

Yield (amount) 46.0 mg, yield (rate) 11.1% $^1$H-NMR (CDCl$_3$) δ: 2.05-2.33 (4H, m), 2.60 (3H, s), 2.77 (3H, s), 2.91-3.28 (2H, m), 6.51 (1H, d, J=7.4 Hz), 6.69-7.79 (12H, m).

IR(KBr) cm$^{-1}$; 3297, 2215, 1671, 1607, 1545, 1427, 1410, 1323, 1260, 1171, 1125, 1115, 1067, 843, 748.

Example 104

(2E)-N-[4-(acetylamino)phenyl]-3-{3-cyano-4,6-dimethyl-1-[(1S)-1,2,3,4-tetrahydronaphthalen-1-yl]-1H-pyrrolo[2,3-b]pyridin-2-yl}prop-2-enamide To a solution of (2E)-3-{3-cyano-4,6-dimethyl-1-[(1S)-1,2,3,4-tetrahydronaphthalen-1-yl]-1H-pyrrolo[2,3-b]pyridin-2-yl}prop-2-enoic acid (300 mg, 0.808 mmol) in THF (3 ml) were added DMF (0.03 ml) and oxalylchloride (0.0846 ml, 0.970 mmol), the mixture was stirred at room temperature for 1 hour and the solvent was distilled off under reduced pressure. The residue was added under ice-cooling to a solution of 4-amino acetanilide (145 mg, 0.968 mmol), pyridine (0.262 ml, 3.24 mmol) and THF (3 ml), and the mixture was stirred under ice-cooling for 2 hours and at room temperature for 12 hours. The reaction solution was poured into water and extracted with ethyl acetate. The extract was washed with water and dried over anhydrous magnesium sulfate, and the solvent was distilled off under reduced pressure. The residue was recrystallized from ethyl acetate.

Yield (amount) 190 mg, yield (rate) 39.0% $^1$H-NMR (CDCl$_3$) δ: 2.00-2.34 (7H, m), 2.59 (3H, s), 2.77 (3H, s), 2.77-3.20 (2H, m), 6.50 (1H, d, J=8.2 Hz), 6.68-7.54 (13H, m).

IR(KBr) cm$^{-1}$; 3274, 2215, 1665, 1615, 1566, 1512, 1427, 1404, 1319, 1258, 733.

Example 105

(2E)-3-{3-cyano-4,6-dimethyl-1-[(1S)-1,2,3,4-tetrahydronaphthalen-1-yl]-1H-pyrrolo[2,3-b]pyridin-2-yl}-N-(4-isopropylphenyl)prop-2-enamide To a solution of (2E)-3-{3-cyano-4,6-dimethyl-1-[(1S)-1,2,3,4-tetrahydronaphthalen-1-yl]-1H-pyrrolo[2,3-b]pyridin-2-yl}prop-2-enoic acid (300 mg, 0.808 mmol) in THF (3 ml) were added DMF (0.03 ml) and oxalylchloride (0.0846 ml, 0.970 mmol), the mixture was stirred at room temperature for 1 hour and the solvent was distilled off under reduced pressure. The residue was added under ice-cooling to a solution of 4-isopropylaniline (130 mg, 0.968 mmol), pyridine (0.262 ml, 3.24 mmol) and THF (3 ml), and the mixture was stirred under ice-cooling for 2 hours and at room temperature for 12 hours. The reaction solution was poured into water and extracted with ethyl acetate. The extract was washed with water and dried over anhydrous magnesium sulfate, and the solvent was distilled off under reduced pressure. The residue was purified by silica gel column chromatography (hexane:ethyl acetate=10:1) to give the objective product as a solid material.

Yield (amount) 303 mg, yield (rate) 76.9% $^1$H-NMR (CDCl$_3$) δ: 1.21 (6H, d, J=6.8 Hz), 1.97-2.34 (4H, m), 2.59 (3H, s), 2.77 (3H, s), 2.81-3.19 (3H, m), 6.49 (1H, d, J=7.6 Hz), 6.67-7.48 (12H, m).

IR(KBr) cm$^{-1}$; 3301, 2957, 2215, 1667, 1624, 1603, 1593, 1541, 1514, 1427, 1337, 1258, 1184, 910, 835, 747, 733.

Example 106

Ethyl 4-[((2E)-3-{3-cyano-4,6-dimethyl-1-[(1S)-1,2,3,4-tetrahydronaphthalen-1-yl]-1H-pyrrolo[2,3-b]pyridin-2-yl}prop-2-enoyl)amino]benzoate To a solution of (2E)-3-{3-cyano-4,6-dimethyl-1-[(1S)-1,2,3,4-tetrahydronaphthalen-1-yl]-1H-pyrrolo[2,3-b]pyridin-2-yl}prop-2-enoic acid (300 mg, 0.808 mmol) in THF (3 ml) were added DMF (0.03 ml) and oxalylchloride (0.0846 ml, 0.970 mmol), the mixture was stirred at room temperature for 1 hour and the solvent was distilled off under reduced pressure. The residue was added under ice-cooling to a solution of ethyl 4-aminobenzoate (160 mg, 0.968 mmol), pyridine (0.262 ml, 3.24 mmol) and THF (3 ml), and the mixture was stirred under ice-cooling for 2 hours and at room temperature for 12 hours. The reaction solution was poured into water and extracted with ethyl acetate. The extract was washed with water and dried over anhydrous magnesium sulfate, and the solvent was distilled off under reduced pressure. The residue was purified by silica gel column chromatography (hexane:ethyl acetate=10:1) to give the objective product as a solid material. Yield (amount) 361 mg, yield (rate) 86.2%
$^1$H-NMR (CDCl$_3$) δ: 1.38 (3H, t, J=7.0 Hz), 2.04-2.32 (4H, m), 2.60 (3H, s), 2.76 (3H, s), 2.90-3.20 (2H, m), 4.35 (2H, q, J=7.0 Hz), 6.51 (1H, d, J=7.8 Hz), 6.69-7.43 (7H, m), 7.65 (2H, d, J=8.8 Hz), 7.91 (1H, s), 8.00 (2H, d, J=8.8 Hz).
IR(KBr) cm$^{-1}$; 3314, 2215, 1715, 1692, 1626, 1599, 1537, 1424, 1408, 1339, 1277, 1256, 1173, 1107, 772, 748, 733.

Example 107

(2E)-3-{3-cyano-4,6-dimethyl-1-[(1S)-1,2,3,4-tetrahydronaphthalen-1-yl]-1H-pyrrolo[2,3-b]pyridin-2-yl}-N-methyl-N-phenylprop-2-enamide To a solution of (2E)-3-{3-cyano-4,6-dimethyl-1-[(1S)-1,2,3,4-tetrahydronaphthalen-1-yl]-1H-pyrrolo[2,3-b]pyridin-2-yl}prop-2-enoic acid (300 mg, 0.808 mmol) in THF (3 ml) were added DMF (0.03 ml) and oxalylchloride (0.0846 ml, 0.970 mmol), the mixture was stirred at room temperature for 1 hour and the solvent was distilled off under reduced pressure. The residue was added under ice-cooling to a solution of N-methylaniline (104 mg, 0.968 mmol), pyridine (0.262 ml, 3.24 mmol) and THF (3 ml), and the mixture was stirred under ice-cooling for 2 hours and at room temperature for 12 hours. The reaction solution was poured into water and extracted with ethyl acetate. The extract was washed with water and dried over anhydrous magnesium sulfate, and the solvent was distilled off under reduced pressure. The residue was purified by silica gel column chromatography (hexane:ethyl acetate=9:1) to give the objective product as powder.
Yield (amount) 274 mg, yield (rate) 73.9% $^1$H-NMR (CDCl$_3$) δ: 2.01-2.29 (4H, m), 2.55 (3H, s), 2.65 (3H, s), 2.88-3.20 (2H, m), 3.35 (3H, s), 6.46 (1H, d, J=8.0 Hz), 6.60-7.50 (12H, m).
IR(KBr) cm$^{-1}$; 2213, 1655, 1615, 1593, 1495, 1431, 1373, 1316, 1271, 1123, 748, 733, 700.

Example 108

(2E)-3-{3-cyano-4,6-dimethyl-1-[(1S)-1,2,3,4-tetrahydronaphthalen-1-yl]-1H-pyrrolo[2,3-b]pyridin-2-yl}-N-(3-methylphenyl) prop-2-enamide To a solution of (2E)-3-{3-cyano-4,6-dimethyl-1-[(1S)-1,2,3,4-tetrahydronaphthalen-1-yl]-1H-pyrrolo[2,3-b]pyridin-2-yl}prop-2-enoic acid (300 mg, 0.808 mmol) in THF (3 ml) were added DMF (0.03 ml) and oxalylchloride (0.0846 ml, 0.970 mmol), the mixture was stirred at room temperature for 1 hour and the solvent was distilled off under reduced pressure. The residue was added under ice-cooling to a solution of 3-toluidine (104 mg, 0.968 mmol), pyridine (0.262 ml, 3.24 mmol) and THF (3 ml), and the mixture was stirred under ice-cooling for 2 hours and at room temperature for 12 hours. The reaction solution was poured into water and extracted with ethyl acetate. The extract was washed with water and dried over anhydrous magnesium sulfate, and the solvent was distilled off under reduced pressure. The residue was purified by silica gel column chromatography (hexane:ethyl acetate=10:1) to give the objective product as powder.
Yield (amount) 256 mg, yield (rate) 69.0% $^1$H-NMR (CDCl$_3$) δ: 2.05-2.34 (7H, m) , 2.59 (3H, s) 2.77 (3H, s), 2.89-3.20 (2H, m), 6.49 (1H, d, J=8.2 Hz), 6.67-7.48 (12H, m).
IR(KBr) cm$^{-1}$; 3303, 2215, 1667, 1591, 1557, 1489, 1429, 1327, 1258, 1199, 747, 733.

Example 109

(2E)-3-{3-cyano-4,6-dimethyl-1-[(1S)-1,2,3,4-tetrahydronaphthalen-1-yl]-1H-pyrrolo[2,3-b]pyridin-2-yl}-N-(4-hydroxy-3-methoxyphenyl)prop-2-enamide To a solution of (2E)-3-{3-cyano-4,6-dimethyl-1-[(1S)-1,2,3,4-tetrahydronaphthalen-1-yl]-1H-pyrrolo[2,3-b]pyridin-2-yl}prop-2-enoic acid (300 mg, 0.808 mmol) in THF (3 ml) were added DMF (0.03 ml) and oxalylchloride (0.0846 ml, 0.970 mmol), the mixture was stirred at room temperature for 1 hour and the solvent was distilled off under reduced pressure. The residue was added under ice-cooling to a solution of 4-hydroxy-3-methoxyaniline (135 mg, 0.968 mmol), pyridine (0.262 ml, 3.24 mmol) and THF (3 ml), and the mixture was stirred under ice-cooling for 2 hours and at room temperature for 12 hours. The reaction solution was poured into water and extracted with ethyl acetate. The extract was washed with water and dried over anhydrous magnesium sulfate, and the solvent was distilled off under reduced pressure. The residue was purified by silica gel column chromatography (hexane:ethyl acetate=2:1) to give the objective product as a solid material.
Yield (amount) 140 mg, yield (rate) 35.3% H-NMR (CDCl$_3$) δ: 2.01-2.32 (4H, m), 2.59 (3H, s), 2.77 (3H, s), 2.88-3.20 (2H, m), 3.90 (3H, s), 5.50 (1H, s), 6.49 (1H, d, J=7.8 Hz), 6.71-7.51 (11H, m).
IR(KBr) cm$^{-1}$; 3310, 2215, 1663, 1620, 1587, 1557, 1512, 1451, 1258, 1208, 1125, 733.

Example 110

(2E)-3-{3-cyano-4,6-dimethyl-1-[(1S)-1,2,3,4-tetrahydronaphthalen-1-yl]-1H-pyrrolo[2,3-b]pyridin-2-yl}-N-(4-hydroxy-3-methoxybenzyl)prop-2-enamide To a solution of (2E)-3-{3-cyano-4,6-dimethyl-1-[(1S)-1,2,3,4-tetrahydronaphthalen-1-yl]-1H-pyrrolo[2,3-b]pyridin-2-yl}prop-2-enoic acid (300 mg, 0.808 mmol) in THF (3 ml) were added DMF (0.03 ml) and oxalylchloride (0.0846 ml, 0.970 mmol), the mixture was stirred at room temperature for 1 hour and the solvent was distilled off under reduced pressure. The residue was added under ice-cooling to a solution of 4-hydroxy-3-methoxybenzylamine hydrochloride (183 mg, 0.968 mmol), diisopropylethylamine (0.737 ml, 4.24 mmol) and THF (2 ml), and the mixture was stirred under ice-cooling for 2 hours and at room temperature for 12 hours. The reaction solution was poured into water and extracted with ethyl acetate. The extract was washed with water and dried over anhydrous magnesium sulfate, and the solvent was distilled off under reduced pressure. The residue was purified by silica gel column chromatography (hexane:ethyl acetate=1:1) to give the objective product as a solid material.
Yield (amount) 94.0 mg, yield (rate) 23.0% $^1$H-NMR (CDCl$_3$) δ: 1.95-2.32 (4H, m), 2.58 (3H, s), 2.73 (3H, s), 2.88-3.18 (2H, m), 3.86 (3H, s), 4.39 (2H, d, J=5.4 Hz), 5.69 (1H, s), 6.04 (1H, t, J=5.4 Hz), 6.49 (1H, d, J=7.8 Hz), 6.65-7.33 (10H, m).
IR(KBr) cm$^{-1}$; 3274, 2215, 1661, 1622, 1590, 1516, 1451, 1429, 1325, 1273, 1206, 1155, 1125, 1036, 910, 733.
[M+H]$^+$=507

Example 111

(2E)-N-butyl-3-{3-cyano-4,6-dimethyl-1-[(1S)-1,2,3,4-tetrahydronaphthalen-1-yl]-1H-pyrrolo[2,3-b]pyridin-2-yl}prop-2-enamide To a solution of (2E)-3-{3-cyano-4,6-dimethyl-1-[(1S)-1,2,3,4-tetrahydronaphthalen-1-yl]-1H-pyrrolo[2,3-b]pyridin-2-yl}prop-2-enoic acid (300 mg, 0.808 mmol) in THF (3 ml) were added DMF (0.03 ml) and oxalylchloride (0.0846 ml, 0.970 mmol), the mixture was stirred at room temperature for 1 hour and the solvent was distilled off under reduced pressure. The residue was added under ice-cooling to a solution of butylamine (70.8 mg, 0.968 mmol), triethylamine (0.451 ml, 3.24 mmol) and THF (2 ml), and the mixture was stirred under ice-cooling for 2 hours and at room temperature for 12 hours. The reaction solution was poured into water and extracted with ethyl acetate. The extract was washed with water and dried over anhydrous magnesium sulfate, and the solvent was distilled off under reduced pressure. The residue was purified by silica gel column chromatography (hexane:ethyl acetate=2:1) to give the objective product as a solid material.

Yield (amount) 200 mg, yield (rate) 58.1% $^1$H-NMR (CDCl$_3$) δ: 0.92 (3H, t, J=7.4 Hz), 1.22-1.55 (4H, m), 2.01-2.32 (4H, m), 2.58 (3H, s), 2.76 (3H, s), 2.88-3.18 (2H, m), 3.30 (2H, q, J=6.6 Hz), 5.68 (1H, s), 6.49 (1H, d, J=7.8 Hz), 6.65-7.29 (8H, m)

IR(KBr) cm$^{-1}$; 3287, 2215, 1661, 1622, 1588, 1553, 1427, 1327, 1264, 1219, 748, 733.

[M+H]$^+$=427

Example 112

(2E)-3-{3-cyano-4,6-dimethyl-1-[(1S)-1,2,3,4-tetrahydronaphthalen-1-yl]-1H-pyrrolo[2,3-b]pyridin-2-yl}-N-(3,4-difluorophenyl)prop-2-enamide To a solution of (2E)-3-{3-cyano-4,6-dimethyl-1-[(1S)-1,2,3,4-tetrahydronaphthalen-1-yl]-1H-pyrrolo[2,3-b]pyridin-2-yl}prop-2-enoic acid (300 mg, 0.808 mmol) in THF (3 ml) were added DMF (0.03 ml) and oxalylchloride (0.0846 ml, 0.970 mmol), the mixture was stirred at room temperature for 1 hour and the solvent was distilled off under reduced pressure. The residue was added under ice-cooling to a solution of 3,4-difluoroaniline (125 mg, 0.968 mmol), pyridine (0.262 ml, 3.24 mmol) and THF (3 ml), and the mixture was stirred under ice-cooling for 2 hours and at room temperature for 12 hours. The reaction solution was poured into water and extracted with ethyl acetate. The extract was washed with water and dried over anhydrous magnesium sulfate, and the solvent was distilled off under reduced pressure. The residue was purified by silica gel column chromatography (hexane:ethyl acetate=10 1) to give the objective product as powder.

Yield (amount) 283 mg, yield (rate) 72.8% $^1$H-NMR (CDCl$_3$) δ: 2.05-2.32 (4H, m), 2.60 (3H, s), 2.76 (3H, s), 2.90-3.19 (2H, m), 6.50 (1H, d, J=7.4 Hz), 6.69-7.75 (10H, m), 7.82 (1H, s).

IR(KBr) cm$^{-1}$; 3287, 2213, 1688, 1622, 1555, 1516, 1431, 1319, 1261, 1209, 748, 733.

[M+H]$^+$=483

The structural formulae of the compounds in Examples are shown in the following table.

TABLE 1

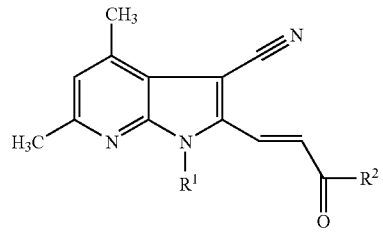

| Ex. No. | R$^1$ | R$^2$ |
|---|---|---|
| 1 | tetrahydronaphthalenyl | —NH—(2,2-dimethyltetrahydropyran-4-yl) |
| 2 | indanyl | —N(morpholino) |
| 3 | tetrahydronaphthalenyl | —N(CH$_3$)(tetrahydropyran-4-yl) |
| 4 | tetrahydronaphthalenyl | —NH—(pyridin-3-yl) |
| 5 | tetrahydronaphthalenyl | —NH—(pyridin-4-yl) |
| 6 | tetrahydronaphthalenyl | —N(morpholino) |
| 7 | tetrahydronaphthalenyl | —N(thiomorpholino) |

TABLE 1-continued
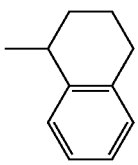
| Ex. No. | R¹ | R² |
|---|---|---|
| 8 | 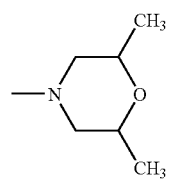 | 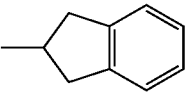 |
TABLE 2
| 9 | 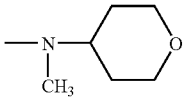 | 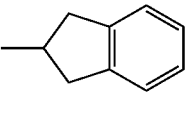 |
| 10 | 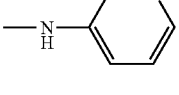 | 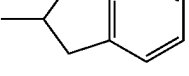 |
| 11 | 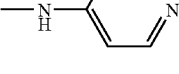 | 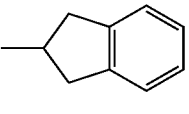 |
| 12 | 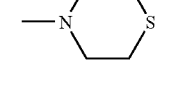 | 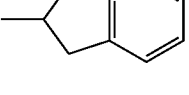 |
| 13 | 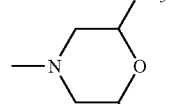 | 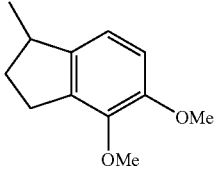 |
| 14 | 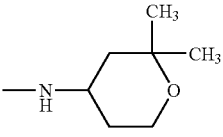 | 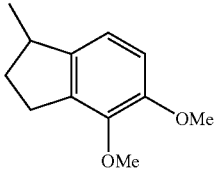 |
| 15 | 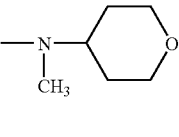 | 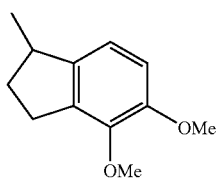 |
TABLE 2-continued
| 16 | 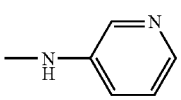 | 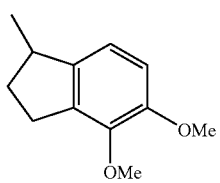 |
| 17 | 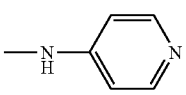 | 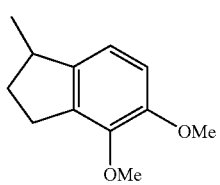 |
| 18 | 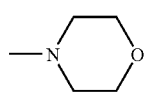 | 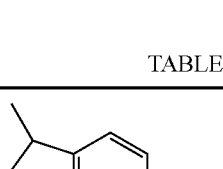 |
TABLE 3
| 19 | 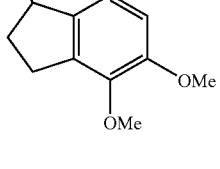 | 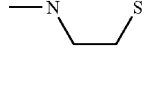 |
| 20 | 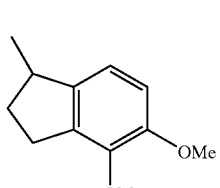 | 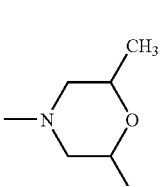 |
| 21 | 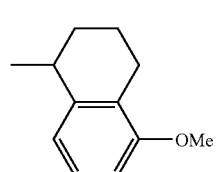 | 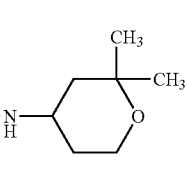 |
| 22 | 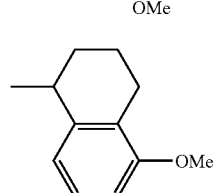 | 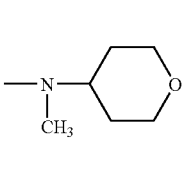 |

TABLE 3-continued
| | | |
|---|---|---|
| 23 | 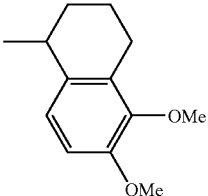 | 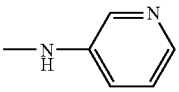 |
| 24 | 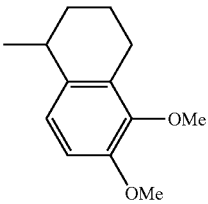 | 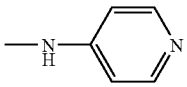 |
| 25 | 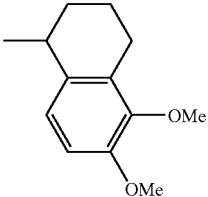 | 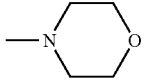 |
| 26 | 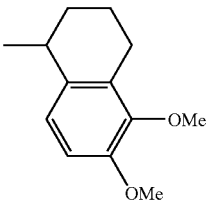 | 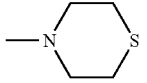 |
| 27 | 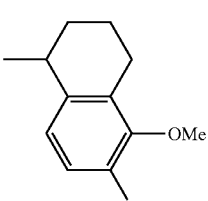 | 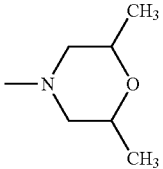 |
| 42 | 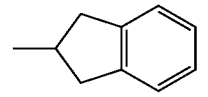 | 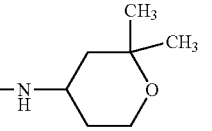 |
TABLE 4
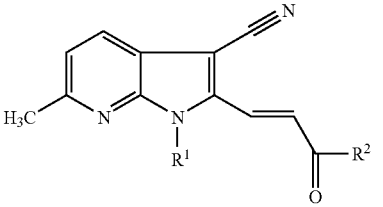
| Ex. No. | $R^1$ | $R^2$ |
|---|---|---|
| 28 | | |
| 29 | | |
| 30 | | |
| 31 | | |
| 32 | | |
| 33 | | |
| 34 | | |
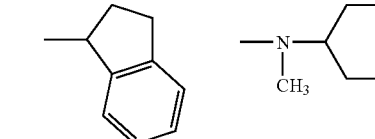

TABLE 5

Structure: 4-CH2CH3, 6-CH2CH3 substituted pyrrolo[2,3-b]pyridine with 3-CN and 2-(CH=CH-C(=O)R²), N-R¹

| Ex. No. | R¹ | R² |
|---|---|---|
| 35 | 1-indanyl | NH-(2,2-dimethyltetrahydropyran-4-yl) |
| 36 | 1-indanyl | N(CH3)-(tetrahydropyran-4-yl) |
| 37 | 1-indanyl | NH-(pyridin-3-yl) |
| 38 | 1-indanyl | NH-(pyridin-4-yl) |
| 39 | 1-indanyl | morpholin-4-yl |
| 40 | 1-indanyl | thiomorpholin-4-yl |
| 41 | 1-indanyl | 2,6-dimethylmorpholin-4-yl |

TABLE 6

Structure: 4-CH(CH3)2, 6-CH(CH3)2 substituted pyrrolo[2,3-b]pyridine with 3-CN and 2-(CH=CH-C(=O)R²), N-R¹

| Ex. No. | R¹ | R² |
|---|---|---|
| 43 | 1-indanyl | NH-(2,2-dimethyltetrahydropyran-4-yl) |
| 44 | 1-indanyl | N(CH3)-(tetrahydropyran-4-yl) |
| 45 | 1-indanyl | NH-(pyridin-3-yl) |
| 46 | 1-indanyl | NH-(pyridin-4-yl) |
| 47 | 1-indanyl | morpholin-4-yl |
| 48 | 1-indanyl | thiomorpholin-4-yl |
| 49 | 1-indanyl | 2,6-dimethylmorpholin-4-yl |

TABLE 7

(Structure: 4,6-dimethyl-7-azaindole-3-carbonitrile with N-R¹ and 2-CH=CH-C(=O)-R²)

| Ex. No. | R¹ | R² |
|---|---|---|
| 50 | 1-methyl-indanyl | -NH-(pyridin-3-yl) |
| 51 | 1-methyl-indanyl | -NH-(2,2-dimethyltetrahydropyran-4-yl) |
| 52 | 1-methyl-indanyl | -N(morpholinyl) |
| 53 | 1,1-diphenylpropyl | -NH-(pyridin-3-yl) |
| 54 | 1,1-diphenylpropyl | -NH-(2,2-dimethyltetrahydropyran-4-yl) |
| 55 | 1,1-diphenylpropyl | -N(morpholinyl) |
| 56 | 2-ethylphenylmethyl | -NH-(pyridin-3-yl) |
| 57 | phenylethyl | -NH-(2,2-dimethyltetrahydropyran-4-yl) |

TABLE 7-continued

| Ex. No. | R¹ | R² |
|---|---|---|
| 58 | phenylethyl | -N(morpholinyl) |

TABLE 8

| Ex. No. | R¹ | R² |
|---|---|---|
| 59 | 2-ethylthienyl | -NH-(pyridin-3-yl) |
| 60 | 2-ethylthienyl | -NH-(2,2-dimethyltetrahydropyran-4-yl) |
| 61 | 2-ethylthienyl | -N(morpholinyl) |
| 62 | 2-phenoxyethyl (propyl phenyl ether) | -NH-(pyridin-3-yl) |
| 63 | 2-phenoxyethyl | -NH-(2,2-dimethyltetrahydropyran-4-yl) |
| 64 | 2-phenoxyethyl | -N(morpholinyl) |
| 65 | 3-ethylpyridyl | -NH-(pyridin-3-yl) |
| 66 | 3-ethylpyridyl | -NH-(2,2-dimethyltetrahydropyran-4-yl) |
| 67 | 2-ethyltetrahydrofuranyl | -NH-(pyridin-3-yl) |

TABLE 8-continued

| Ex. No. | | |
|---|---|---|
| 68 | 2-ethyltetrahydrofuran | N-methyl-2,2-dimethyltetrahydro-2H-pyran-4-amine |
| 69 | 2-ethyltetrahydrofuran | 4-methylmorpholine |

TABLE 9

Core structure: 4,6-dimethyl-1-R¹-2-[(E)-3-oxo-3-R²-prop-1-en-1-yl]-1H-pyrrolo[2,3-b]pyridine-3-carbonitrile

| Ex. No. | R¹ | R² |
|---|---|---|
| 70 | 2,2-diphenylethyl (1-phenyl-1-phenylethyl) | NH(CH$_2$)$_2$C(CH$_3$)$_3$ |
| 71 | 2,2-diphenylethyl | N-methyl-tetrahydro-2H-pyran-4-amine |
| 72 | (R)-1,2,3,4-tetrahydronaphthalen-1-yl | (S)-N-methyl-2,2-dimethyltetrahydro-2H-pyran-4-amine |
| 73 | (R)-1,2,3,4-tetrahydronaphthalen-1-yl | (R)-N-methyl-2,2-dimethyltetrahydro-2H-pyran-4-amine |
| 74 | (S)-1,2,3,4-tetrahydronaphthalen-1-yl | (R)-N-methyl-2,2-dimethyltetrahydro-2H-pyran-4-amine |

TABLE 9-continued

| Ex. No. | R¹ | R² |
|---|---|---|
| 75 | (S)-1,2,3,4-tetrahydronaphthalen-1-yl | (S)-N-methyl-2,2-dimethyltetrahydro-2H-pyran-4-amine |
| 76 | 1-phenyl-1-(4-fluorophenyl)ethyl | N-methyl-2,2-dimethyltetrahydro-2H-pyran-4-amine |

TABLE 10

| Ex. No. | R¹ | R² |
|---|---|---|
| 77 | 1,1-bis(4-fluorophenyl)ethyl | N-methyl-2,2-dimethyltetrahydro-2H-pyran-4-amine |
| 78 | 1,1-bis(4-fluorophenyl)ethyl | 4-methylmorpholine |

TABLE 10-continued
| | | |
|---|---|---|
| 79 | 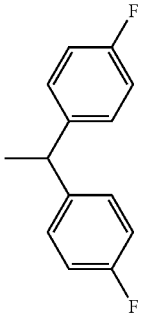 | 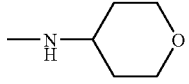 |
| 80 | 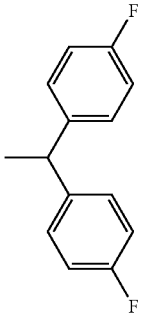 | 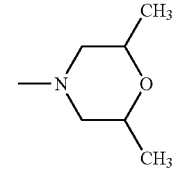 |
| 81 | 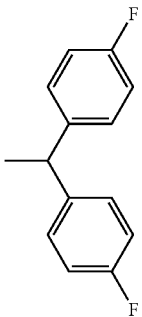 | NH(CH$_2$)$_2$C(CH$_3$)$_3$ |
| 82 | 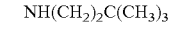 | NHC(CH$_3$)$_3$ |
| 83 | 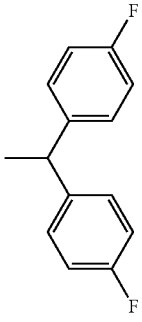 | 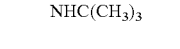 |
TABLE 11
| | | |
|---|---|---|
| 84 | 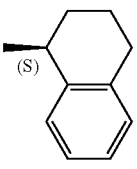 | 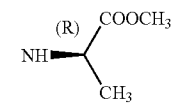 |
| 85 | 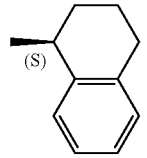 | 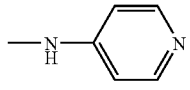 |
| 86 | 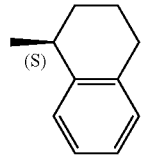 | 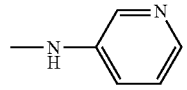 |
| 87 | 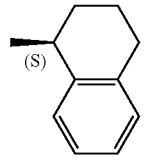 | 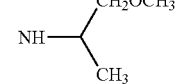 |
| 88 | 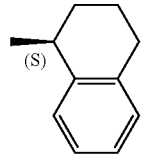 | 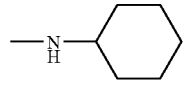 |
| 89 |  | 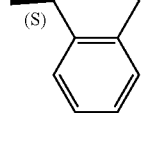 |
| 90 |  | 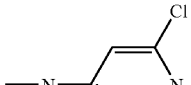 |
| 91 | 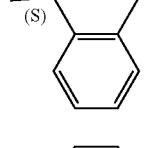 | NHCH(CH$_2$CH$_3$)$_2$ |
| 92 | 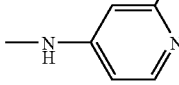 | 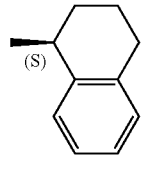 |

Example 93
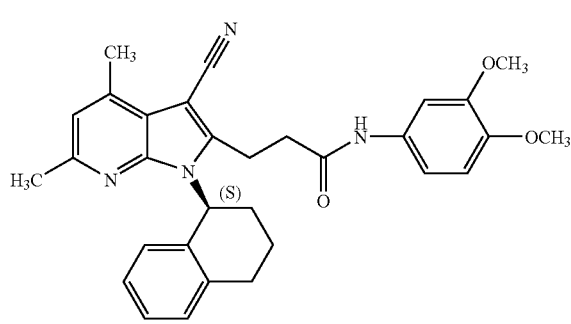
TABLE 12
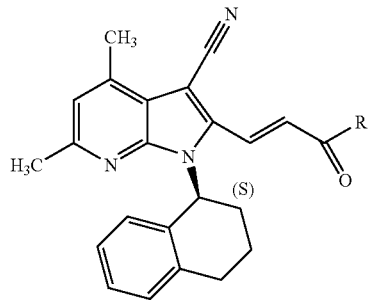
| Ex. No. | R |
|---|---|
| 94 | 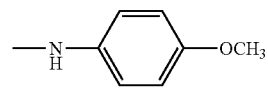 |
| 95 | 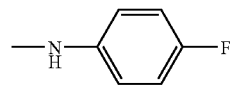 |
| 96 | 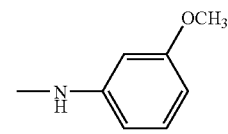 |
| 97 | 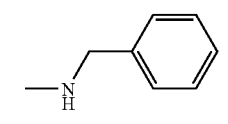 |
| 98 | 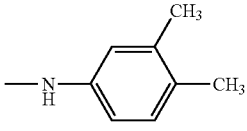 |
| 99 | 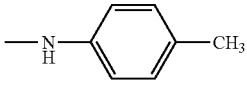 |
| 100 | 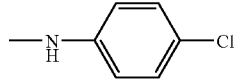 |
TABLE 12-continued
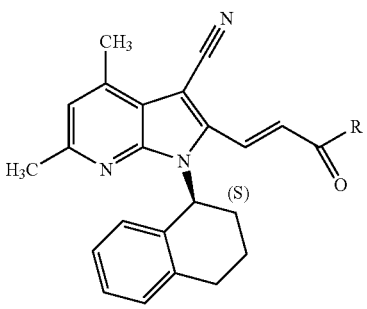
| Ex. No. | R |
|---|---|
| 101 | 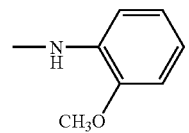 |
| 102 | 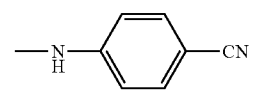 |
TABLE 13
| 103 | 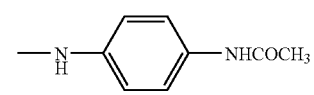 |
|---|---|
| 104 | 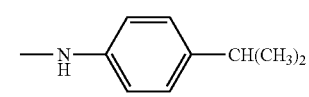 |
| 105 | 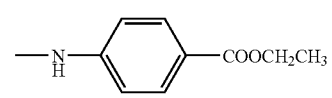 |
| 106 | 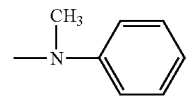 |
| 107 | 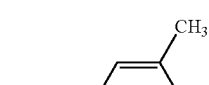 |
| 108 | 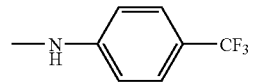 |
| 109 | 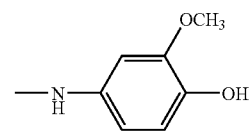 |

TABLE 13-continued

| | |
|---|---|
| 110 | 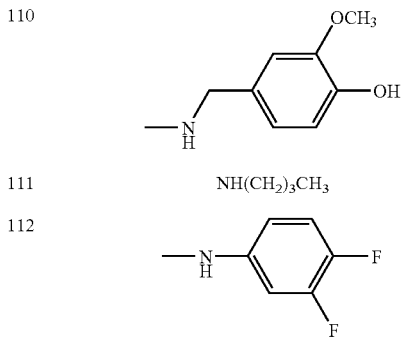 |
| 111 | NH(CH$_2$)$_3$CH$_3$ |
| 112 | (see structure) |

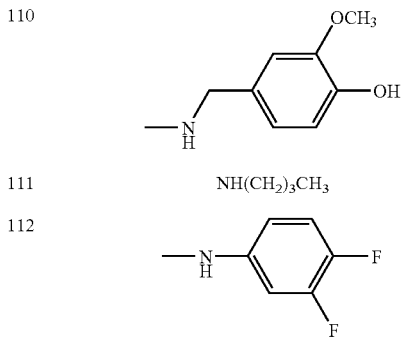

Experimental Example 1

The genetic engineering procedures described below were based on the methods described in the textbook (Maniatis et al., Molecular Cloning, Cold Spring Harbor Laboratory, 1989) or the methods described in the protocols attached to the reagents.

(1) Cloning of Rat VR1 (Vanilloid Receptor 1)

Cloning of VR1 gene was conducted by a PCR method from rat brain cDNA. Using 0.5 ng of rat brain cDNA (Takara Shuzo Co., Ltd.) as a template, the PCR reaction was carried out in a Gene Amp PCR System 9700 (Applied Biosystems) using a KOD DNA Polymerase (Toyobo Co., Ltd.) (reaction conditions: 35 cycles of treatments at 95° C. for 30 seconds, at 55° C. for 30 seconds and at 72° C. for 2 minutes) by adding 50 pmol of primers, 5'-GGGGAATTCGCCACCATGGAA-CAACGGGCTAGCTTA-3' [SEQ ID NO: 1] and 5'-GGGGCGGCCGCTTATTTCTCCCCTGG-GACCATGGAATCCTT-3' [SEQ ID NO: 2], respectively, which were prepared by referring to the base sequence of the VR1 gene reported by Caterina M. J. et al. (Nature 389 (6653): 816-24 (1997)).

(2) Preparation of Plasmid for Expression of Rat VR1

The PCR fragment obtained above was digested with restriction enzymes EcoRI (Takara Shuzo Co., Ltd.) and NotI (Takara Shuzo Co., Ltd.), and subjected to agarose gel electrophoresis to collect DNA fragments of 2.5 kb. The DNA fragment and a plasmid PMSR a neo (WO 00/44756) for expression in animal cells, which was previously digested with EcoRI and NotI, were mixed and ligated by DNA Ligation Kit Ver. 2 (Takara Shuzo Co., Ltd.). Transformation of E. coli JM109 competent cells gave plasmid pRVR1.

(3) Introduction of the Plasmid for Expression of Rat VR1 into CHO-K1 Cells and Expression thereof CHO-K1 cells (ATCC No.: CCL-61) were grown in a 150 cm$^2$ of a cell culture flask (Corning Coaster) using a Ham's F12 medium (GIBCO BRL) containing 10% fetal bovine serum (GIBCO BRL) and were collected from the flask by using 0.5 g/L trypsin-0.2 g/L EDTA (GIBCO BRL). The cells were washed with PBS (GIBCO BRL), centrifuged (1000 rpm, 5 minutes) and suspended in PBS. Then, the DNA was introduced into the cells using Gene Pulser (Bio-Rad Laboratories Inc.) under the following conditions. Namely, 1×10$^7$ cells and 15 µg of plasmid pRVR1 for expression of rat VR1 were added into a cuvette having a 0.4 cm of gap, and electroporation was carried out at an electric voltage of 0.25 kV and a capacitance of 960 µF. Subsequently, the cells were transferred into the Ham's F12 medium containing 10% fetal bovine serum, and incubated for 24 hours. The cells were then collected, centrifuged and suspended in Ham's F12 medium containing 10% fetal bovine serum and Geneticin (GIBCO BRL) at a concentration of 500 µg/ml. The suspension of cells was diluted to a concentration of 10$^4$ cells/ml, and inoculated on 96-well plates (Corning Coaster) to obtain Geneticin-resistant strains.

Subsequently, the resulting Geneticin-resistant strains were cultured in the 96-well plates (Corning Coaster). Then, after the medium was removed by suction, 100 µl of an assay buffer (1 mM CaCl$_2$, HBSS W/O sodium bicarbonate (GIBCO BRL), 0.5% BSA and 20 mM HEPES (Dojindo Molecular Technologies, Inc.), pH 7.5) was added to each well, and the cells were twice washed. Subsequently, 100 µl of the assay buffer containing 2.5 µCi/ml of $^{45}$Ca (Daiichi Pure Chemicals Co., Ltd.) and 1 µM of capsaicin (Wako Pure Chemical Industries, Ltd.) was added to each well and the reaction was carried out for 30 minutes. After the assay buffer was removed by suction, the well plate containing the cells were washed with twice 100 µl of ice-cooled PBS (GIBCO BRL), and to each well was added 150 µl of MicroScint-20 (Packard Industry Company, Inc.) with stirring. Subsequently, the radioactivity was measured with TopCount (Packard Industry Company, Inc.) to select RVR1/CHO strains of which calcium concentration in the cells is increased when capsaicin is added thereto.

(4) Cloning of Human VR1

Cloning of VR1 gene was conducted by a PCR method from human brain cDNA. Using 0.5 ng of human brain cDNA (Clonetech Inc., Quick-Clone cDNA) as the template, the PCR reaction was carried out in a Gene Amp PCR System 9700 (Applied Biosystems) using KON DNA Polymerase (Toyobo Co., Ltd.) (reaction conditions: 35 cycles of treatments at 95° C. for 30 seconds, at 55° C. for 30 seconds and at 72° C. for 2 minutes), by adding a 50 pmol of primers, 5'-GGGGAATTCGCCACCATGAAGAAATG-GAGCAGCACAGACTT-3' [SEQ ID NO: 3] and 5'-GGGGCGGCCGCTCACTTCTCCCCG-GAAGCGGCAGGACTCTT-3' [SEQ ID NO: 4], respectively, which were prepared referring to the base sequence (WO 99/37675) of the VR1 gene reported by Caterina M. J. et al.

(5) Preparation of Plasmid for Expression of Human VR1

The PCR fragment obtained above was digested with restriction enzymes EcoRI (Takara Shuzo Co., Ltd.) and NotI (Takara Shuzo Co., Ltd.), and subjected to agarose gel electrophoresis to collect DNA fragments of 2.5 kb. The DNA fragment and a plasmid pMSR a neo (WO 00/44756) for expression in animal cells, which was previously digested with EcoRI and NotI, were mixed and ligated by DNA Ligation Kit Ver. 2 (Takara Shuzo Co., Ltd.). The resulting plasmid was subjected to transformation of E. coli JM109 competent cells to obtain plasmid pHVR1.

(6) Introduction of the Plasmid for Expression of Human VR1 into CHO-K1 Cells and Expression thereof CHO-K1 cells (ATCC No.: CCL-61) were grown in a 150 cm$^2$ of a cell culture flask (Corning Coaster) using a Ham's F12 medium (GIBCO BRL) containing 10% fetal bovine serum (GIBCO BRL) and were collected by using 0.5 g/L trypsin-0.2 g/L EDTA (GIBCO BRL). The cells were washed with PBS (GIBCO BRL), centrifuged (1000 rpm, 5 minutes) and suspended in PBS. Then, DNA was introduced into the cells using Gene Pulser (Bio-Rad Laboratories Inc.) under the following conditions. Namely, 1×10$^7$ cells and 15 µg of plasmid pHVR1 for expression of rat VR1 were added into a cuvette of a 0.4 cm gap, and electroporation was carried out at an electric voltage of 0.25 kv and a capacitance of 960 µF. Subsequently, the cells were transferred into the Ham's F12 medium containing 10% fetal bovine serum, and incubated for 24 hours. The cells were then collected, centrifuged, and then suspended in Ham's F12 medium containing 10% fetal bovine serum and Geneticin (GIBCO BRL) at a concentration of 500 µg/ml. The suspension of cells was diluted to a concentration of 104 cells/ml, which was inoculated on 96-well plates (Corning Coaster) to obtain Geneticin-resistant strains. Subsequently, the resulting Geneticin-resistant strains were cultured in the 96-well plates (Corning Coaster). Then, after the medium was removed by suction, 100 μl of an assay buffer (1 mM $CaCl_2$, HBSS W/O sodium bicarbonate (GIBCO BRL), 0.5% BSA and 20 mM HEPES (Dojindo Molecular Technologies, Inc.), pH 7.5) was added to each well, and the cells were twice washed. Subsequently, 100 μl of the assay buffer containing 2.5 μCi/ml of $^{45}Ca$ (Daiichi Pure Chemicals. Co., Ltd.) and 1 μM of capsaicin (Wako Pure Chemical Industries, Ltd.) were added to each well and the reaction was carried out for 30 minutes. After the assay buffer was removed by suction, the cells were washed with twice 100 μl of ice-cooled PBS (GIBCO BRL), and to each well was added 150 μl of MicroScint-20 (Packard Industry Company, Inc.) with stirring. Subsequently, the radioactivity was determined with Top Count (Packard Industry Company, Inc.) to select HVR1/CHO strains of which calcium concentration in the cells is increased when capsaicin is added thereto.

(7) Evaluation of Compounds Based on Cell Death

Caterina M. J. et al. (Nature 389 (6653): 816-24 (1997)) have reported that cells expressing vanilloid receptor-1 died in the presence of capsaicin. The compounds were evaluated based on this. RVR1/CHO and HVR1/CHO strains were inoculated on 96-well microplates (Corning Coaster) at a concentration of $4 \times 10^4$ cells/well, respectively and were cultured for 20 hours. After the culture was removed by suction, 180 μl of a Ham's F12 medium (GIBCO BRL) containing 10% fetal bovine serum (GIBCO BRL) was added to each well. Then, 20 μl of the assay buffer (Ham's F12 medium (GIBCO BRL), 0.5% BSA and 20 mM HEPES (Dojindo Molecular Technologies, Inc.), pH 7.5) containing a test compound at a final concentration of 1 μM was added to each well and the reaction was carried out in a carbon dioxide incubator for 3 hours. Subsequently, 25 μl of Alama Blue (Wako Pure Chemical Industries, Ltd.) was added to each well, and again cultured for 20 hours. Then, fluorescence was measured at an excitation wavelength of 530 nm and a fluorescence wavelength of 590 nm using a multilabel counter (Wallac-Berthold Japan Co., Ltd.), and a survival rate of cell was determined.

According to the above-mentioned method, the agonist activity of test compounds was determined. As a result, the survival rate of the cells in the presence of 1 μM of the compound which was obtained in Example 74 was 2%.

From the results, it was shown that the compound of the present invention has excellent vanilloid receptor agonist activity.

Test Example 2

Mouse Eye Dropping Test

Eight of 4 to 5 weeks old ICR male mice (Japan SLC Inc.) were used in a group in this test. 0.01 ml of the drug was added dropwise to the eye, and the time when the mouse continued to close the eye was measured. The stimulation of the drug was evaluated as positive when the time is more than 10 seconds, and as negative when the time is 10 seconds or less. At 1 hour after the initial treatment, a solution of capsaicin (0.3 μg) was added dropwise to the eye to evaluate whether the stimulation is or not, and examined the desensitizing activity of the compound. The stimulating and desensitizing activity of the drug were calculated as a value of $ED_{50}$. The drug was dissolved in a mixture of 10% ethanol, 20% Tween 80 and 70% physiological saline solution.

$ED_{50}$ of the compound obtained in Example 74 was 0.55 μg.

From the results, it was shown that the compound of the present invention has excellent desensitizing activity.

Test Example 3

Measurement of Mouse Bladder Volume

Six or seven of 7 weeks old SD male rats were used in a group in this test. At 12 hours after the subcutaneous administration of the drug, the abdomen of rat was cut open under urethane anesthesia (1.2 g/kg, ip) to expose the bladder. Physiological saline solution was infused into the bladder at the rate of 0.1 ml/minutes to check excretion reflection. All of the urine was drained off, and the physiological saline solution was infused again, and then, the bladder volume of mouse was calculated by measuring the time to urination. The results are shown in Table 14.

TABLE 14

| | Dose (mg/kg, sc) | Bladder capacity (mL) |
|---|---|---|
| Vehicle | — | 0.75 ± 0.19 |
| Example 51 | 3 | 1.76 ± 0.37* |
| | 10 | 1.57 ± 0.23* |

*$P \leq 0.025$ v.s. vehicle-treated group (William's test).

From the results, it was shown that the compound of the present invention has excellent actions of preventing or treating frequent urination and/or urinary incontinence by increasing the bladder volume.

Test Example 4

Tail-Flick Test

Eight of 5 weeks old ICR male mice were used in a group in this test. The tail of the mouse was dipped by about 2 cm from the end into water in a water bath warmed to 55° C., and the latency to lift the tail up was measured. The latency was previously measured before the administration of the drug, and the mouse having the latency of 2 seconds or less was selected and used in the test. The drug was administered orally, and the latency was measured after 3, 6 and 24 hours. Cut-off time was set to 5 seconds. The drug was suspended in 0.5% methylcellulose, and the dose was 20 ml/kg BW. The results are shown in Table 15.

TABLE 15

| | | Latency (sec) | | | |
|---|---|---|---|---|---|
| Time after administration | | Pre | 3 h | 6 h | 24 h |
| Vehicle | | 0.67 ± 0.05 | 0.59 ± 0.02 | 0.55 ± 0.02 | 0.63 ± 0.04 |
| Example 51 (mg/kg, po) | 10 | 0.55 ± 0.02 | 0.85 ± 0.10 | 0.64 ± 0.04 | 0.78 ± 0.04 |
| | 30 | 0.70 ± 0.07 | 2.31 ± 1.13** | 2.04 ± 1.15* | 3.36 ± 1.02* |

*$\leq 0.05$, **$\leq 0.01$ v.s. vehicle-treated group (Dunnett's test).

From the results, it was shown that the compound of the present invention has excellent analgesic actions.

INDUSTRIAL APPLICABILITY

The present invention provides a novel pyrrolopyridine derivative which has vanilloid receptor agonist activity and is useful as a medicine such as an agent for preventing and/or treating overactive bladder and an analgesic.

The invention claimed is:

1. A compound represented by the formula

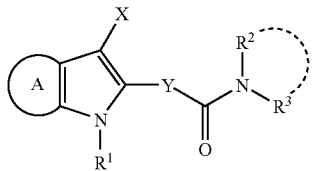

(I)

wherein Ring A represents a pyridine ring which may have one or two $C_{1-4}$ alkly groups, X represents a nitrile group, Y represents —CH=CH— or —(CH$_2$)$_2$, $R^1$ represents (1) a $C_{5-7}$ cycloalkyl group optionally fused with a benzene ring, (2) a $C_{7-19}$ aralkyl group, (3) a 5- or 6-membered heterocyclic ring-$C_{1-4}$ alkyl group or (4) a $C_{6-14}$ aryloxy-$C_{1-4}$ alkyl group, each of which may have 1 to 4 substituents selected from a halogen atom, a $C_{1-4}$ alkyl group, a mono-, di- or tri-halogeno-$C_{1-4}$ alkyl group and a $C_{1-4}$ alkoxy group, and one of $R^2$ and $R^3$ is a hydrogen atom or a $C_{1-4}$ alkyl group, and the other is a $C_{6-14}$ aryl group, a $C_{7-19}$ aralkyl group, a $C_{3-10}$ cycloalkyl group, a tetrahydropyranyl group, a pyranyl group or a pyridyil group or a $C_{1-6}$ alkyl group, each of which may have 1 to 4 substituents selected from a halogen atom, a $C_{1-4}$ alkyl group, a mono-, di- or tri-halogeno-$C_{1-4}$ alkyl group, a $C_{1-4}$ alkoxy group, a $C_{1-4}$ alkoxy-carbonyl group, a cyano group, a $C_{1-4}$ alkyl-carbonylamino group and a hydroxyl group or a salt thereof.

2. (2E)-3-{3-cyano-4,6-dimethyl-1-[(1S)-1,2,3,4-tetrahydronaphthalen-1-yl]-1H-pyrrolo[2,3-b]pyridin-2-yl}-N-(3,4-dimethoxyphenyl)prop-2-enamide, (2E)-3-{3-cyano-4,6-dimethyl-1-[(1S)-1,2,3,4-tetrahydronaphthalen-1-yl]-1H-pyrrolo[2,3-b]pyridin-2-yl}-N-(3,4-dimethylphenyl)prop-2-enamide, (2E)-3-{3-cyano-4,6-dimethyl-1-[(1S)-1,2,3,4-tetrahydronaphthalen-1-yl]-1H-pyrrolo[2,3-b]pyridin-2-yl}-N-methyl-N-phenylprop-2-enamide, (2E)-3-{3-cyano-4,6-dimethyl-1-[(1S)-1,2,3,4-tetrahydronaphthalen-1-yl]-1H-pyrrolo[2,3-b]pyridin-2-yl}-N-(3-methylphenyl)prop-2-enamide, (2E)-3-{3-cyano-4,6-dimethyl-1-[(1S)-1,2,3,4-tetrahydronaphthalen-1-yl]-1H-pyrrolo[2,3-b]pyridin-2-yl}-N-(4-hydroxy-3-methoxyphenyl)prop-2-enamide, or salts thereof.

3. A vanilloid receptor agonist comprising the compound according to claim 1.

4. The vanilloid receptor agonist according to claim 3 which is for local administration.

5. The vanilloid receptor agonist according to claim 3 which is an agent for treating overactive bladder.

6. The vanilloid receptor agonist according to claim 3 which is an analgesic.

7. A method of treating overactive bladder, comprising administering to a mammal in need an effective amount of the compound according to claim 1.

8. A method of inducing analgesia in a mammal in need thereof comprising administering an effective amount of the compound according to claim 1.

* * * * *